US012595263B2

(12) United States Patent
Cheng et al.

(10) Patent No.: US 12,595,263 B2
(45) Date of Patent: Apr. 7, 2026

(54) PYRAZOLOPYRIMIDINE COMPOUND USED AS ATR KINASE INHIBITOR

(71) Applicant: BEIJING TIDE PHARMACEUTICAL CO., LTD., Beijing (CN)

(72) Inventors: Cheung Ling Cheng, Beijing (CN); Yanping Zhao, Beijing (CN); Hongjun Wang, Beijing (CN); Bin Liu, Beijing (CN); Weiting Zhong, Beijing (CN); Huifen Xu, Beijing (CN); Chuangchuang Huang, Beijing (CN); Jing Li, Beijing (CN); Weina Liu, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 485 days.

(21) Appl. No.: 18/016,164

(22) PCT Filed: Jul. 13, 2021

(86) PCT No.: PCT/CN2021/105867

§ 371 (c)(1),
(2) Date: Jan. 13, 2023

(87) PCT Pub. No.: WO2022/012484

PCT Pub. Date: Jan. 20, 2022

(65) Prior Publication Data

US 2023/0271968 A1 Aug. 31, 2023

(30) Foreign Application Priority Data

Jul. 13, 2020 (CN) ......................... 202010669088.1
Oct. 27, 2020 (CN) ......................... 202011163505.1

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
None
See application file for complete search history.

(56) References Cited

U.S. PATENT DOCUMENTS

2023/0242533 A9* 8/2023 Cai .................... A61K 31/5377 514/232.5

FOREIGN PATENT DOCUMENTS

| | | | |
|---|---|---|---|
| CN | 1236780 | A | 12/1999 |
| CN | 103613591 | A | 3/2014 |
| CN | 112142744 | A | 12/2020 |
| CN | 114423756 | A | 4/2022 |
| KR | 1020220035917 | A | 3/2022 |
| WO | 2005028444 | A1 | 3/2005 |
| WO | 2005030130 | A2 | 4/2005 |
| WO | 2011123493 | A1 | 10/2011 |
| WO | 2011154737 | A1 | 12/2011 |
| WO | 2012044641 | A1 | 4/2012 |
| WO | 2012151562 | A1 | 11/2012 |
| WO | 2012178123 | A1 | 12/2012 |
| WO | 2013010136 | A2 | 1/2013 |
| WO | 2013024002 | A1 | 2/2013 |
| WO | 2013028263 | A1 | 2/2013 |
| WO | 2015055071 | A1 | 4/2015 |
| WO | 2016020320 | A1 | 2/2016 |
| WO | 2016064957 | A1 | 4/2016 |
| WO | 2017215485 | A1 | 12/2017 |
| WO | 2020049017 | A1 | 3/2020 |
| WO | 2020259601 | A1 | 12/2020 |

OTHER PUBLICATIONS

Degorce et al., "Discovery of Novel 3-Quinoline Carboxamides as Potent, Selective and Orally Bioavailable Inhibitors of Ataxia Telangiectasia Mutated (ATM) Kinase", Journal of Medicinal Chemistry, 2016, 56, pp. 6281-6292.
Mortensen et al., "Discovery and SAR exploration of a novel series of imidazo[4,5-b]pyrazin-2-ones as potent and selective mTOR kinase inhibitors", Bioorganic & Medicinal Chemistry Letters, 21 (2011) pp. 6793-6799.
Goldberg et al., "The Discovery 7-Methyl-2-[(7-methyl[1,2,4]triazolo[1,5-a]pyridin-6-yl)amino]-9-(tetrahydro-2H-pyran-4-yl)-7,9-dihydro-8H-purin-8-one (AZD7648), a Potent and Selective DNA-Dependent Protein Kinase (DNA-PK) Inhibitor", Journal of Medicinal Chemistry, 2020, 63, pp. 3461-3471.

* cited by examiner

*Primary Examiner* — Jeffrey S Lundgren
*Assistant Examiner* — Anthony Joseph Seitz
(74) *Attorney, Agent, or Firm* — Lando & Anastasi, LLP

(57) ABSTRACT

Disclosed is a compound of a general formula (I), which may be used for the treatment of ATR kinase-mediated diseases, for example, proliferative diseases such as cancer. Further disclosed are a preparation method for the compound of the general formula (I), a pharmaceutical composition, and use of the pharmaceutical composition for the treatment of ATR kinase-mediated diseases.

(I)

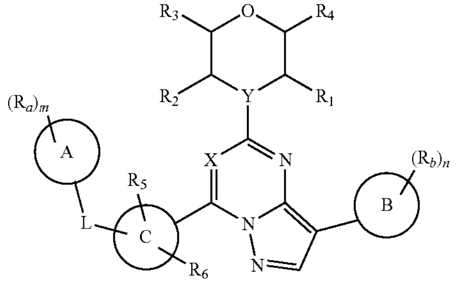

31 Claims, No Drawings

PYRAZOLOPYRIMIDINE COMPOUND USED AS ATR KINASE INHIBITOR

CROSS-REFERENCE TO RELATED APPLICATIONS

This application is a U.S. national phase application and claims the benefit of priority under 35 U.S.C. § 371, of International (PCT) Patent Application Serial No. PCT/CN2021/105867, filed on Jul. 13, 2021, which claims priority to Chinese Patent Application No. 202010669088.1, filed on Jul. 13, 2020, and Chinese Patent Application No. 202011163505.1, filed on Oct. 27, 2020, each of which is incorporated herein by reference in its entirety for all purposes.

FIELD OF THE INVENTION

The present disclosure relates to pyrazolopyrimidine compounds as ATR kinase inhibitors. More specifically, the compound of the present disclosure is effective in the treatment of diseases mediated by ATR kinase, for example, proliferative diseases such as cancers. The present disclosure also provides a pharmaceutical composition of the compound, use of the compound for treating diseases mediated by ATR kinase, and preparation of the compound.

BACKGROUND OF THE INVENTION

ATR (Ataxia telangiectasia and Rad3-related protein) is a class of protein kinase involved in genome stability and DNA damage repair. It belongs to PIKK family. The activation of ATR can be activated by stagnant replication forks or DNA single strand breakage (SSB). The activated ATR will recruit repair proteins or repair factors to repair the damaged parts and delay the mitotic process (especially in the G2/M phase of mitosis), which not only stabilizes the replication fork, but also ensures the stability of the genome.

In addition, the DNA damage repair system in most tumor cells is abnormal, which usually lacks a certain repair pathway (such as p53 or ATM mutation), making them more dependent on ATR for survival. In normal cells, due to its robust and complete repair pathway, inhibition of ATR kinase alone will not produce a great impact. Therefore, inhibition of ATR may have a more significant effect on the treatment of cancer without great toxic side effects on normal cells.

Moreover, the inhibition of ATR can be combined with radiotherapy or chemotherapy drugs to synergistically enhance the effect. Widely used chemotherapeutic drugs include antimetabolites (such as gemcitabine), DNA cross-linking agents (such as cisplatin, carboplatin), and alkylating agents (such as temozolomide), topoisomerase inhibitors (such as topotecan, irinotecan), etc. When tumor cells are affected by chemotherapy or radiotherapy, the ATR signaling pathway was activated to a greater extent to repair damaged DNA. Therefore, when using radiotherapy or chemotherapy to treat cancer, at the same time inhibiting ATR, the therapeutic effect on cancer can be greatly enhanced.

So far, there is still no ATR inhibitor on the market, so it is still necessary to discover more effective and safer ATR inhibitors.

SUMMARY OF THE INVENTION

The present disclosure provides a compound of general formula (I), which can be used for treating diseases mediated by ATR kinase, for example, proliferative diseases such as cancers.

In one aspect, the present disclosure provides a compound of general formula (I), or a pharmaceutically acceptable salt, enantiomer, diastereomer, racemate, solvate, hydrate, polymorph, prodrug, or isotopic variant thereof, or a mixture thereof:

(I)

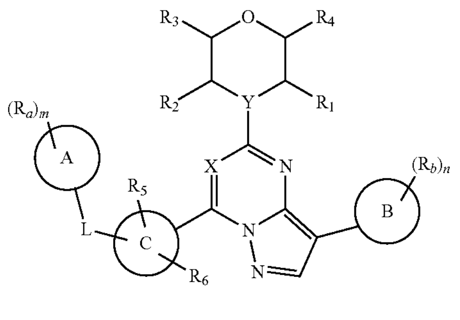

wherein

X is $CR_X$ or N;

Y is $CR_Y$ or N;

$R_1$, $R_2$, $R_3$, $R_4$ and $R_Y$ are independently selected from H, D, halogen, $C_{1-6}$ alkyl, $C_{2-6}$ alkenyl and $C_{2-6}$ alkynyl, or $R_1$ and $R_2$, $R_3$ and $R_4$ are connected to form bond, $C_{1-6}$ alkylene, $C_{2-6}$ alkenylene or $C_{2-6}$ alkynylene; wherein the groups may be substituted by one or more D or halogens up to fully substituted;

wherein $R_X$ is H, D, halogen, —CN, —NRR', —OR, —SR or $C_{1-6}$ alkyl, wherein the groups may be substituted by one or more D or halogens up to fully substituted;

when Y is $CR_Y$, $R_Y$ and $R_1$ are taken together with the atoms to which they are attached to form $C_{3-5}$ cycloalkyl or 3- to 5-membered heterocyclyl, wherein the groups may be substituted by one or more D or halogens up to fully substituted;

ring A is $C_{3-7}$ cycloalkyl, 4- to 7-membered heterocyclyl, $C_{6-10}$ aryl or 5- to 10-membered heteroaryl; or ring A is absent, so one $R_a$ is connected to L; or even $(R_a)_m$-ring A-L- is absent;

$R_a$ is independently selected from H, D, halogen, —CN, —NRR', —OR, —SR, —C(O)R, —C(O)OR, —C(O)NRR', —OC(O)R', —NRC(O)R', —OC(O)NRR', —NRC(O)NRR', —$S(O)_pR$, $C_{1-6}$ alkyl, $C_{2-6}$ alkenyl, $C_{2-6}$ alkynyl, $C_{3-7}$ cycloalkyl and 3- to 8-membered heterocyclyl, each of which is optionally substituted with R*, wherein the groups may be substituted by one or more D or halogens up to fully substituted;

m is 0, 1, 2, 3, 4 or 5;

ring B is 5- to 6-membered heteroaryl;

$R_b$ is independently selected from H, D, halogen, —CN, —NRR', —OR, —SR, —C(O)R, —C(O)OR, —C(O)NRR', —OC(O)R', —NRC(O)R', —OC(O)NRR', —NRC(O)NRR', —$S(O)_pR$, $C_{1-6}$ alkyl, $C_{2-6}$ alkenyl, $C_{2-6}$ alkynyl, $C_{3-7}$ cycloalkyl and 3- to 8-membered heterocyclyl, each of which is optionally substituted with R*, wherein the groups may be substituted by one or more D or halogens up to fully substituted;

n is 0, 1, 2, 3, 4 or 5;

ring C is $C_{3-7}$ cycloalkyl, 4- to 7-membered heterocyclyl, $C_{6-10}$ aryl or 5- to 10-membered heteroaryl;

L is a bond, —O—, —S—, —N(R)—, —C(O)—, $C_{1-6}$ alkylene, $C_{2-6}$ alkenylene or $C_{2-6}$ alkynylene;

$R_5$ is H, D, halogen, —CN, —NRR', —OR, —SR, $C_{1-6}$ alkyl, $C_{2-6}$ alkenyl or $C_{2-6}$ alkynyl, wherein the groups may be substituted by one or more D or halogens up to fully substituted;

$R_6$ is H, D, halogen, —CN, —NRR', —OR, —SR, $C_{1-6}$ alkyl, $C_{2-6}$ alkenyl or $C_{2-6}$ alkynyl, wherein the groups may be substituted by one or more D or halogens up to fully substituted;

R* is H, halogen, —CN, —NRR', —OR, —SR, —C(O)R, —C(O)OR, —C(O)NRR', —OC(O)R', —NRC(O)R', —OC(O)NRR', —NRC(O)NRR', —$S(O)_p$R, $C_3$-7 cycloalkyl, 3- to 8-membered heterocyclyl, $C_{6-10}$ aryl or 5- to 10-membered heteroaryl, wherein the groups may be substituted by one or more D or halogens up to fully substituted;

R and R' are independently selected from H, $C_{1-6}$ alkyl, $C_{2-6}$ alkenyl and $C_{2-6}$ alkynyl, or R and R' are taken together with the nitrogen atom to which they are attached to form 4- to 8-membered heterocyclyl; wherein the groups may be substituted by one or more D or halogens up to fully substituted;

p is 1 or 2.

In another aspect, the present disclosure provides a pharmaceutical composition comprising a compound disclosed herein, and optionally pharmaceutically acceptable excipient(s).

In another aspect, the present disclosure provides a pharmaceutical composition comprising a compound disclosed herein and pharmaceutically acceptable excipient(s), which further comprises other therapeutic agent(s).

In another aspect, the present disclosure provides a kit comprising a compound disclosed herein, other therapeutic agent(s), and pharmaceutically acceptable carrier(s), adjuvant(s) or vehicle(s).

In another aspect, the present disclosure provides a use of a compound disclosed herein in the manufacture of a medicament for treating and/or preventing a disease mediated by ATR kinase.

In another aspect, the present disclosure provides a method of treating and/or preventing a disease mediated by ATR kinase in a subject, comprising administering to the subject a compound disclosed herein or a composition disclosed herein.

In another aspect, the present disclosure provides a compound disclosed herein or a composition disclosed herein, for use in treating and/or preventing a disease mediated by ATR kinase.

In a specific embodiment, the disease includes: proliferative diseases (such as cancer), especially solid tumors (such as carcinoma and sarcoma), leukemia and lymphoma, especially, for example, breast cancer, colorectal cancer, lung cancer (including small cell lung cancer, non-small cell lung cancer and bronchioloalveolar carcinoma), prostate cancer and bile duct cancer, bone cancer, bladder cancer, head and neck cancer, kidney cancer, liver cancer, gastrointestinal cancer, esophageal cancer, ovarian cancer, pancreatic cancer, skin cancer, testicular cancer, thyroid cancer, uterine cancer, cervical cancer and vulvar cancer, and leukemia [including acute lymphoblastic leukemia (ALL), chronic myeloid leukemia (CML) and acute myeloid leukemia (AML), etc.], multiple myeloma and lymphoma.

Other objects and advantages of the present disclosure will be apparent to those skilled in the art from the specific embodiments, examples and claims disclosed herein.

Definition

Chemical Definitions

Definitions of specific functional groups and chemical terms are described in more detail below.

When a range of values is listed, it is intended to encompass each value and sub-range within the range. For example "$C_{1-6}$ alkyl" is intended to include $C_1$, $C_2$, $C_3$, $C_4$, $C_5$, $C_6$, $C_{1-6}$, $C_{1-5}$, $C_{1-4}$, $C_{1-3}$, $C_1$-2, $C_2$-6, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

"$C_{1-6}$ alkyl" refers to a radical of a straight or branched, saturated hydrocarbon group having 1 to 6 carbon atoms. In some embodiments, $C_{1-4}$ alkyl is alternative. Examples of $C_{1-6}$ alkyl include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentyl ($C_5$), pentyl ($C_5$), neopentyl ($C_5$), 3-methyl-2-butyl ($C_5$), tert-pentyl ($C_5$) and n-hexyl ($C_6$). The term "$C_{1-6}$ alkyl" also includes heteroalkyl, wherein one or more (e.g., 1, 2, 3 or 4) carbon atoms are substituted with heteroatoms (e.g., oxygen, sulfur, nitrogen, boron, silicon, phosphorus). Alkyl groups can be optionally substituted with one or more substituents, for example, with 1 to 5 substituents, 1 to 3 substituents or 1 substituent. Conventional abbreviations of alkyl include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$) or i-Bu (—$CH_2CH(CH_3)_2$).

"$C_{2-6}$ alkenyl" refers to a radical of a straight or branched hydrocarbon group having 2 to 6 carbon atoms and at least one carbon-carbon double bond. In some embodiments, $C_{2-4}$ alkenyl is alternative. Examples of $C_{2-6}$ alkenyl include vinyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl ($C_6$), etc. The term "$C_{2-6}$ alkenyl" also includes heteroalkenyl, wherein one or more (e.g., 1, 2, 3 or 4) carbon atoms are replaced by heteroatoms (e.g., oxygen, sulfur, nitrogen, boron, silicon, phosphorus). The alkenyl groups can be optionally substituted with one or more substituents, for example, with 1 to 5 substituents, 1 to 3 substituents or 1 substituent.

"$C_{2-6}$ alkynyl" refers to a radical of a straight or branched hydrocarbon group having 2 to 6 carbon atoms, at least one carbon-carbon triple bond and optionally one or more carbon-carbon double bonds. In some embodiments, $C_{2-4}$ alkynyl is alternative. Examples of $C_{2-6}$ alkynyl include, but are not limited to, ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$), etc. The term "$C_{2-6}$ alkynyl" also includes heteroalkynyl, wherein one or more (e.g., 1, 2, 3 or 4) carbon atoms are replaced by heteroatoms (e.g., oxygen, sulfur, nitrogen, boron, silicon, phosphorus). The alkynyl groups can be substituted with one or more substituents, for example, with 1 to 5 substituents, 1 to 3 substituents or 1 substituent.

"$C_{1-6}$ alkylene, $C_{2-6}$ alkenylene or $C_{2-6}$ alkynylene" refers to a divalent group of the "$C_{1-6}$ alkyl, $C_{2-6}$ alkenyl or $C_{2-6}$ alkynyl" as defined above.

"$C_{1-6}$ alkylene" refers to a divalent group formed by removing another hydrogen of the $C_{1-6}$ alkyl, and can be a substituted or unsubstituted alkylene. In some embodiments, $C_{1-4}$ alkylene is yet alternative. The unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), etc. Examples of substituted alkylene groups, such as those substituted with one or more alkyl (methyl) groups, include, but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, $—CH_2CH_2CH(CH_3)—$, $—C(CH_3)_2CH_2CH_2—$, $—CH_2C(CH_3)_2CH_2—$, $—CH_2CH_2C(CH_3)_2—$), etc.

"$C_{2-6}$ alkenylene" refers to a $C_{2-6}$ alkenyl group wherein another hydrogen is removed to provide a divalent radical of alkenylene, and which may be substituted or unsubstituted alkenylene. In some embodiments, $C_{2-4}$ alkenylene is yet alternative. Exemplary unsubstituted alkenylene groups include, but are not limited to, ethenylene ($—CH=CH—$) and propenylene (e.g., $—CH=CHCH_2—$, $—CH_2—CH=CH—$). Exemplary substituted alkenylene groups, e.g., substituted with one or more alkyl (methyl) groups, include but are not limited to, substituted ethylene ($—C(CH_3)=CH—$, $—CH=C(CH_3)—$), substituted propylene (e.g., $—C(CH_3)=CHCH_2—$, $—CH=C(CH_3)CH_2—$, $—CH=CHCH(CH_3)—$, $—CH=CHC(CH_3)_2—$, $—CH(CH_3)—CH=CH—$, $—C(CH_3)_2—CH=CH—$, $—CH_2—C(CH_3)=CH—$, $—CH_2—CH=C(CH_3)—$), and the like.

"$C_{2-6}$ alkynylene" refers to a $C_{2-6}$ alkynyl group wherein another hydrogen is removed to provide a divalent radical of alkynylene, and which may be substituted or unsubstituted alkynylene. In some embodiments, $C_{2-4}$ alkynylene is yet alternative. Exemplary alkynylene groups include, but are not limited to, ethynylene ($—C≡C—$), substituted or unsubstituted propynylene ($—C≡CCH_2—$), and the like.

"$C_{1-6}$ alkoxy" refers to the group —OR wherein R is a substituted or unsubstituted $C_{1-6}$ alkyl. In some embodiments, $C_{1-4}$ alkoxy group is yet alternative. Specific alkoxy groups include, but are not limited to, methoxy, ethoxy, n-propoxy, isopropoxy, n-butoxy, tert-butoxy, sec-butoxy, n-pentyloxy, n-hexyloxy and 1,2-dimethylbutoxy. The alkoxy can be optionally substituted with one or more substituents, for example, with 1 to 5 substituents, 1 to 3 substituents or 1 substituent.

"Halo" or "halogen" refers to fluorine (F), chlorine ($C_1$), bromine (Br) and iodine (I).

Thus, "$C_{1-6}$ haloalkyl" and "$C_{1-6}$ haloalkoxy" refer to the above "$C_{1-6}$ alkyl" and "$C_{1-6}$ alkoxy", which are substituted by one or more halogen. In some embodiments, $C_{1-4}$ haloalkyl is yet alternative, and still alternatively $C_{1-2}$ haloalkyl. In some embodiments, $C_{1-4}$ haloalkoxy group is yet alternative, and still alternatively $C_{1-2}$ haloalkoxy group. Exemplary haloalkyl groups include, but are not limited to, $—CF_3$, $—CH_2F$, $—CHF_2$, $—CHFCH_2F$, $—CH_2CHF_2$, $—CF_2CF_3$, $—CCl_3$, $—CH_2Cl$, $—CHCl_2$, 2,2,2-trifluoro-1,1-dimethyl-ethyl, and the like. Exemplary haloalkoxy groups include, but are not limited to: $—OCH_2F$, $—OCHF_2$, $—OCF_3$, and the like. The haloalkyl and haloalkoxy can be substituted at any available point of attachment, for example, with 1 to 5 substituents, 1 to 3 substituents or 1 substituent.

"$C_{3-7}$ cycloalkyl" refers to a radical of a non-aromatic cyclic hydrocarbon group having from 3 to 7 ring carbon atoms and zero heteroatoms. In some embodiments, $C_{3-5}$ cycloalkyl is alternative. In other embodiments, $C_{3-6}$ cycloalkyl is alternative. In other embodiments, $C_{5-6}$ cycloalkyl is alternative. The cycloalkyl also includes a ring system in which the cycloalkyl described herein is fused with one or more aryl or heteroaryl groups, wherein the point of attachment is on the cycloalkyl ring, and in such case, the number of carbon atoms continues to represent the number of carbon atoms in the cycloalkyl system. Exemplary cycloalkyl groups include, but are not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), etc. The cycloalkyl can be substituted with one or more substituents, for example, with 1 to 5 substituents, 1 to 3 substituents or 1 substituent.

"3- to 11-membered heterocyclyl" refers to a radical of 3- to 11-membered non-aromatic ring system having ring carbon atoms and 1 to 5 ring heteroatoms, wherein each of the heteroatoms is independently selected from nitrogen, oxygen, sulfur, boron, phosphorus and silicon. In the heterocyclyl containing one or more nitrogen atoms, the point of attachment can be a carbon or nitrogen atom as long as the valence permits. In some embodiments, 3- to 9-membered heterocyclyl is alternative, which is a radical of 3- to 9-membered non-aromatic ring system having ring carbon atoms and 1 to 5 ring heteroatoms. In some embodiments, 3- to 8-membered heterocyclyl is alternative, which is a radical of 3- to 8-membered non-aromatic ring system having ring carbon atoms and 1 to 4 ring heteroatoms; 3- to 6-membered heterocyclyl is alternative, which is a radical of 3- to 6-membered non-aromatic ring system having ring carbon atoms and 1 to 3 ring heteroatoms; 3- to 5-membered heterocyclyl is alternative, which is a radical of 3- to 5-membered non-aromatic ring system having ring carbon atoms and 1 to 2 ring heteroatoms; 4- to 8-membered heterocyclyl is alternative, which is a radical of 4- to 8-membered non-aromatic ring system having ring carbon atoms and 1 to 3 ring heteroatoms; 4- to 7-membered heterocyclyl is alternative, which is a radical of 4- to 7-membered non-aromatic ring system having ring carbon atoms and 1 to 3 ring heteroatoms; and 5- to 6-membered heterocyclyl is yet alternative, which is a radical of 5- to 6-membered non-aromatic ring system having ring carbon atoms and 1 to 3 ring heteroatoms. The heterocyclyl also includes a ring system wherein the heterocyclyl described above is fused with one or more cycloalkyl groups, wherein the point of attachment is on the cycloalkyl ring, or the heterocyclyl described above is fused with one or more aryl or heteroaryl groups, wherein the point of attachment is on the heterocyclyl ring; and in such cases, the number of ring members continues to represent the number of ring members in the heterocyclyl ring system. Exemplary 3-membered heterocyclyl groups containing one heteroatom include, but are not limited to, aziridinyl, oxiranyl and thiiranyl. Exemplary 4-membered heterocyclyl groups containing one heteroatom include, but are not limited to, azetidinyl, oxetanyl and thietanyl. Exemplary 5-membered heterocyclyl groups containing one heteroatom include, but are not limited to, tetrahydrofuranyl, dihydrofuranyl, tetrahydrothiophenyl, dihydrothienyl, pyrrolidinyl, dihydropyrrolyl and pyrrolyl-2,5-dione. Exemplary 5-membered heterocyclyl groups containing two heteroatoms include, but are not limited to, dioxolanyl, oxasulfuranyl, disulfuranyl, and oxazolidin-2-one. Exemplary 5-membered heterocyclyl groups containing three heteroatoms include, but are not limited to, triazolinyl, oxadiazolinyl, and thiadiazolinyl. Exemplary 6-membered heterocyclyl groups containing one heteroatom include, but are not limited to, piperidyl, tetrahydropyranyl, dihydropyridyl and thianyl. Exemplary 6-membered heterocyclyl groups containing two heteroatoms include, but are not limited to, piperazinyl, morpholinyl, dithianyl and dioxanyl. Exemplary 6-membered heterocyclyl groups containing three heteroatoms include, but are not limited to, triazinanyl. Exemplary 7-membered heterocycly groups containing one heteroatom include, but are not limited to, azepanyl, oxepanyl and thiepanyl. Exemplary 5-membered heterocyclyl groups fused with a $C_6$ aryl (also referred as 5,6-bicyclic heterocyclyl herein) include, but are not limited to, indolinyl, isoindolinyl, dihydrobenzofuranyl, dihydrobenzothiophenyl, benzoxazolinonyl, etc. Exemplary 6-membered heterocyclyl groups fused with a $C_6$ aryl (also referred as 6,6-bicyclic heterocyclyl herein) include, but are not limited to, tetrahydroquinolinyl, tetrahydroisoquinolinyl, etc. The heterocyclyl can be substituted with one or more substituents, for example, with 1 to 5 substituents, 1 to 3 substituents or 1 substituent.

"$C_{6-10}$ aryl" refers to a radical of monocyclic or polycyclic (e.g., bicyclic) 4n+2 aromatic ring system having 6-10 ring carbon atoms and zero heteroatoms (e.g., having 6 or 10 shared π electrons in a cyclic array). In some embodiments, the aryl group has six ring carbon atoms ("$C_6$ aryl"; for example, phenyl). In some embodiments, the aryl group has ten ring carbon atoms ("$C_{10}$ aryl"; for example, naphthyl, e.g., 1-naphthyl and 2-naphthyl). The aryl group also includes a ring system in which the aryl ring described above is fused with one or more cycloalkyl or heterocyclyl groups, and the point of attachment is on the aryl ring, in which case the number of carbon atoms continues to represent the number of carbon atoms in the aryl ring system. The aryl can be substituted with one or more substituents, for example, with 1 to 5 substituents, 1 to 3 substituents or 1 substituent.

"5- to 10-membered heteroaryl" refers to a radical of 5- to 10-membered monocyclic or bicyclic 4n+2 aromatic ring system (e.g., having 6 or 10 shared 11 electrons in a cyclic array) having ring carbon atoms and 1-4 ring heteroatoms, wherein each heteroatom is independently selected from nitrogen, oxygen and sulfur. In the heteroaryl group containing one or more nitrogen atoms, the point of attachment can be a carbon or nitrogen atom as long as the valence permits. Heteroaryl bicyclic systems may include one or more heteroatoms in one or two rings. Heteroaryl also includes ring systems wherein the heteroaryl ring described above is fused with one or more cycloalkyl or heterocyclyl groups, and the point of attachment is on the heteroaryl ring. In such case, the number the carbon atoms continues to represent the number of carbon atoms in the heteroaryl ring system. In some embodiments, 5- to 6-membered heteroaryl groups are yet alternative, which are radicals of 5- to 6-membered monocyclic or bicyclic 4n+2 aromatic ring systems having ring carbon atoms and 1-4 ring heteroatoms. Exemplary 5-membered heteroaryl groups containing one heteroatom include, but are not limited to, pyrrolyl, furyl and thienyl. Exemplary 5-membered heteroaryl groups containing two heteroatoms include, but are not limited to, imidazolyl, pyrazolyl, oxazolyl, isoxazolyl, thiazolyl, and isothiazolyl. Exemplary 5-membered heteroaryl groups containing three heteroatoms include, but are not limited to, triazolyl, oxadiazolyl (such as, 1,2,4-oxadiazoly), and thiadiazolyl. Exemplary 5-membered heteroaryl groups containing four heteroatoms include, but are not limited to, tetrazolyl. Exemplary 6-membered heteroaryl groups containing one heteroatom include, but are not limited to, pyridyl. Exemplary 6-membered heteroaryl groups containing two heteroatoms include, but are not limited to, pyridazinyl, pyrimidinyl, and pyrazinyl. Exemplary 6-membered heteroaryl groups containing three or four heteroatoms include, but are not limited to, triazinyl and tetrazinyl, respectively. Exemplary 7-membered heteroaryl groups containing one heteroatom include, but are not limited to, azepinyl, oxepinyl, and thiepinyl. Exemplary 5,6-bicyclic heteroaryl groups include, but are not limited to, indolyl, isoindolyl, indazolyl, benzotriazolyl, benzothiophenyl, isobenzothiophenyl, benzofuranyl, benzoisofuranyl, benzimidazolyl, benzoxazolyl, benzoisoxazolyl, benzoxadiazolyl, benzothiazolyl, benzoisothiazolyl, benzothiadiazolyl, indolizinyl and purinyl. Exemplary 6,6-bicyclic heteroaryl groups include, but are not limited to, naphthyridinyl, pteridinyl, quinolyl, isoquinolyl, cinnolinyl, quinoxalinyl, phthalazinyl and quinazolinyl. The heteroaryl can be substituted with one or more substituents, for example, with 1 to 5 substituents, 1 to 3 substituents or 1 substituent.

Specific examples of alternative heteroaryl groups include: pyrrolyl, imidazolyl, pyrazolyl, 2-pyridyl, 3-pyridyl, 4-pyridyl, pyrimidinyl, pyrazinyl, pyridazinyl, triazolyl (4H-1,2,4-triazolyl, 1H-1,2,3-triazolyl, 2H-1,2,3-triazolyl, pyranyl, 2-furyl, 3-furyl, 2-thienyl, 3-thienyl, oxazolyl, isoxazolyl, oxazolyl (1,2,4-oxazolyl, 1,3,4-oxazolyl, 1,2,5-oxazolyl, thiazolyl, thiadiazolyl (1,2,4-thiadiazolyl, 1,3,4-thiadiazolyl, 1,2,5-thiadiazolyl).

"Carbonyl", whether used alone or in conjunction with other terms (e.g., aminocarbonyl), is represented by —C(O)—.

"Oxo" represents =O.

"Thioxo" represents =S.

Alkyl, alkenyl, alkynyl, carbocyclyl, heterocyclyl, aryl and heteroaryl as defined herein are optionally substituted groups.

Exemplary substituents on carbon atoms include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$OSi(R^{aa})_3$, —$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)_2R^{aa}$, —$OP(=O)_2R^{aa}$, —$P(=O)(R^{aa})_2$, —$OP(=O)(R^{aa})_2$, —$OP(=O)(OR^{cc})_2$, —$P(=O)_2N(R^{bb})_2$, —$OP(=O)_2N(R^{bb})_2$, —$P(=O)(NR^{bb})_2$, —$OP(=O)(NR^{bb})_2$, —$NR^{bb}P(=O)(OR^{cc})_2$, —$NR^{bb}P(=O)(NR^{bb})_2$, —$P(R^{cc})_2$, —$P(R^{cc})_3$, —$OP(R^{cc})_2$, —$OP(R^{cc})_3$, —$B(R^{aa})_2$, —$B(OR^{cc})_2$, —$BR^{aa}(OR^{cc})$, alkyl, haloalkyl, alkenyl, alkynyl, carbocyclyl, heterocyclyl, aryl and heteroaryl, wherein each of the alkyl, alkenyl, alkynyl, carbocyclyl, heterocyclyl, aryl and heteroaryl is independently substituted with 0, 1, 2, 3, 4 or 5 $R^{dd}$ groups;

or two geminal hydrogens on a carbon atom are replaced with =O, =S, =$NN(R^{bb})_2$, =$NNR^{bb}C(=O)R^{aa}$, =$NNR^{bb}C(=O)OR^{aa}$, =$NNR^{bb}S(=O)_2R^{aa}$, =$NR^{bb}$ or =$NOR^{cc}$ groups;

each of the $R^{aa}$ is independently selected from alkyl, haloalkyl, alkenyl, alkynyl, carbocyclyl, heterocyclyl, aryl and heteroaryl, or two of the $R^{aa}$ groups are combined to form a heterocyclyl or heteroaryl ring, wherein each of the alkyl, alkenyl, alkynyl, carbocyclyl, heterocyclyl, aryl and heteroaryl is independently substituted with 0, 1, 2, 3, 4 or 5 Rad groups;

each of the $R^{bb}$ is independently selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)_2R^{aa}$, —$P(=O)(R^{aa})_2$, —$P(=O)_2N(R^{cc})_2$, —$P(=O)(NR^{cc})_2$, alkyl, haloalkyl, alkenyl, alkynyl, carbocyclyl, heterocyclyl, aryl and heteroaryl, or two $R^{bb}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 Rad groups;

each of the $R^{cc}$ is independently selected from hydrogen, alkyl, haloalkyl, alkenyl, alkynyl, carbocyclyl, heterocyclyl, aryl and heteroaryl, or two $R^{cc}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 $R^{dd}$ groups;

each of the Rad is independently selected from halogen, —CN, $—NO_2$, $—N_3$, $—SO_2H$, $—SO_3H$, —OH, $—OR^{ee}$, $—ON(R^{ff})_2$, $—N(R^{ff})_2$, $—N(R^{ff})_3{}^+X^-$, $—N(OR^{ee})R^{ff}$, —SH, $—SR^{ee}$, $—SSR^{ee}$, $—C(═O)R^{ee}$, $—CO_2H$, $—CO_2R^{ee}$, $—OC(═O)R^{ee}$, $—OCO_2R^{ee}$, $—C(═O)N(R^{ff})_2$, $—OC(═O)N(R^{ff})_2$, $—NR^{ff}C(═O)R^{ee}$, $—NR^{ff}CO_2R^{ee}$, $—NR^{ff}C(═O)N(R^{ff})_2$, $—C(═NR^{ff})OR^{ee}$, $—OC(═NR^{ff})R^{ee}$, $—OC(═NR^{ff})OR^{ee}$, $—C(═NR^{ff})N(R^{ff})_2$, $—OC(═NR^{ff})N(R^{ff})_2$, $—NR^{ff}C(═NR^{ff})N(R^{ff})_2$, $—NR^{ff}SO_2R^{ee}$, $—SO_2N(R^{ff})_2$, $—SO_2R^{ee}$, $—SO_2OR^{ee}$, $—OSO_2R^{ee}$, $—S(═O)R^{ee}$, $—Si(R^{ee})_3$, $—OSi(R^{ee})_3$, $—C(═S)N(R^{ff})_2$, $—C(═O)SR^{ee}$, $—C(═S)SR^{ee}$, $—SC(═S)SR^{ee}$, $—P(═O)_2R^{ee}$, $—P(═O)(R^{ee})_2$, $—OP(═O)(R^{ee})_2$—$OP(═O)(OR^{ee})_2$, alkyl, haloalkyl, alkenyl, alkynyl, carbocyclyl, heterocyclyl, aryl, and heteroaryl, wherein each of the alkyl, alkenyl, alkynyl, carbocyclyl, heterocyclyl, aryl and heteroaryl is independently substituted with 0, 1, 2, 3, 4 or 5 $R^{gg}$ groups, or two geminal $R^{dd}$ substituents can be combined to form ═O or ═S;

each of the $R^{ee}$ is independently selected from alkyl, haloalkyl, alkenyl, alkynyl, carbocyclyl, aryl, heterocyclyl, and heteroaryl, wherein each of the alkyl, alkenyl, alkynyl, carbocyclyl, heterocyclyl, aryl and heteroaryl is independently substituted with 0, 1, 2, 3, 4 or 5 $R^{gg}$ groups;

each of the $R^{ff}$ is independently selected from hydrogen, alkyl, haloalkyl, alkenyl, alkynyl, carbocyclyl, heterocyclyl, aryl and heteroaryl, or two $R^{ff}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 $R^{gg}$ groups;

each of the $R^{gg}$ is independently selected from halogen, —CN, $—NO_2$, $—N_3$, $—SO_2H$, $—SO_3H$, —OH, $—OC_{1-6}$ alkyl, $—ON(C_{1-6}$ alkyl$)_2$, $—N(C_{1-6}$ alkyl$)_2$, $—N(C_{1-6}$ alkyl$)_3{}^+X^-$, $—NH(C_{1-6}$ alkyl$)_2{}^+X^-$, $—NH_2(C_{1-6}$ alkyl$)^+X^-$, $—NH_3{}^+X^-$, $—N(OC_{1-6}$ alkyl$)(C_{1-6}$ alkyl), $—N(OH)(C_{1-6}$ alkyl), —NH(OH), —SH, $—SC_{1-6}$ alkyl, $—SS(C_{1-6}$ alkyl), $—C(═O)(C_{1-6}$ alkyl), $—CO_2H$, $—CO_2(C_{1-6}$ alkyl), $—OC(═O)(C_{1-6}$ alkyl), $—OCO_2(C_{1-6}$ alkyl), $—C(═O)NH_2$, $—C(═O)N(C_{1-6}$ alkyl$)_2$, $—OC(═O)NH(C_{1-6}$ alkyl), $—NHC(═O)(C_{1-6}$ alkyl), $—N(C_{1-6}$ alkyl$)C(═O)(C_{1-6}$ alkyl), $—NHCO_2(C_{1-6}$ alkyl), $—NHC(═O)N(C_{1-6}$ alkyl$)_2$, $—NHC(═O)NH(C_{1-6}$ alkyl), $—NHC(═O)NH_2$, $—C(═NH)O(C_{1-6}$ alkyl), $—OC(═NH)(C_{1-6}$ alkyl), $—OC(═NH)OC_{1-6}$ alkyl, $—C(═NH)N(C_{1-6}$ alkyl$)_2$, $—C(═NH)NH(C_{1-6}$ alkyl), $—C(═NH)NH_2$, $—OC(═NH)N(C_{1-6}$ alkyl$)_2$, $—OC(NH)NH(C_{1-6}$ alkyl), $—OC(NH)NH_2$, $—NHC(NH)N(C_{1-6}$ alkyl$)_2$, $—NHC(═NH)NH_2$, $—NHSO_2(C_{1-6}$ alkyl), $—SO_2N(C_{1-6}$ alkyl$)_2$, $—SO_2NH(C_{1-6}$ alkyl), $—SO_2NH_2$, $—SO_2C_{1-6}$ alkyl, $—SO_2OC_{1-6}$ alkyl, $—OSO_2C_{1-6}$ alkyl, $—SOC_{1-6}$ alkyl, $—Si(C_{1-6}$ alkyl$)_3$, $—OSi(C_{1-6}$ alkyl$)_3$, $—C(═S)N(C_{1-6}$ alkyl$)_2$, $C(═S)NH(C_{1-6}$ alkyl), $C(═S)NH_2$, $—C(═O)S(C_{1-6}$ alkyl), $—C(═S)SC_{1-6}$ alkyl, $—SC(═S)SC_{1-6}$ alkyl, $—P(═O)_2(C_{1-6}$ alkyl), $—P(═O)(C_{1-6}$ alkyl$)_2$, $—OP(═O)(C_{1-6}$ alkyl$)_2$, $—OP(═O)(OC_{1-6}$ alkyl$)_2$, $C_{1-6}$ alkyl, $C_{1-6}$ haloalkyl, $C_2$-$C_6$ alkenyl, $C_2$-$C_6$ alkynyl, $C_3$-$C_7$ carbocyclyl, $C_6$-$C_{10}$ aryl, $C_3$-$C_7$ heterocyclyl, and $C_5$-$C_{10}$ heteroaryl; or two geminal $R^{gg}$ substituents may combine to form ═O or ═S; wherein $X^-$ is a counter-ion.

Exemplary substituents on nitrogen atoms include, but are not limited to, hydrogen, —OH, $—OR^{aa}$, $—N(R^{cc})_2$, —CN, $—C(═O)R^{aa}$, $—C(═O)N(R^{cc})_2$, $—CO_2R^{aa}$, $—SO_2R^{aa}$, $—C(═NR^{bb})R^{aa}$, $—C(═NR^{cc})OR^{aa}$, $—C(═NR^{cc})N(R^{cc})_2$, $—SO_2N(R^{cc})_2$, $—SO_2R^{cc}$, $—SO_2OR^{cc}$, $—SOR^{aa}$, $—C(═S)N(R^{cc})_2$, $—C(═O)SR^{cc}$, $—C(═S)SR^{cc}$, $—P(═O)_2R^{aa}$, $—P(═O)(R^{aa})_2$, $—P(═O)_2N(R^{cc})_2$, $—P(═O)(NR^{cc})_2$, alkyl, haloalkyl, alkenyl, alkynyl, carbocyclyl, heterocyclyl, aryl and heteroaryl, or two $R^{cc}$ groups attached to a nitrogen atom combine to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 $R^{dd}$ groups, and wherein $R^{aa}$, $R^{bb}$, $R^{cc}$ and $R^{dd}$ are as described herein.

Other Definitions

The term "cancer" includes, but is not limited to, the cancers of: breast, ovary, cervix, prostate, testis, esophagus, stomach, skin, lung, bone, colon, pancreas, thyroid, biliary tract, buccal cavity and pharynx (mouth), lips, tongue, oral cavity, pharynx, small intestine, colorectal, large intestine, rectum, cancer of brain and central nervous system, glioblastoma, neuroblastoma, keratoacanthoma, epidermoid carcinoma, large cell carcinoma, adenocarcinoma, adenoma, follicular carcinoma, undifferentiated carcinoma, papillary carcinoma, seminoma, melanoma, sarcoma, bladder cancer, liver cancer, kidney cancer, bone marrow disorder, lymphatic disorder, Hodgkin's disease, hairy cell carcinoma and leukemia.

The term "treating" as used herein relates to reversing, alleviating or inhibiting the progression or prevention of the disorders or conditions to which the term applies, or of one or more symptoms of such disorders or conditions. The noun "treatment" as used herein relates to the action of treating, which is a verb, and the latter is as just defined.

The term "pharmaceutically acceptable salt" as used herein refers to those carboxylate and amino acid addition salts of the compounds of the present disclosure, which are suitable for the contact with patients' tissues within a reliable medical judgment, and do not produce inappropriate toxicity, irritation, allergy, etc. They are commensurate with a reasonable benefit/risk ratio, and are effective for their intended use. The term includes, if possible, the zwitterionic form of the compounds of the disclosure.

The pharmaceutically acceptable base addition salts are formed with metals or amines, such as alkali metal and alkaline earth metal hydroxides or organic amines. Examples of the metals used as cations include sodium, potassium, magnesium, calcium, etc. Examples of suitable amines are N,N'-dibenzylethylenediamine, chloroprocaine, choline, diethanolamine, ethylenediamine, N-methylglucamine and procaine.

The base addition salt of the acidic compound can be prepared by contacting the free acid form with a sufficient amount of the required base to form a salt in a conventional manner. The free acid can be regenerated by contacting the salt form with an acid in a conventional manner and then isolating the free acid. The free acid forms are somewhat different from their respective salt forms in their physical properties, such as solubility in polar solvents. But for the purposes of the present disclosure, the salts are still equivalent to their respective free acids.

The salts can be prepared from the inorganic acids, which include sulfates, pyrosulfates, bisulfates, sulfites, bisulfites, nitrates, phosphates, monohydrogen phosphates, dihydrogen phosphates, metaphosphates, pyrophosphates, chlorides, bromides and iodides. Examples of the acids include hydrochloric acid, nitric acid, sulfuric acid, hydrobromic acid, hydroiodic acid, phosphoric acid, etc. The representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthalate, methanesulfonate, glucoheptanate, lactobionate, lauryl sulfonate, isethionate, etc. The salts can also be prepared from the organic acids, which include aliphatic monocarboxylic and dicarboxylic acids, phenyl-substituted alkanoic acids, hydroxyalkanoic acids, alkanedioic acid, aromatic acids, aliphatic and aromatic sulfonic acids, etc. The representative salts include acetate, propionate, octanoate, isobutyrate, oxalate, malonate, succinate, suberate, sebacate, fumarate, maleate, mandelate, benzoate, chlorobenzoate, methyl benzoate, dinitrobenzoate, naphthoate, besylate, tosylate, phenylacetate, citrate, lactate, maleate, tartrate, methanesulfonate, etc. The pharmaceutically acceptable salts can include cations based on alkali metals and alkaline earth metals, such as sodium, lithium, potassium, calcium, magnesium, etc., as well as non-toxic ammonium, quaternary ammonium, and amine cations including, but not limited to, ammonium, tetramethylammonium, tetraethylammonium, methylamine, dimethylamine, trimethylamine, triethylamine, ethylamine, etc. Salts of amino acids are also included, such as arginine salts, gluconates, galacturonates, etc. (for example, see Berge S. M. et al., "Pharmaceutical Salts," J. Pharm. Sci., 1977; 66: 1-19 for reference).

Examples of pharmaceutically acceptable non-toxic amides of the compounds of the disclosure include $C_1$-$C_6$ alkyl esters, wherein the alkyl group is straight or branched. Acceptable esters also include $C_5$-$C_7$ cycloalkyl esters as well as arylalkyl esters, such as, but not limited to, benzyl esters. $C_1$-$C_4$ alkyl esters are alternative. Esters of the compounds of the disclosure can be prepared according to the conventional methods, for example, March's Advanced Organic Chemistry, 5 Edition, M. B. Smith & J. March, John Wiley & Sons, 2001.

Examples of pharmaceutically acceptable non-toxic amides of the compounds of the disclosure include amides derived from ammonia, primary $C_1$-$C_6$ alkylamines and secondary $C_1$-$C_6$ dialkylamines, wherein the alkyl group is straight or branched. In the case of the secondary amine, the amine may also be in the form of a 5- or 6-membered heterocycle containing one nitrogen atom. Amides derived from ammonia, $C_1$-$C_3$ alkyl primary amine and $C_1$-$C_2$ dialkyl secondary amine are alternative. Amides of the compounds of the present disclosure can be prepared according to the conventional methods, for example, March's Advanced Organic Chemistry, 5 Edition, M. B. Smith & J. March, John Wiley & Sons, 2001.

"Subjects" to which administration is contemplated include, but are not limited to, humans (e.g., males or females of any age group, e.g., paediatric subjects (e.g., infants, children, adolescents) or adult subjects (e.g., young adults, middle-aged adults or older adults) and/or non-human animals, such as mammals, e.g., primates (e.g., cynomolgus monkeys, rhesus monkeys), cattle, pigs, horses, sheep, goats, rodents, cats and/or dogs. In some embodiments, the subject is a human. In some embodiments, the subject is a non-human animal. The terms "human", "patient" and "subject" can be used interchangeably herein.

"Disease", "disorder", and "condition" can be used interchangeably herein.

Unless otherwise indicated, the term "treatment" as used herein includes the effect on a subject who is suffering from a particular disease, disorder, or condition, which reduces the severity of the disease, disorder, or condition, or delays or slows the progression of the disease, disorder or condition ("therapeutic treatment"). The term also includes the effect that occurs before the subject begins to suffer from a specific disease, disorder or condition ("prophylactic treatment").

Generally, the "effective amount" of a compound refers to an amount sufficient to elicit a target biological response. As understood by those skilled in the art, the effective amount of the compound of the disclosure can vary depending on the following factors, such as the desired biological endpoint, the pharmacokinetics of the compound, the diseases being treated, the mode of administration, and the age, health status and symptoms of the subjects. The effective amount includes therapeutically effective amount and prophylactically effective amount.

Unless otherwise indicated, the "therapeutically effective amount" of the compound as used herein is an amount sufficient to provide therapeutic benefits in the course of treating a disease, disorder or condition, or to delay or minimize one or more symptoms associated with the disease, disorder or condition. The therapeutically effective amount of a compound refers to the amount of the therapeutic agent that, when used alone or in combination with other therapies, provides a therapeutic benefit in the treatment of a disease, disorder or condition. The term "therapeutically effective amount" can include an amount that improves the overall treatment, reduces or avoids the symptoms or causes of the disease or condition, or enhances the therapeutic effect of other therapeutic agents.

Unless otherwise indicated, the "prophylactically effective amount" of the compound as used herein is an amount sufficient to prevent a disease, disorder or condition, or an amount sufficient to prevent one or more symptoms associated with a disease, disorder or condition, or an amount sufficient to prevent the recurrence of a disease, disorder or condition. The prophylactically effective amount of a compound refers to the amount of a therapeutic agent that, when used alone or in combination with other agents, provides a prophylactic benefit in the prevention of a disease, disorder or condition. The term "prophylactically effective amount" can include an amount that improves the overall prevention, or an amount that enhances the prophylactic effect of other preventive agents.

"Combination" and related terms refer to the simultaneous or sequential administration of the compounds of the present disclosure and other therapeutic agents. For example, the compounds of the present disclosure can be administered simultaneously or sequentially in separate unit dosage with other therapeutic agents, or simultaneously in a single unit dosage with other therapeutic agents.

DETAILED DESCRIPTION OF THE INVENTION

As used herein, the term "compound disclosed herein" or "compound of the present disclosure" refers to the following compounds of formulae (I) to (III) (including sub-formulae, such as (I-1), (II-2), (III-3), etc.), or pharmaceutically acceptable salts, enantiomers, diastereomers, racemates, solvates, hydrates, polymorphs, prodrugs, or isotopic variants thereof, or mixtures thereof.

In the present disclosure, compounds are named using standard nomenclature. For compounds having an asymmetric center, it should be understood, unless otherwise stated, that all optical isomers and mixtures thereof are included. Furthermore, unless otherwise specified, all isomer compounds and carbon-carbon double bonds included in the present disclosure may occur in the form of Z and E. For compounds which exist in different tautomeric forms, one of the compounds is not limited to any particular tautomer, but is intended to cover all tautomeric forms. General formula is used for certain compounds, including descriptions and variables.

Unless otherwise specified, each variable in such a formula is defined independently of any other variable and multiple variables that independently define any one of the variables in each occurrence.

In one embodiment, the present disclosure relates to a compound of general formula (I), or a pharmaceutically acceptable salt, enantiomer, diastereomer, racemate, solvate, hydrate, polymorph, prodrug, or isotopic variant thereof, or a mixture thereof.

(I)

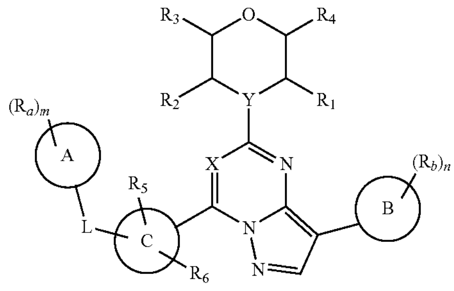

wherein

X is $CR_X$ or N;

Y is $CR_Y$ or N;

$R_1$, $R_2$, $R_3$, $R_4$ and $R_Y$ are independently selected from H, D, halogen, $C_{1-6}$ alkyl, $C_{2-6}$ alkenyl and $C_{2-6}$ alkynyl, or $R_1$ and $R_2$, $R_3$ and $R_4$ are connected to form bond, $C_{1-6}$ alkylene, $C_{2-6}$ alkenylene or $C_{2-6}$ alkynylene; wherein the groups may be substituted by one or more D or halogens up to fully substituted;

wherein $R_X$ is H, D, halogen, —CN, —NRR', —OR, —SR or $C_{1-6}$ alkyl, wherein the groups may be substituted by one or more D or halogens up to fully substituted;

when Y is $CR_Y$, $R_Y$ and $R_1$ are taken together with the atoms to which they are attached to form $C_{3-5}$ cycloalkyl or 3- to 5-membered heterocyclyl, wherein the groups may be substituted by one or more D or halogens up to fully substituted;

ring A is $C_{3-7}$ cycloalkyl, 4- to 7-membered heterocyclyl, $C_{6-10}$ aryl or 5- to 10-membered heteroaryl; or ring A is absent, so one $R_a$ is connected to L; or even $(R_a)_m$-ring A-L- is absent;

$R_a$ is independently selected from H, D, halogen, —CN, —NRR', —OR, —SR, —C(O)R, —C(O)OR, —C(O)NRR', —OC(O)R', —NRC(O)R', —OC(O)NRR', —NRC(O)NRR', —$S(O)_pR$, $C_{1-6}$ alkyl, $C_{2-6}$ alkenyl, $C_{2-6}$ alkynyl, $C_{3-7}$ cycloalkyl and 3- to 8-membered heterocyclyl, each of which is optionally substituted with R*, wherein the groups may be substituted by one or more D or halogens up to fully substituted;

m is 0, 1, 2, 3, 4 or 5;

ring B is 5- to 6-membered heteroaryl;

$R_b$ is independently selected from H, D, halogen, —CN, —NRR', —OR, —SR, —C(O)R, —C(O)OR, —C(O)NRR', —OC(O)R', —NRC(O)R', —OC(O)NRR', —NRC(O)NRR', —$S(O)_pR$, $C_{1-6}$ alkyl, $C_{2-6}$ alkenyl, $C_{2-6}$ alkynyl, $C_{3-7}$ cycloalkyl and 3- to 8-membered heterocyclyl, each of which is optionally substituted with R*, wherein the groups may be substituted by one or more D or halogens up to fully substituted;

n is 0,1,2,3,4 or 5;

ring C is $C_{3-7}$ cycloalkyl, 4- to 7-membered heterocyclyl, $C_{6-10}$ aryl or 5- to 10-membered heteroaryl;

L is a bond, —O—, —S—, —N(R)—, —C(O)—, $C_{1-6}$ alkylene, $C_{2-6}$ alkenylene or $C_{2-6}$ alkynylene;

$R_5$ is H, D, halogen, —CN, —NRR', —OR, —SR, $C_{1-6}$ alkyl, $C_{2-6}$ alkenyl or $C_{2-6}$ alkynyl, wherein the groups may be substituted by one or more D or halogens up to fully substituted;

$R_6$ is H, D, halogen, —CN, —NRR', —OR, —SR, $C_{1-6}$ alkyl, $C_{2-6}$ alkenyl or $C_{2-6}$ alkynyl, wherein the groups may be substituted by one or more D or halogens up to fully substituted;

R* is H, halogen, —CN, —NRR', —OR, —SR, —C(O)R, —C(O)OR, —C(O)NRR', —OC(O)R', —NRC(O)R', —OC(O)NRR', —NRC(O)NRR', —$S(O)_pR$, $C_{3-7}$ cycloalkyl, 3- to 8-membered heterocyclyl, $C_{6-10}$ aryl or 5- to 10-membered heteroaryl, wherein the groups may be substituted by one or more D or halogens up to fully substituted;

R and R' are independently selected from H, $C_{1-6}$ alkyl, $C_{2-6}$ alkenyl and $C_{2-6}$ alkynyl, or R and R' are taken together with the nitrogen atom to which they are attached to form 4- to 8-membered heterocyclyl; wherein the groups may be substituted by one or more D or halogens up to fully substituted;

p is 1 or 2.

X and Y

In a specific embodiment, X is $CR_X$; in another specific embodiment, X is CH; in another specific embodiment, X is N.

In a specific embodiment, Y is $CR_Y$; in another specific embodiment, Y is N.

$R_1$, $R_2$, $R_3$, $R_4$ and $R_Y$

In a specific embodiment, $R_1$ is H; in another specific embodiment, $R_1$ is D; in another specific embodiment, $R_1$ is halogen; in another specific embodiment, $R_1$ is $C_{1-6}$ alkyl, such as (R)—$C_{1-6}$ alkyl, such as (R)-methyl; in another specific embodiment, $R_1$ is $C_{1-6}$ haloalkyl, such as (R)—$C_{1-6}$ haloalkyl; in another specific embodiment, $R_1$ is $C_{2-6}$ alkenyl; in another specific embodiment, $R_1$ is $C_{2-6}$ alkynyl.

In a specific embodiment, $R_2$ is H; in another specific embodiment, $R_2$ is D; in another specific embodiment, $R_2$ is halogen; in another specific embodiment, $R_2$ is $C_{1-6}$ alkyl, such as (R)—$C_{1-6}$ alkyl, such as (R)-methyl; in another specific embodiment, $R_2$ is $C_{1-6}$ haloalkyl, such as (R)—$C_{1-6}$ haloalkyl; in another specific embodiment, $R_2$ is $C_{2-6}$ alkenyl; in another specific embodiment, $R_2$ is $C_{2-6}$ alkynyl.

In a specific embodiment, $R_3$ is H; in another specific embodiment, $R_3$ is D; in another specific embodiment, $R_3$ is halogen; in another specific embodiment, $R_3$ is $C_{1-6}$ alkyl, such as (R)—$C_{1-6}$ alkyl, such as (R)-methyl; in another specific embodiment, $R_3$ is $C_{1-6}$ haloalkyl, such as (R)—$C_{1-6}$ haloalkyl; in another specific embodiment, $R_3$ is $C_{2-6}$ alkenyl; in another specific embodiment, $R_3$ is $C_{2-6}$ alkynyl.

In a specific embodiment, $R_4$ is H; in another specific embodiment, $R_4$ is D; in another specific embodiment, $R_4$ is halogen; in another specific embodiment, $R_4$ is $C_{1-6}$ alkyl, such as (R)—$C_{1-6}$ alkyl, such as (R)-methyl; in another specific embodiment, $R_4$ is $C_{1-6}$ haloalkyl, such as (R)—$C_{1-6}$ haloalkyl; in another specific embodiment, $R_4$ is $C_{2-6}$ alkenyl; in another specific embodiment, $R_4$ is $C_{2-6}$ alkynyl.

In a specific embodiment, $R_Y$ is H; in another specific embodiment, $R_Y$ is D; in another specific embodiment, $R_Y$ is halogen; in another specific embodiment, $R_Y$ is $C_{1-6}$ alkyl, such as (R)—$C_{1-6}$ alkyl, such as (R)-methyl; in another specific embodiment, $R_Y$ is $C_{1-6}$ haloalkyl, such as (R)—$C_{1-6}$ haloalkyl; in another specific embodiment, $R_Y$ is $C_{2-6}$ alkenyl; in another specific embodiment, $R_Y$ is $C_{2-6}$ alkynyl.

In another specific embodiment, at least one of $R_1$ and $R_2$ is $C_{1-6}$ alkyl, such as (R)—$C_{1-6}$ alkyl, such as (R)-methyl.

In another specific embodiment, $R_1$ and $R_2$, or $R_3$ and $R_4$ are connected to form bond; in another specific embodiment, $R_1$ and $R_2$, or $R_3$ and $R_4$ are connected to form $C_{1-6}$ alkylene, such as methylene, ethylene or propylene; in another specific embodiment, $R_1$ and $R_2$, or $R_3$ and $R_4$ are connected to form $C_{2-6}$ alkenylene; in another specific embodiment, $R_1$ and $R_2$, or $R_3$ and $R_4$ are connected to form $C_{2-6}$ alkynylene.

In another specific embodiment, the above groups may be substituted by one or more D or halogens up to fully substituted.

In another specific embodiment, when Y is $CR_Y$, $R_Y$ and $R_1$ are taken together with the atoms to which they are attached to form $C_{3-5}$ cycloalkyl; in another specific embodiment, the $C_{3-5}$ cycloalkyl is cyclopropyl; in another specific embodiment, the $C_{3-5}$ cycloalkyl is cyclobutyl; in another specific embodiment, the $C_{3-5}$ cycloalkyl is cyclopentyl; in another specific embodiment, when Y is $CR_Y$, $R_Y$ and $R_1$ are taken together with the atoms to which they are attached to form 3- to 5-membered heterocyclyl; in another specific embodiment, the 3- to 5-membered heterocyclyl is oxiranyl, aziridinyl or thiiranyl; in another specific embodiment, the 3- to 5-membered heterocyclyl is oxetanyl, azetidinyl or thietanyl; in another specific embodiment, the 3- to 5-membered heterocyclyl is tetrahydrofuranyl, pyrrolidinyl or thiolanyl. In another specific embodiment, the $C_{3-5}$ cycloalkyl and 3- to 5-membered heterocyclyl may be substituted by one or more D or halogens up to fully substituted.

Ring A

In a specific embodiment, ring A is absent; In another specific embodiment, ring A is $C_{3-7}$ cycloalkyl; In another specific embodiment, ring A is 4- to 7-membered heterocyclyl; In another specific embodiment, ring A is $C_{6-10}$ aryl; In another specific embodiment, ring A is 5- to 10-membered heteroaryl.

In another specific embodiment, ring A is 5- to 6-membered heteroaryl. In another specific embodiment, ring A is 4- to 7-membered heterocyclyl, alternatively selected from piperazinyl and piperidinyl.

In another specific embodiment, ring A is selected from

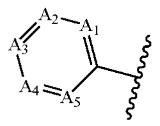,
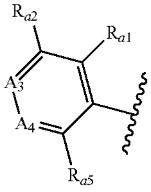,

-continued

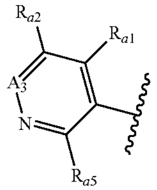
and
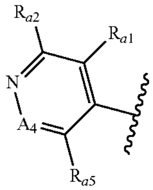, wherein $A_1$ is $CR_{a1}$ or N; $A_2$ is $CR_{a2}$ or N; $A_3$ is $CR_{a3}$ or N; $A_4$ is $CR_{a4}$ or N; $A_5$ is $CR_{a5}$ or N; $R_{a1}$, $R_{a2}$, $R_{a3}$, $R_{a4}$ and $R_{a5}$ are as defined above for $R_a$.

In another specific embodiment, $(R_a)_m$-ring A-L- is selected from

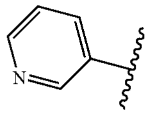,
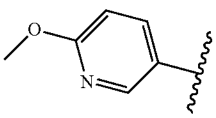,
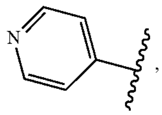,
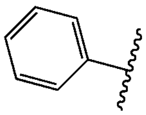,
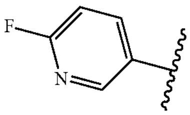,
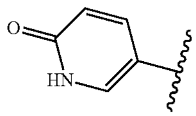,
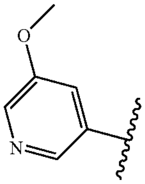,
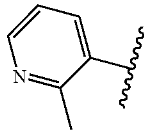,
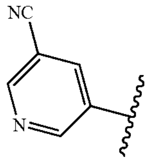,
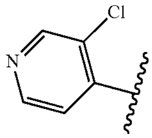,
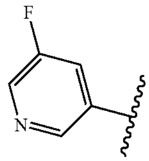,
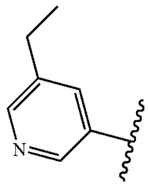,
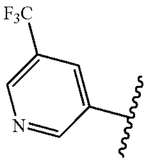,
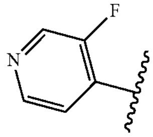,
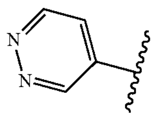,
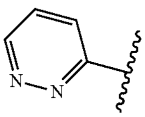,
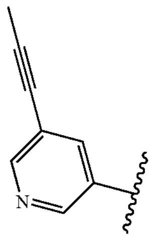,
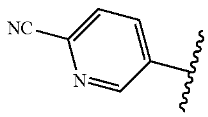,
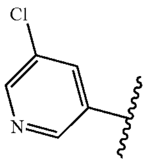, -continued

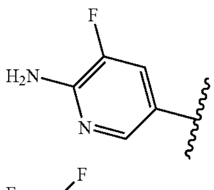,
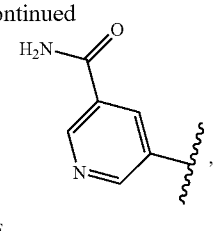,
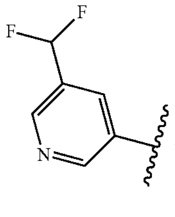,
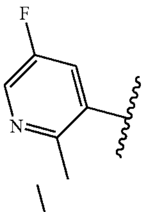,
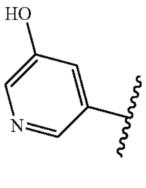,
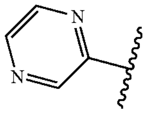
and
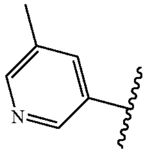.

$R_a$

In a specific embodiment, $R_a$ is independently selected from H, D, halogen, —CN, —NRR', —OR, —SR, —C(O)R, —C(O)OR, —C(O)NRR', —OC(O)R', —NRC(O)R', —OC(O)NRR', —NRC(O)NRR', —$S(O)_pR$, $C_{1-6}$ alkyl, $C_{2-6}$ alkenyl, $C_{2-6}$ alkynyl, $C_{3-7}$ cycloalkyl and 3- to 8-membered heterocyclyl, each of which is optionally substituted with R*, wherein the groups may be substituted by one or more D or halogens up to fully substituted; in another specific embodiment, one of $R_a$ is H; in another specific embodiment, one of $R_a$ is D; in another specific embodiment, one of $R_a$ is halogen; in another specific embodiment, one of $R_a$ is —CN; in another specific embodiment, one of $R_a$ is —NRR'; in another specific embodiment, one of $R_a$ is —OR; in another specific embodiment, one of $R_a$ is —SR; in another specific embodiment, one of $R_a$ is —C(O)R; in another specific embodiment, one of $R_a$ is —C(O)OR; in another specific embodiment, one of $R_a$ is —C(O)NRR'; in another specific embodiment, one of $R_a$ is —OC(O)R'; in another specific embodiment, one of $R_a$ is —NRC(O)R'; in another specific embodiment, one of $R_a$ is —OC(O)NRR'; in another specific embodiment, one of $R_a$ is —NRC(O)NRR'; in another specific embodiment, one of $R_a$ is —$S(O)_pR$; in another specific embodiment, one of $R_a$ is $C_{1-6}$ alkyl; in another specific embodiment, one of $R_a$ is $C_{2-6}$ alkenyl; in another specific embodiment, one of $R_a$ is $C_{2-6}$ alkynyl; in another specific embodiment, one of $R_a$ is $C_3$-7 cycloalkyl; in another specific embodiment, one of $R_a$ is 3- to 8-membered heterocyclyl; in another specific embodiment, one of $R_a$ is substituted by one, two or three R*; in another specific embodiment, the groups may be substituted by one or more D or halogens up to fully substituted.

In another specific embodiment, $R_a$ is independently selected from H, D, halogen, —CN, —NRR', —OR, —SR, —C(O)R, —C(O)OR, —C(O)NRR', $C_{1-6}$ alkyl, $C_{1-6}$ haloalkyl, $C_{2-6}$ alkenyl and $C_{2-6}$ alkynyl, wherein the groups may be substituted by one or more D up to fully deuterated.

m

In a specific embodiment, m is 0; in another specific embodiment, m is 1; in another specific embodiment, m is 2; in another specific embodiment, m is 3; in another specific embodiment, m is 4; in another specific embodiment, m is 5.

Ring B

In a specific embodiment, ring B is 5- to 6-membered heteroaryl, for example pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrrolyl, furanyl, thienyl, pyrazolyl or pyridyl; alternatively pyrazolyl.

$R_b$

In a specific embodiment, $R_b$ is independently selected from H, D, halogen, —CN, —NRR', —OR, —SR, —C(O)R, —C(O)OR, —C(O)NRR', —OC(O)R', —NRC(O)R', —OC(O)NRR', —NRC(O)NRR', —$S(O)_pR$, $C_{1-6}$ alkyl, $C_{2-6}$ alkenyl, $C_{2-6}$ alkynyl, $C_3$-7 cycloalkyl and 3- to 8-membered heterocyclyl, each of which is optionally substituted with R*, wherein the groups may be substituted by one or more D or halogens up to fully substituted; in another specific embodiment, one of $R_b$ is H; in another specific embodiment, one of $R_b$ is D; in another specific embodiment, one of $R_b$ is halogen; in another specific embodiment, one of $R_b$ is —CN; in another specific embodiment, one of $R_b$ is —NRR'; in another specific embodiment, one of $R_b$ is —OR; in another specific embodiment, one of $R_b$ is —SR; in another specific embodiment, one of $R_b$ is —C(O)R; in another specific embodiment, one of $R_b$ is —C(O)OR; in another specific embodiment, one of $R_b$ is —C(O)NRR'; in another specific embodiment, one of $R_b$ is —OC(O)R'; in another specific embodiment, one of $R_b$ is —NRC(O)R'; in another specific embodiment, one of $R_b$ is —OC(O)NRR'; in another specific embodiment, one of $R_b$ is —NRC(O)NRR'; in another specific embodiment, one of $R_b$ is —$S(O)_pR$; in another specific embodiment, one of $R_b$ is $C_{1-6}$ alkyl; in another specific embodiment, one of $R_b$ is $C_{2-6}$ alkenyl; in another specific embodiment, one of $R_b$ is $C_{2-6}$ alkynyl; in another specific embodiment, one of $R_b$ is $C_{3-7}$ cycloalkyl; in another specific embodiment, one of $R_b$ is 3- to 8-membered heterocyclyl; in another specific embodiment, one of $R_b$ is substituted by one, two or three R*; in another specific embodiment, the groups may be substituted by one or more D or halogens up to fully substituted.

In another specific embodiment, $R_b$ is independently selected from H, D, halogen, —CN, —NRR', —OR, —SR, $C_{1-6}$ alkyl and $C_{1-6}$ haloalkyl, each of which is optionally substituted with R*.

n

In a specific embodiment, n is 0; in another specific embodiment, n is 1; in another specific embodiment, n is 2; in another specific embodiment, n is 3; in another specific embodiment, n is 4; in another specific embodiment, n is 5.

Ring C

In a specific embodiment, ring C is $C_{3-7}$ cycloalkyl; In another specific embodiment, ring C is 4- to 7-membered heterocyclyl; In another specific embodiment, ring C is $C_{6-10}$ aryl; In another specific embodiment, ring C is 5- to 10-membered heteroaryl.

In another specific embodiment, ring C is 5- to 6-membered heteroaryl or phenyl; alternatively pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrazolyl, oxazolyl, isoxazolyl, thiazolyl, isothiazolyl or triazolyl; alternatively pyrazolyl.

In another specific embodiment, ring C is $C_{3-7}$ cycloalkyl or 4- to 7-membered heterocyclyl, alternatively cyclopentyl or tetrahydropyranyl.

L

In a specific embodiment, L is a bond; In another specific embodiment, L is —O—; In another specific embodiment, L is —S—; In another specific embodiment, L is —N(R)—; In another specific embodiment, L is —C(O)—; In another specific embodiment, L is $C_{1-6}$ alkylene; In another specific embodiment, L is $C_{2-6}$ alkenylene; In another specific embodiment, L is $C_{2-6}$ alkynylene.

In another specific embodiment, L is a bond, —C(O)— or $C_{1-6}$ alkylene.

$R_5$

In a specific embodiment, $R_5$ is H; in another specific embodiment, $R_5$ is D; in another specific embodiment, $R_5$ is halogen; in another specific embodiment, $R_5$ is —CN; in another specific embodiment, $R_5$ is —NRR'; in another specific embodiment, $R_5$ is —OR; in another specific embodiment, $R_5$ is —SR; in another specific embodiment, $R_5$ is $C_{1-6}$ alkyl; in another specific embodiment, $R_5$ is $C_{2-6}$ alkenyl; in another specific embodiment, $R_5$ is $C_{2-6}$ alkynyl; in another specific embodiment, $R_5$ may be substituted by one or more D or halogens up to fully substituted.

$R_6$

In a specific embodiment, $R_6$ is H; in another specific embodiment, $R_6$ is D; in another specific embodiment, $R_6$ is halogen; in another specific embodiment, $R_6$ is —CN; in another specific embodiment, $R_6$ is —NRR'; in another specific embodiment, $R_6$ is —OR; in another specific embodiment, $R_6$ is —SR; in another specific embodiment, $R_6$ is $C_{1-6}$ alkyl; in another specific embodiment, $R_6$ is $C_{2-6}$ alkenyl; in another specific embodiment, $R_6$ is $C_{2-6}$ alkynyl; in another specific embodiment, $R_6$ may be substituted by one or more D or halogens up to fully substituted.

R*

In a specific embodiment, R* is H; in another specific embodiment, R* is halogen; in another specific embodiment, R* is —CN; in another specific embodiment, R* is —NRR'; in another specific embodiment, R* is —OR; in another specific embodiment, R* is —SR; in another specific embodiment, R* is —C(O)R; in another specific embodiment, R* is —C(O)OR; in another specific embodiment, R* is —C(O)NRR'; in another specific embodiment, R* is —OC(O)R'; in another specific embodiment, R* is —NRC(O)R'; in another specific embodiment, R* is —OC(O)NRR'; in another specific embodiment, R* is —NRC(O)NRR'; in another specific embodiment, R* is —$S(O)_pR$; in another specific embodiment, R* is $C_{3-7}$ cycloalkyl; in another specific embodiment, R* is 3- to 8-membered heterocyclyl; in another specific embodiment, R* is $C_{6-10}$ aryl; in another specific embodiment, R* is 5- to 10-membered heteroaryl; in another specific embodiment, R* may be substituted by one or more D or halogens up to fully substituted.

R and R'

In a specific embodiment, R and R' are independently H; in another specific embodiment, R and R' are independently $C_{1-6}$ alkyl; in another specific embodiment, R and R' are independently $C_{2-6}$ alkenyl; in another specific embodiment, R and R' are independently $C_{2-6}$ alkynyl; in another specific embodiment, R and R' are taken together with the nitrogen atom to which they are attached to form 4- to 8-membered heterocyclyl; in another specific embodiment, R and R' may be substituted by one or more D or halogens up to fully substituted.

p

In a specific embodiment, p is 1; in another specific embodiment, p is 2.

Any technical solution in any one of the above specific embodiments, or any combination thereof, may be combined with any technical solution in other specific embodiments or any combination thereof. For example, any technical solution of X or any combination thereof may be combined with any technical solution of Y, $R_1$-$R_6$, ring A, ring B, ring C, $R_a$, $R_b$, R*, m, n, p, R and R' or any combination thereof. The present disclosure is intended to include all combination of such technical solutions, which are not exhaustively listed here to save space.

In a more specific embodiment, the present disclosure provides a compound of general formula (I) having the following general structure, or a pharmaceutically acceptable salt, enantiomer, diastereomer, racemate, solvate, hydrate, polymorph, prodrug, or isotopic variant thereof, or a mixture thereof.

(I-1)

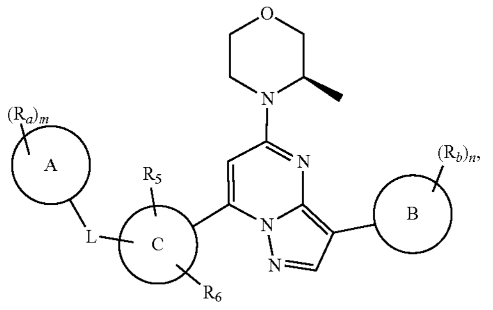

(I-2)

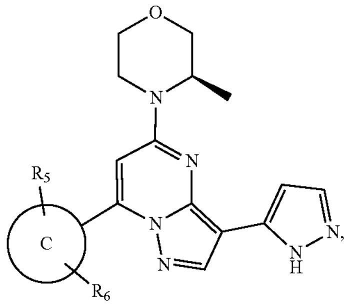

, (II)

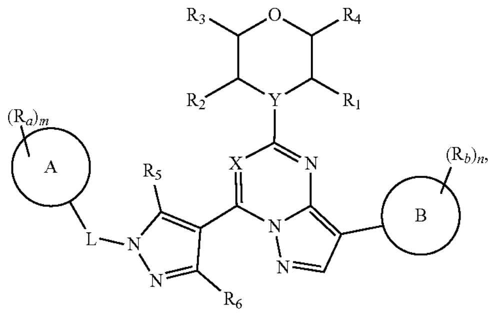

(II-1)

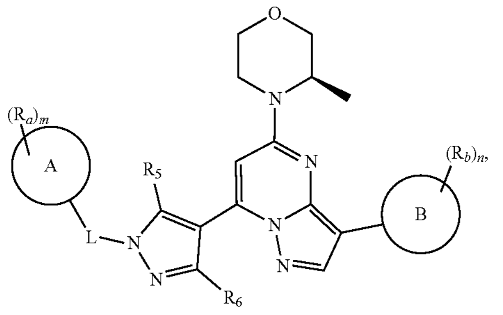

-continued (III)

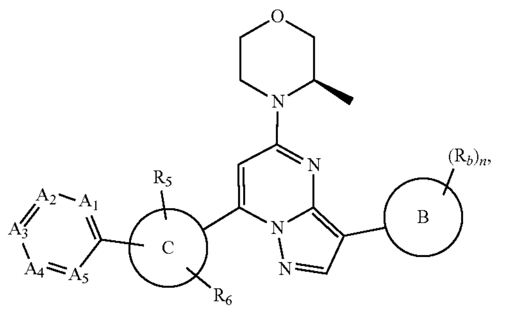

(III-1)

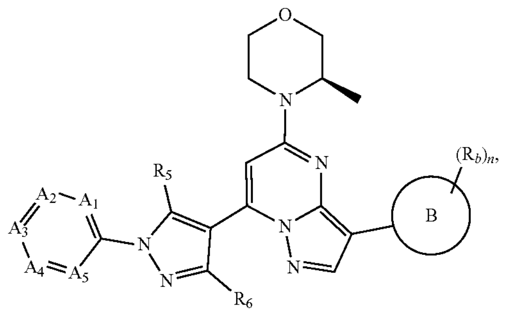

(III-2)

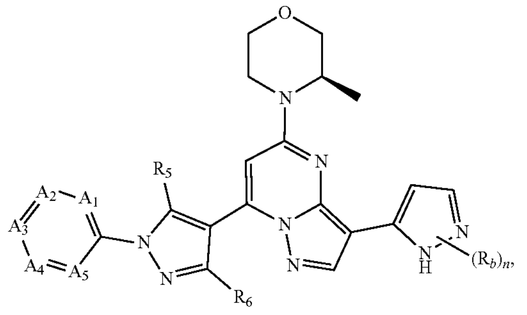

(III-3)

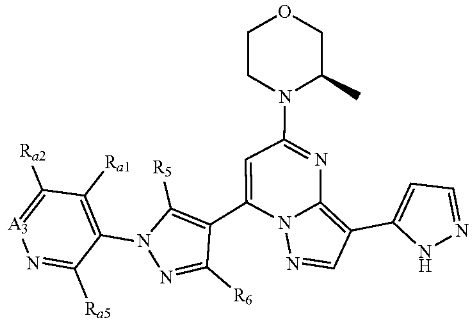

or

-continued (III-4)

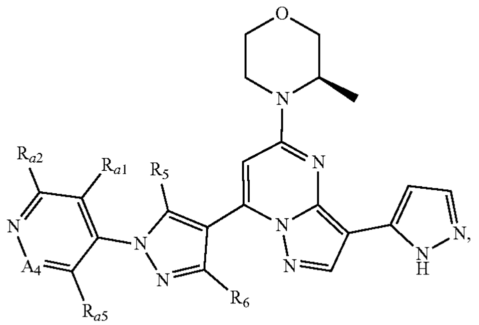

wherein each group is as defined in the context.

In a more specific embodiment, the present disclosure provides a compound of general formula (I-1) or (I-2), or a pharmaceutically acceptable salt, enantiomer, diastereomer, racemate, solvate, hydrate, polymorph, prodrug, or isotopic variant thereof, or a mixture thereof:

(I-1)

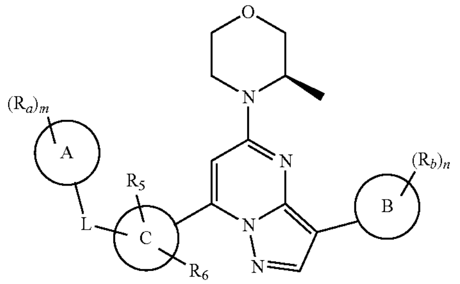

or (I-2)

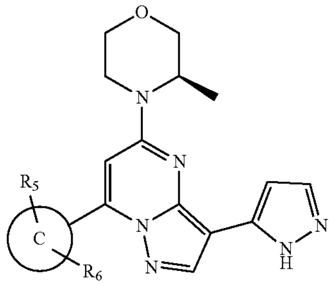

wherein ring C is $C_{3-7}$ cycloalkyl or 4- to 7-membered heterocyclyl; alternatively cyclopentyl or tetrahydropyranyl;

ring B is pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrrolyl, furanyl, thienyl, pyrazolyl or pyridyl;

$R_5$ is alternatively H, D, halogen, —CN, —NRR', —OR, or —SR, wherein the groups may be substituted by one or more D or halogens up to fully substituted; alternatively, $R_5$ is located on the C atom where the ring C is attached to the parent nucleus;

Other groups are as defined in the context.

In a more specific embodiment, the present disclosure provides a compound of general formula (I-1), or a pharmaceutically acceptable salt, enantiomer, diastereomer, racemate, solvate, hydrate, polymorph, prodrug, or isotopic variant thereof, or a mixture thereof.

(I-1)

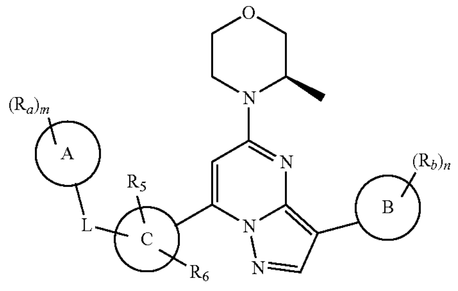

wherein ring C is 5- to 6-membered heteroaryl or phenyl; alternatively pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrazolyl, oxazolyl, isoxazolyl, thiazolyl, isothiazolyl or triazolyl; alternatively pyrazolyl;

Other groups are as defined in the context.

In another more specific embodiment, the present disclosure provides the above compound of general formula (I-1), or a pharmaceutically acceptable salt, enantiomer, diastereomer, racemate, solvate, hydrate, polymorph, prodrug, or isotopic variant thereof, or a mixture thereof, wherein ring B is pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrrolyl, furanyl, thienyl, pyrazolyl or pyridyl;

Other groups are as defined in the context.

In a more specific embodiment, the present disclosure provides a compound of general formula (II) or (II-1), or a pharmaceutically acceptable salt, enantiomer, diastereomer, racemate, solvate, hydrate, polymorph, prodrug, or isotopic variant thereof, or a mixture thereof:

(II)

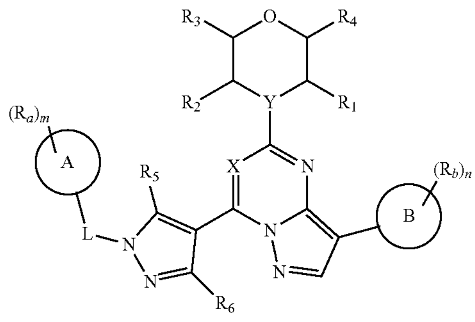

or (II-1)

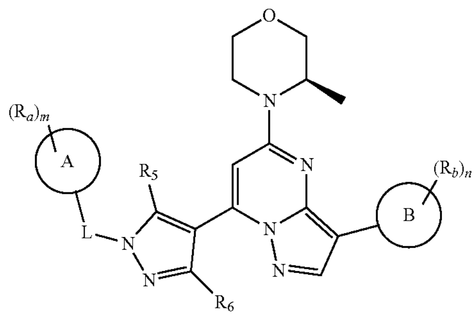

wherein ring A is absent, $C_{3-7}$ cycloalkyl or 4- to 7-membered heterocyclyl;

Other groups are as defined in the context.

In another more specific embodiment, the present disclosure provides the above compound of general formula (II) or (II-1), or a pharmaceutically acceptable salt, enantiomer, diastereomer, racemate, solvate, hydrate, polymorph, prodrug, or isotopic variant thereof, or a mixture thereof, wherein ring A is absent, or is 4- to 7-membered heterocyclyl; alternatively piperidyl or piperazinyl;

ring B is pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrrolyl, furanyl, thienyl, pyrazolyl or pyridyl;

L is a bond, —O—, —S—, —N(R)—, —C(O)— or $C_{1-6}$ alkylene;

$R_5$ and $R_6$ are independently $C_{1-6}$ alkyl, $C_{1-6}$ haloalkyl, $C_{2-6}$ alkenyl or $C_{2-6}$ alkynyl, wherein the groups may be substituted by one or more D up to fully deuterated;

Other groups are as defined in the context.

In a more specific embodiment, the present disclosure provides a compound of general formula (III) or (III-1), or a pharmaceutically acceptable salt, enantiomer, diastereomer, racemate, solvate, hydrate, polymorph, prodrug, or isotopic variant thereof, or a mixture thereof:

(III)

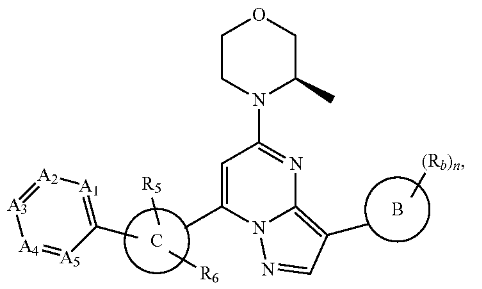

(III-1)

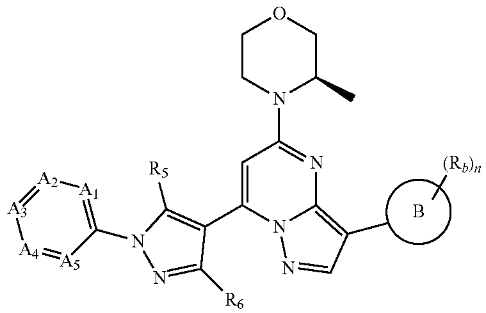

wherein ring C is 5- to 6-membered heteroaryl or phenyl; alternatively pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrazolyl, oxazolyl, isoxazolyl, thiazolyl, isothiazolyl or triazolyl; alternatively pyrazolyl;

Other groups are as defined in the context.

In another more specific embodiment, the present disclosure provides the above compound of general formula (III) or (III-1), or a pharmaceutically acceptable salt, enantiomer, diastereomer, racemate, solvate, hydrate, polymorph, prodrug, or isotopic variant thereof, or a mixture thereof, wherein ring B is pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrrolyl, furanyl, thienyl, pyrazolyl or pyridyl;

Other groups are as defined in the context.

In a more specific embodiment, the present disclosure provides a compound of general formula (III-2) or (III-3), or a pharmaceutically acceptable salt, enantiomer, diastereomer, racemate, solvate, hydrate, polymorph, prodrug, or isotopic variant thereof, or a mixture thereof.

(III-2)

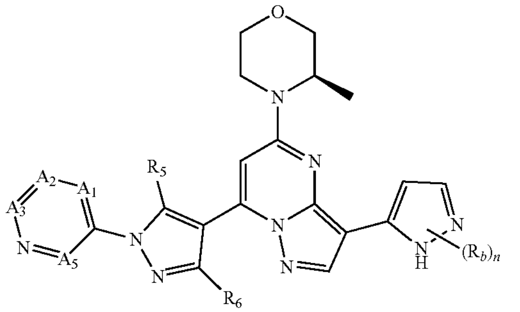

or (III-3)

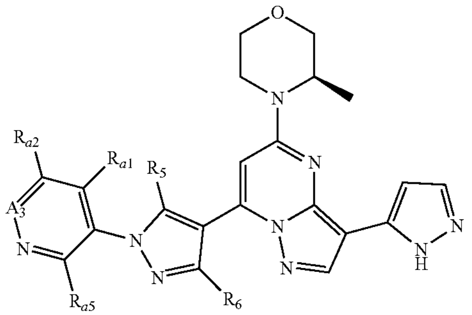

wherein $A_1$ is $CR_{a1}$ or N; $A_2$ is $CR_{a2}$ or N; $A_5$ is $CR_{a5}$ or N;

Other groups are as defined in the context.

In another more specific embodiment, the present disclosure provides the above compound of general formula (III-3), or a pharmaceutically acceptable salt, enantiomer, diastereomer, racemate, solvate, hydrate, polymorph, prodrug, or isotopic variant thereof, or a mixture thereof, wherein $A_3$ is $CR_{a3}$ or N;

$R_{a1}$, $R_{a2}$, $R_{a3}$, $R_{a5}$, $R_5$ and $R_6$ are independently H, D, halogen, —CN, —OR, —SR, —NRR', —C(O)R, —C(O)OR, —C(O)NRR' or $C_{1-6}$ alkyl, wherein the groups may be substituted by one or more D or halogens up to fully substituted;

Other groups are as defined in the context.

In another more specific embodiment, the present disclosure provides the above compound of general formula (III-3), or a pharmaceutically acceptable salt, enantiomer, diastereomer, racemate, solvate, hydrate, polymorph, prodrug, or isotopic variant thereof, or a mixture thereof, wherein $A_3$ is $CR_{a3}$ or N;

$R_{a1}$, $R_{a2}$, $R_{a3}$ and $R_{a5}$ are independently selected from H, D, halogen, —CN, —OH, —$C(O)NH_2$, $C_{1-6}$ alkyl and $C_{1-6}$ haloalkyl, wherein the groups may be substituted by one or more D up to fully deuterated;

$R_5$ and $R_6$ are independently $C_{1-6}$ alkyl or $C_{1-6}$ haloalkyl, wherein the groups may be substituted by one or more D up to fully deuterated.

In another more specific embodiment, the present disclosure provides the above compound of general formula (III-3), or a pharmaceutically acceptable salt, enantiomer, diastereomer, racemate, solvate, hydrate, polymorph, prodrug, or isotopic variant thereof, or a mixture thereof, wherein $A_3$ is $CR_{a3}$ or N;

$R_{a1}$ is H or D;

$R_{a2}$ is H, D, halogen, —CN, —OH, —$C(O)NH_2$, $C_{1-6}$ alkyl or $C_{1-6}$ haloalkyl;

$R_{a3}$ is H, D or —OH;

$R_{a5}$ is H or D;

$R_5$ is $C_{1-6}$ alkyl or $C_{1-6}$ haloalkyl; alternatively methyl;

$R_6$ is $C_{1-6}$ alkyl or $C_{1-6}$ haloalkyl; alternatively methyl.

In a more specific embodiment, the present disclosure provides a compound of general formula (III-3), or a pharmaceutically acceptable salt, enantiomer, diastereomer, racemate, solvate, hydrate, polymorph, prodrug, or isotopic variant thereof, or a mixture thereof:

(III-3)

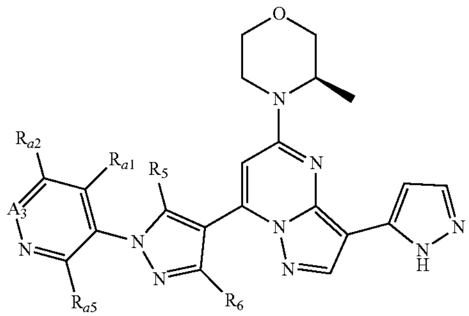

wherein $A_3$ is $CR_{a3}$ or N;

$R_{a1}$, $R_{a2}$, $R_{a3}$, $R_{a5}$, $R_5$ and $R_6$ are independently H, D, halogen, —OR, —SR, —NRR', $C_{1-6}$ alkyl or $C_{1-6}$ haloalkyl, wherein the groups may be substituted by one or more D up to fully deuterated;

R and R' are independently selected from H, $C_{1-6}$ alkyl, $C_{1-6}$ haloalkyl, $C_2$-6 alkenyl and $C_{2-6}$ alkynyl, or R and R' are taken together with the nitrogen atom to which they are attached to form 4- to 8-membered heterocyclyl; wherein the groups may be substituted by one or more D up to fully deuterated.

In another more specific embodiment, the present disclosure provides the above compound of general formula (III-3), or a pharmaceutically acceptable salt, enantiomer, diastereomer, racemate, solvate, hydrate, polymorph, prodrug, or isotopic variant thereof, or a mixture thereof, wherein $A_3$ is $CR_{a3}$ or N;

$R_{a1}$, $R_{a2}$, $R_{a3}$ and $R_{a5}$ are independently selected from H, D, halogen, —OH, $C_{1-6}$ alkyl and $C_{1-6}$ haloalkyl, wherein the groups may be substituted by one or more D up to fully deuterated;

$R_5$ and $R_6$ are independently $C_{1-6}$ alkyl or $C_{1-6}$ haloalkyl, wherein the groups may be substituted by one or more D up to fully deuterated.

In another more specific embodiment, the present disclosure provides the above compound of general formula (III-3), or a pharmaceutically acceptable salt, enantiomer, diastereomer, racemate, solvate, hydrate, polymorph, prodrug, or isotopic variant thereof, or a mixture thereof, wherein $A_3$ is $CR_{a3}$ or N;

$R_{a1}$ is H or D;

$R_{a2}$ is H, D, halogen, $C_{1-6}$ alkyl or $C_{1-6}$ haloalkyl;

$R_{a3}$ is H, D or —OH;

$R_{a5}$ is H or D;

$R_5$ is $C_{1-6}$ alkyl or $C_{1-6}$ haloalkyl; alternatively methyl;

$R_6$ is $C_{1-6}$ alkyl or $C_{1-6}$ haloalkyl; alternatively methyl.

In a more specific embodiment, the present disclosure provides a compound of general formula (III-4), or a pharmaceutically acceptable salt, enantiomer, diastereomer, racemate, solvate, hydrate, polymorph, prodrug, or isotopic variant thereof, or a mixture thereof:

(III-4)

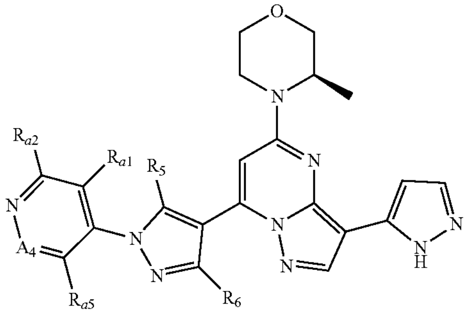

wherein $A_4$ is $CR_{a4}$ or N;

$R_{a1}$, $R_{a2}$, $R_{a4}$, $R_{a5}$, $R_5$ and $R_6$ are independently H, D, halogen, —CN, —OR, —SR, —NRR', —C(O)R, —C(O)OR, —C(O)NRR' or $C_{1-6}$ alkyl, wherein the groups may be substituted by one or more D or halogens up to fully substituted;

Other groups are as defined in the context.

In another more specific embodiment, the present disclosure provides the above compound of general formula (III-4), or a pharmaceutically acceptable salt, enantiomer, diastereomer, racemate, solvate, hydrate, polymorph, prodrug, or isotopic variant thereof, or a mixture thereof, wherein $A_4$ is $CR_{a4}$ or N;

$R_{a1}$, $R_{a2}$, $R_{a4}$ and $R_{a5}$ are independently selected from H, D, halogen, —CN, —OH, —C(O)$NH_2$, $C_{1-6}$ alkyl and $C_{1-6}$ haloalkyl, wherein the groups may be substituted by one or more D up to fully deuterated;

$R_5$ and $R_6$ are independently $C_{1-6}$ alkyl or $C_{1-6}$ haloalkyl, wherein the groups may be substituted by one or more D up to fully deuterated.

In another more specific embodiment, the present disclosure provides the above compound of general formula (III-4), or a pharmaceutically acceptable salt, enantiomer, diastereomer, racemate, solvate, hydrate, polymorph, prodrug, or isotopic variant thereof, or a mixture thereof, wherein $A_4$ is $CR_{a4}$ or N;

$R_{a1}$ is H, D or halogen;

$R_{a2}$ is H, D, halogen, —CN, —OH, —C(O)$NH_2$, $C_{1-6}$ alkyl or $C_{1-6}$ haloalkyl;

$R_{a4}$ is H, D or —OH;

$R_{a5}$ is H or D;

$R_5$ is $C_{1-6}$ alkyl or $C_{1-6}$ haloalkyl; alternatively methyl;

$R_6$ is $C_{1-6}$ alkyl or $C_{1-6}$ haloalkyl; alternatively methyl.

Alternative compounds of the present disclosure include, but are not limited to, the compounds listed below, or pharmaceutically acceptable salts, enantiomers, diastereomers, racemates, solvates, hydrates, polymorphs, prodrugs, or isotopic variants thereof, or mixtures thereof:

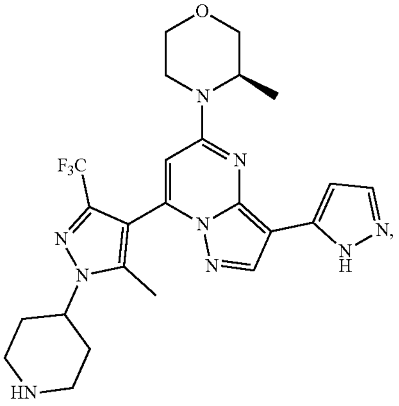

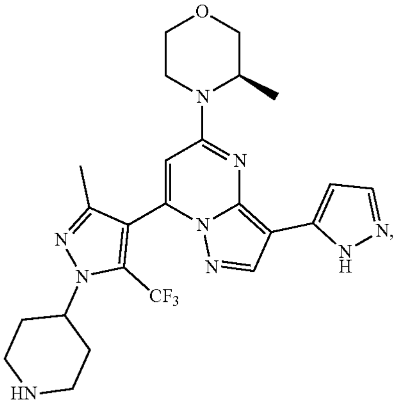

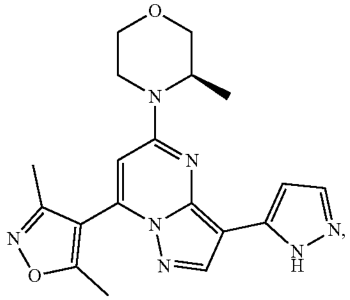

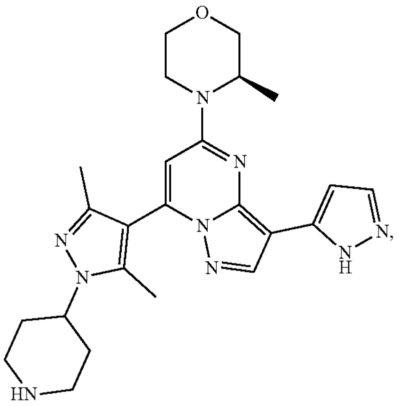

-continued
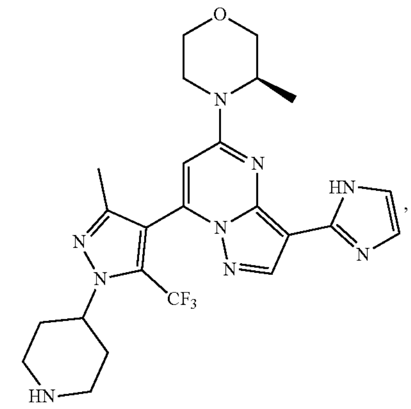
,
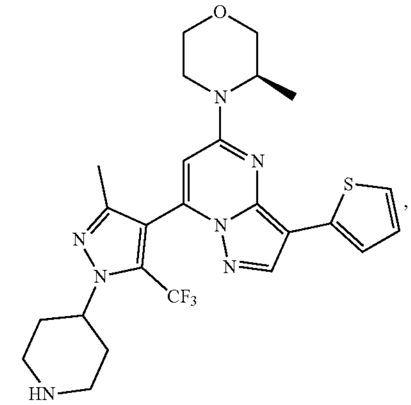
,
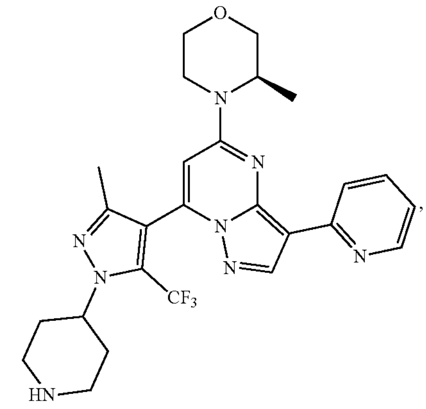
,
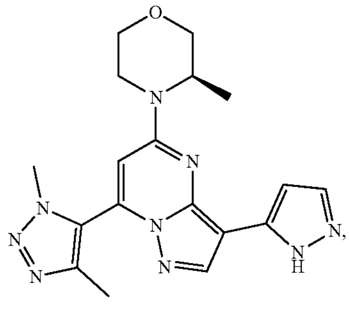
,
-continued
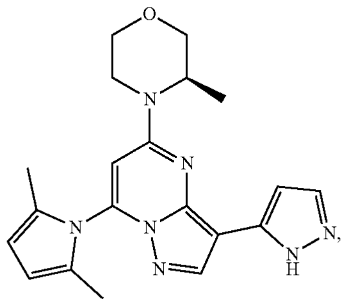
,
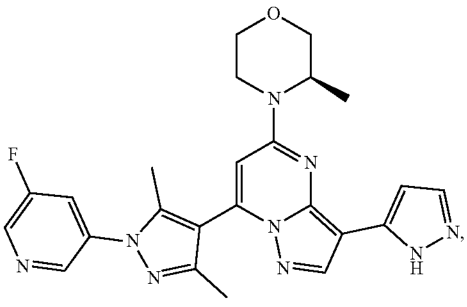
,
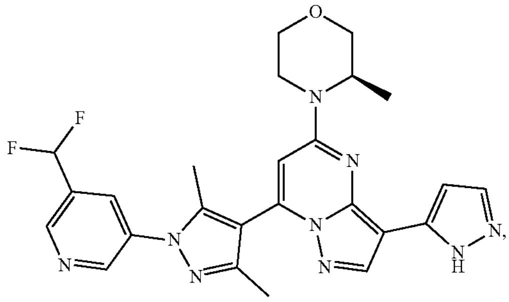
,
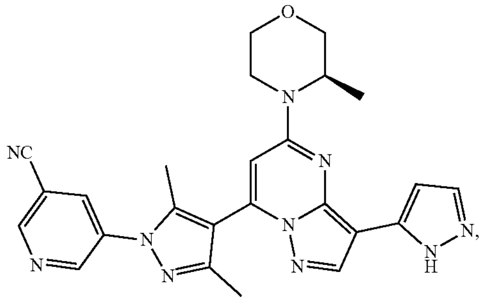
,
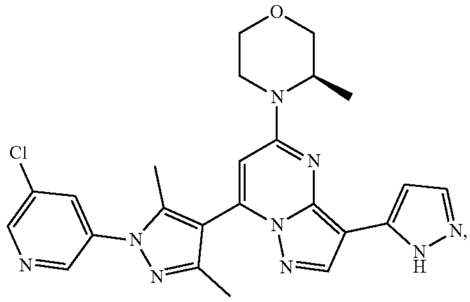
, -continued
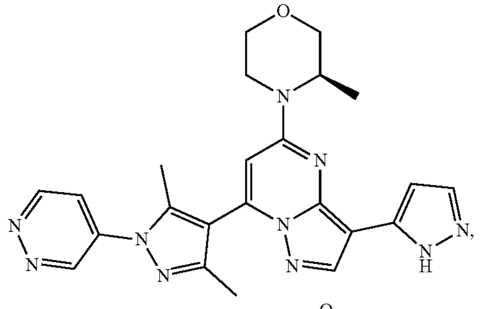
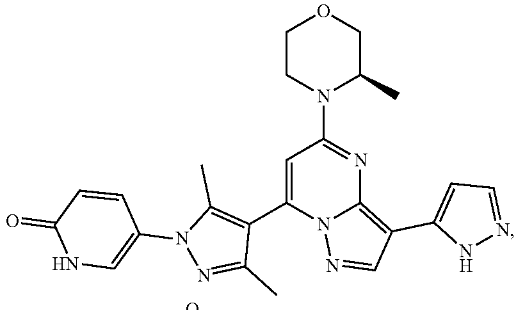
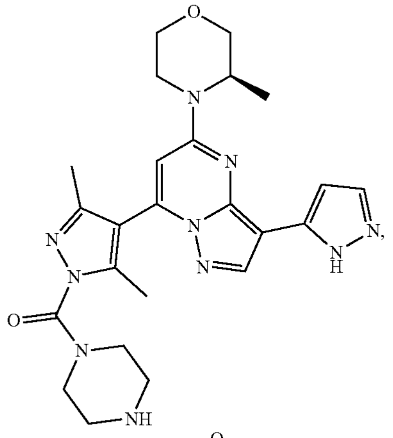
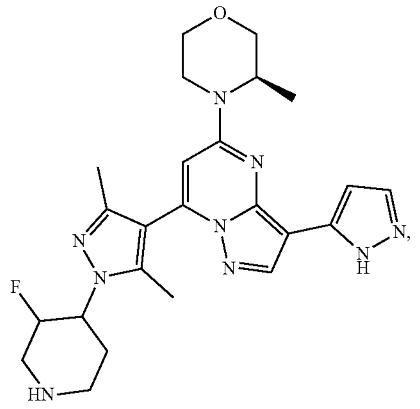
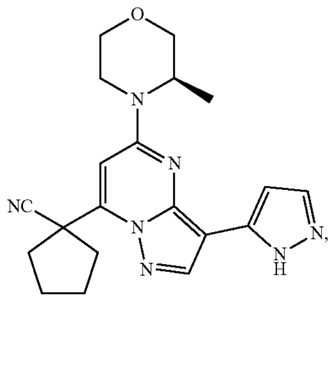
-continued
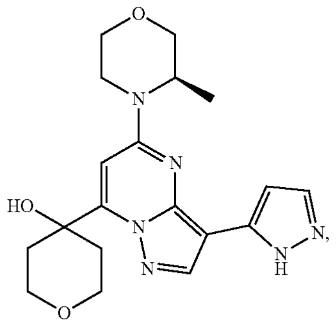
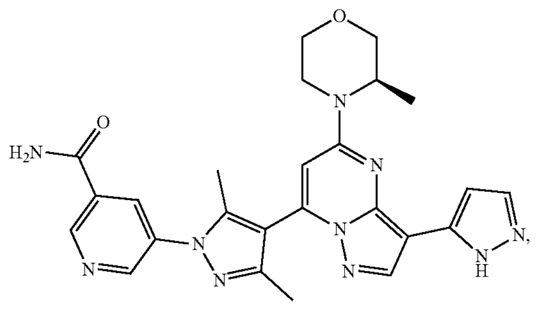
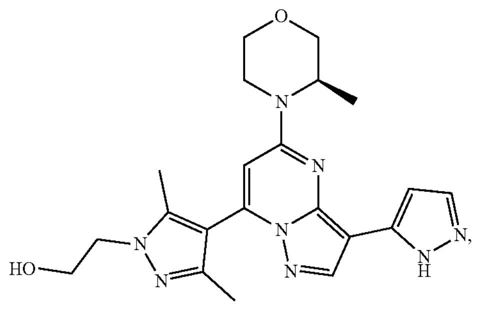
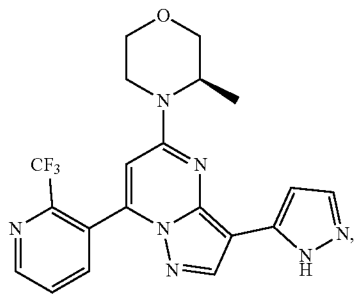
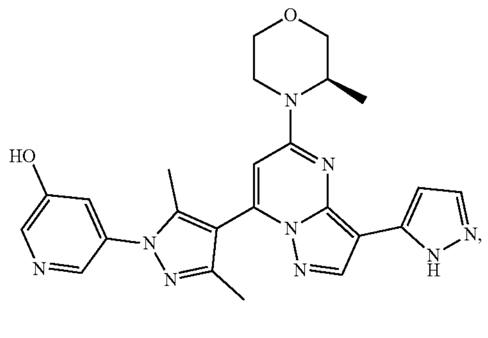

-continued

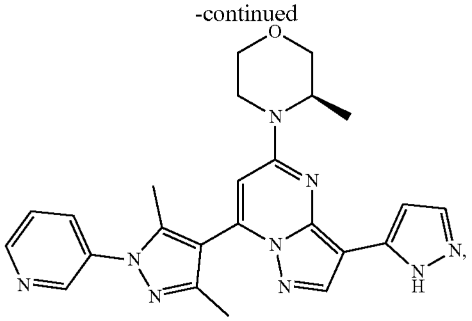

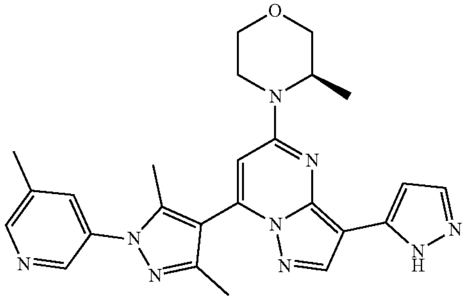

or

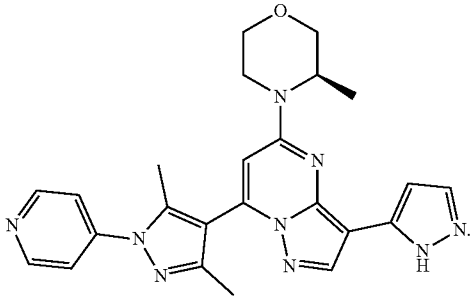

The compounds of the present disclosure may include one or more asymmetric centers, and thus may exist in a variety of stereoisomeric forms, for example, enantiomers and/or diastereomers. For example, the compounds of the present disclosure may be in the form of an individual enantiomer, diastereomer or geometric isomer (e.g., cis- and trans-isomers), or may be in the form of a mixture of stereoisomers, including racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or alternative isomers can be prepared by asymmetric synthesis.

It will be understood by those skilled in the art that the organic compounds can form complexes with solvents in which they are reacted or from which they are precipitated or crystallized. These complexes are known as "solvates". Where the solvent is water, the complex is known as "hydrate". The present disclosure encompasses all solvates of the compounds of the present disclosure.

The term "solvate" refers to forms of a compound or a salt thereof, which are associated with a solvent, usually by a solvolysis reaction. This physical association may include hydrogen bonding. Conventional solvents include water, methanol, ethanol, acetic acid, DMSO, THF, diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a definite ratio to the number of the compound molecules in the hydrate. Therefore, hydrates of a compound can be represented, for example, by a general formula R·x $H_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates (R·0.5 $H_2O$)) and polyhydrates (x is a number greater than 1, for example, dihydrates (R·2 $H_2O$) and hexahydrates (R·6 $H_2O$)).

Compounds of the present disclosure may be in an amorphous or a crystalline form (polymorph). Furthermore, the compounds of the present disclosure may exist in one or more crystalline forms. Therefore, the present disclosure includes all amorphous or crystalline forms of the compounds of the present disclosure within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

The present disclosure also comprises compounds that are labeled with isotopes, which are equivalent to those described in formula (I), but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present disclosure that comprise the above isotopes and/or other isotopes of other atoms, prodrugs thereof and pharmaceutically acceptable salts of said compounds or prodrugs all are within the scope of the present disclosure. Certain isotope-labeled compounds of the present disclosure, such as those incorporating radioactive isotopes (e.g., $^{3}H$ and $^{14}C$), can be used for the measurement of the distribution of drug and/or substrate in tissue. Tritium, which is $^{3}H$ and carbon-14, which is $^{14}C$ isotope, are yet alternative, because they are easy to prepare and detect. Furthermore, replaced by heavier isotopes, such as deuterium, which is $^{2}H$, may provide therapeutic benefits due to the higher metabolic stability, such as prolonging the half-life in vivo or decreasing the dosage requirements, and thus may be alternative in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

In addition, prodrugs are also included within the context of the present disclosure. The term "prodrug" as used herein refers to a compound that is converted into an active form that has medical effects in vivo by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

The prodrugs are any covalently bonded compounds of the present disclosure, which release the parent compound in vivo when the prodrug is administered to a patient. Prodrugs are typically prepared by modifying functional groups in such a way that the modifications can be cleaved either by routine manipulation or decompose in vivo to yield the parent compound. Prodrugs include, for example, compounds of the present disclosure wherein the hydroxyl, amino or sulfhydryl groups are bonded to any group that, when administered to a patient, cleaves to form the hydroxyl, amino or sulfhydryl groups. Thus, representative examples of prodrugs include (but are not limited to) the acetate/acetamide, formate/formamide and benzoate/benzamide derivatives of the hydroxyl, amino or sulfhydryl functional groups of the compounds of formula (I). Furthermore, in the case of carboxylic acid (—COOH), esters such as methyl esters and ethyl esters, etc. can be employed. The ester itself may be active in their own and/or hydrolyzable under in vivo conditions in the human body. Suitable pharmaceutically acceptable in vivo hydrolysable ester groups include those groups that can readily break down in the human body to release the parent acids or salts thereof.

The present disclosure also provides a pharmaceutical formulation comprising a therapeutically effective amount of a compound of formula (I), or therapeutically acceptable salts thereof, and pharmaceutically acceptable carriers, diluents or excipients thereof. All of these forms belong to the present disclosure.

Pharmaceutical Compositions, Formulations and Kits

In another aspect, the present disclosure provides a pharmaceutical composition comprising a compound of the present disclosure (also referred to as the "active ingredient") and a pharmaceutically acceptable excipient. In certain embodiments, the pharmaceutical composition comprises an effective amount of the compound of the present disclosure. In certain embodiments, the pharmaceutical composition comprises a therapeutically effective amount of the compound of the present disclosure. In certain embodiments, the pharmaceutical composition comprises a prophylactically effective amount of the compound of the present disclosure.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that may be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agents, and a first and a second containers (e.g., vials, ampoules, bottles, syringes, and/or dispersible packages or other materials) containing the compound disclosed herein or other therapeutic agents. In some embodiments, kits provided can also optionally include a third container containing a pharmaceutically acceptable excipient for diluting or suspending the compound disclosed herein and/or other therapeutic agent. In some embodiments, the compound disclosed herein provided in the first container and the other therapeutic agents provided in the second container is combined to form a unit dosage form.

Administration

The pharmaceutical composition provided by the present disclosure can be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present disclosure may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or alternatively from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with alternative doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, alternatively from about 0.1 to about 20% by weight, alternatively from about 0.1 to about 10% by weight, and still alternatively from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient (s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of the present disclosure can also be administered in sustained release forms or from sustained release drug delivery systems. A description of representative sustained release materials can be found in Remington's Pharmaceutical Sciences.

The present disclosure also relates to the pharmaceutically acceptable formulations of a compound of the present disclosure. In one embodiment, the formulation comprises water. In another embodiment, the formulation comprises a cyclodextrin derivative. The most common cyclodextrins are α-, β- and γ- cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol. See, e.g., U.S. Pat. No. 5,376,645. In certain embodiments, the formulation comprises hexapropyl-β-cyclodextrin (e.g., 10-50% in water).

Treatment

As stated herein, it is known that ATR kinase have roles in tumourigenesis as well as numerous other diseases. We have found that the compounds of formula (I) possess potent anti-tumour activity which it is believed is obtained by way of inhibition of ATR kinase.

The compounds of the present disclosure are of value as anti-tumour agents. Particularly, the compounds of the present disclosure are of value as anti-proliferative, apoptotic and/or anti-invasive agents in the containment and/or treatment of solid and/or liquid tumour disease. Particularly, the compounds of the present disclosure are expected to be useful in the prevention or treatment of those tumours which are sensitive to inhibition of ATR. Further, the compounds of the present disclosure are expected to be useful in the prevention or treatment of those tumours which are mediated alone or in part by ATR. The compounds may thus be used to produce an ATR enzyme inhibitory effect in a warm-blooded animal in need of such treatment.

As stated herein, inhibitors of ATR kinase should be of therapeutic value for the treatment of proliferative disease such as cancer and in particular solid tumours such as carcinoma and sarcomas and the leukaemias and lymphoid malignancies and in particular for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias [including acute lymphoctic leukaemia (ALL), chronic myeloid leukemia (CML) and acute myeloid leukemia (AML), etc.], multiple myeloma and lymphomas.

Anti-cancer effects which are accordingly useful in the treatment of cancer in a patient include, but are not limited to, anti-tumour effects, the response rate, the time to disease progression and the survival rate. Anti-tumour effects of a method of treatment of the present disclosure include but are not limited to, inhibition of tumour growth, tumour growth delay, regression of tumour, shrinkage of tumour, increased time to regrowth of tumour on cessation of treatment, slowing of disease progression. Anti-cancer effects include prophylactic treatment as well as treatment of existing disease.

An ATR kinase inhibitor, or a pharmaceutically acceptable salt thereof, may also be useful for treating patients with cancers, including, but not limited to, haematologic malignancies such as leukaemia, multiple myeloma, lymphomas such as Hodgkin's disease, non-Hodgkin's lymphomas (including mantle cell lymphoma), and myelodysplastic syndromes, and also solid tumours and their metastases such as breast cancer, lung cancer (non-small cell lung cancer (NSCL), small cell lung cancer (SCLC), squamous cell carcinoma), endometrial cancer, tumours of the central nervous system such as gliomas, dysembryoplastic neuroepithelial tumour, glioblastoma multiforme, mixed gliomas, medulloblastoma, retinoblastoma, neuroblastoma, germinoma and teratoma, cancers of the gastrointestinal tract such as gastric cancer, oesophagal cancer, hepatocellular (liver) carcinoma, cholangiocarcinomas, colon and rectal carcinomas, cancers of the small intestine, pancreatic cancers, cancers of the skin such as melanomas (in particular metastatic melanoma), thyroid cancers, cancers of the head and neck and cancers of the salivary glands, prostate, testis, ovary, cervix, uterus, vulva, bladder, kidney (including renal cell carcinoma, clear cell and renal oncocytoma), squamous cell carcinomas, sarcomas such as osteosarcoma, chondrosarcoma, leiomyosarcoma, soft tissue sarcoma, Ewing's sarcoma, gastrointestinal stromal tumour (GIST), Kaposi's sarcoma, and paediatric cancers such as rhabdomyosarcomas and neuroblastomas.

The compounds of the present disclosure and the methods of treatment comprising the administering or use of a ATR kinase inhibitor, or a pharmaceutically acceptable salt thereof, are expected to be particularly useful for the treatment of patients with lung cancer, prostate cancer, melanoma, ovarian cancer, breast cancer, endometrial cancer, kidney cancer, gastric cancer, sarcomas, head and neck cancers, tumours of the central nervous system and their metastases, and also for the treatment of patients with acute myeloid leukaemia.

The effective dose of the compound of the present disclosure is usually at an average daily dose of 0.01 mg to 50 mg compound/kg of patient weight, alternatively 0.1 mg to 25 mg compound/kg of patient weight, in single or multiple administrations. Generally, the compound of the present disclosure can be administered to the patient who needs this treatment in the daily dose range of about 1 mg to about 3500 mg per patient, alternatively 10 mg to 1000 mg. For example, the daily dose per patient can be 10, 20, 30, 40, 50, 60, 70, 80, 90, 100, 150, 200, 250, 300, 350, 400, 500, 600, 700, 800, 900 or 1000 mg. It can be administered once or several times a day, weekly (or several days apart) or on an intermittent schedule. For example, on a weekly basis (e.g. every Monday), the compound can be administered one or more times a day, variably for several weeks, for example 4-10 weeks. Or, the compound may be administered daily for several days (e.g. 2-10 days), and then a few days (e.g. 1-30 days) without administering the compound, repeating the cycle arbitrarily or repeating a given number of times, e.g. 4-10 cycles. For example, the compound of the present disclosure can be administered daily for 5 days, and then interrupted for 9 days, and then administered daily for 5 days, then interrupted for 9 days, and so on, repeating the cycle arbitrarily or repeating 4-10 times in total.

Combination Therapy

The treatment defined herein may be applied as a sole therapy or may involve, in addition to the compounds of the present disclosure, conventional surgery or radiotherapy or chemotherapy. Accordingly, the compounds of the present disclosure can also be used in combination with existing therapeutic agents for the treatment of cancer.

Suitable agents to be used in combination include:

(i) antiproliferative/antineoplastic drugs and combinations thereof, as used in medical oncology such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example *Vinca* alkaloids like vincristine, vinblastine, vindesine and vinorelbine and taxoids like paclitaxel and taxotere); topoisomerase inhibitors (for example epipodophyllotoxins like etoposide and teniposide, amsacrine, topotecan and camptothecins); and DNA damage repair inhibitors (e.g. olaparib, such as rucaparib and niraparib);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like AZD0530 and dasatinib), and metalloproteinase inhibitors like marimastat and inhibitors of urokinase plasminogen activator receptor function;

(iv) inhibitors of growth factor function: for example such inhibitors include growth factor antibodies and growth factor receptor antibodies (for example the anti-erbB2 antibody trastuzumab [Herceptin™] and the anti-erbBl antibody cetuximab [$C_{225}$]); such inhibitors also include, for example, tyrosine kinase inhibitors, for example inhibitors of the epidermal growth factor family (for example EGFR family tyrosine kinase inhibitors such as gefitinib, erlotinib and CI 1033; and erbB2 tyrosine kinase inhibitors such as lapatinib), inhibitors of the hepatocyte growth factor family; inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or Akt kinases;

(v) antiangiogenic agents such as those which inhibit the effects of vascular endothelial growth factor, for example the anti-vascular endothelial cell growth factor antibody bevacizumab (Avastin™) and VEGF receptor tyrosine kinase inhibitors such as ZD6474, AZD2171, vatalanib and sunitinib, and compounds that work by other mechanisms (for example linomide, inhibitors of integral avβ3 function and angiostatin);

(vi) vascular damaging agents such as combretastatin;

(vii) antisense therapies, for example those which are directed to the targets listed above, such as ISIS 2503;

(viii) gene therapy approaches, including approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapeutic approaches, including ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

EXAMPLES

The materials or reagents used herein are commercially available or are prepared by synthetic methods generally known in the art. The following reaction routes exemplify the specific synthetic methods of the compounds of the present disclosure.

The Details are as Follows

Preparation of key intermediates a1-a4:

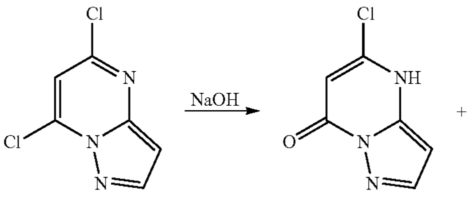

a1-1 a1-2

-continued

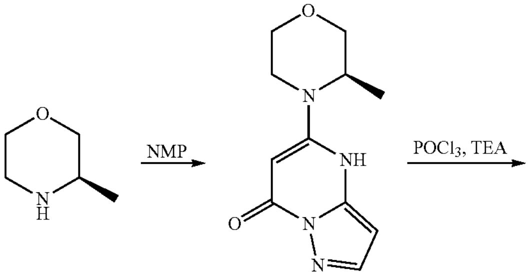

a1-3

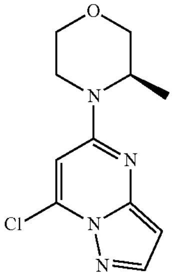

a1

The raw material 5,7-dichloropyrazolo[1,5-a]pyrimidine a1-1 (53.2 mmol, 10 g) was dissolved in 30 mL of 1 N NaOH aqueous solution. The mixture was heated to 90° C. and reacted for 0.5 h. The reaction was stopped. The mixture was cooled to room temperature, and 1 N hydrochloric acid solution was slowly added to adjust the pH to 7. The mixture was extracted with dichloromethane, and dried over anhydrous $Na_2SO_4$ to give intermediate a1-2 (9 g, quantitative yield), LC-MS: $[M+H]^+$: 170.

Intermediate a1-2 (47.3 mmol, 8 g) and (R)-2-methylmorpholine (94.6 mmol, 9.56 g) were added to a microwave reaction flask, and dissolved by adding 30 mL of N-methylpyrrolidone NMP. The mixture was then heated to 190° C. by microwave and reacted for 6 h. The reaction was stopped. The solvent was evaporated under reduced pressure, and the residue was separated by flash column chromatography to give intermediate a1-3 (6.4 g, yield: 58%), LC-MS: $[M+H]^+$: 235.

To a reaction flask were added intermediate a1-3 (27.4 mmol, 6.4 g) and triethylamine (54.8 mmol, 5.55 g), and the mixture was dissolved with 20 mL of phosphorus oxychloride. The mixture was heated to 80° C. and stirred for 2 h. The reaction was stopped. The reaction mixture was quenched by slowly adding 100 mL of ice water, and then the mixture was adjusted to pH of 8 by adding 1 N NaOH aqueous solution dropwise. The mixture was extracted with dichloromethane, dried with anhydrous $Na_2SO_4$, and separated by flash column chromatography to give intermediate at (4.4 g, yield: 64%), LC-MS: $[M+H]^+$: 253.

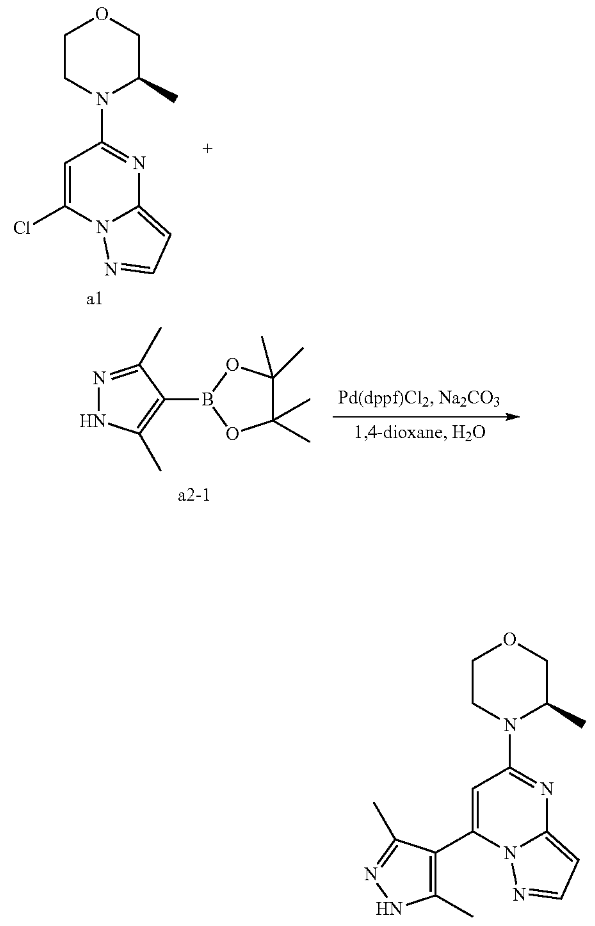

al a2-1 a2

Intermediate at (15.9 mmol, 4.0 g) and intermediate 3,5-dimethyl-1H-pyrazole-4-boronic acid pinacol ester a2-1 (24.0 mmol, 5.3 g) were dissolved in 50 mL of a mixture of 1,4-dioxane and water (v/v: 9/1) under nitrogen. Sodium carbonate (32 mmol, 3.39 g) and Pd(dppf)$Cl_2$ (1.6 mmol, 1.17 g) were added, and the mixture was heated to reflux and reacted for 10 hours. The reaction was stopped. The mixture was filtered, and the solvent was evaporated under reduced pressure. To the residue was added 50 mL of water. The mixture was extracted with ethyl acetate, and separated by flash column chromatography to give intermediate a2 (3.2 g, yield: 65%), LC-MS: $[M+H]^+$: 313.

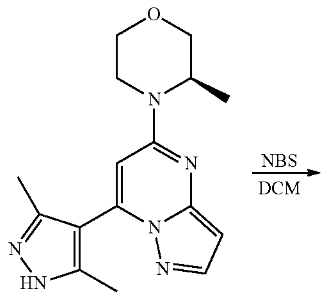

a2

-continued

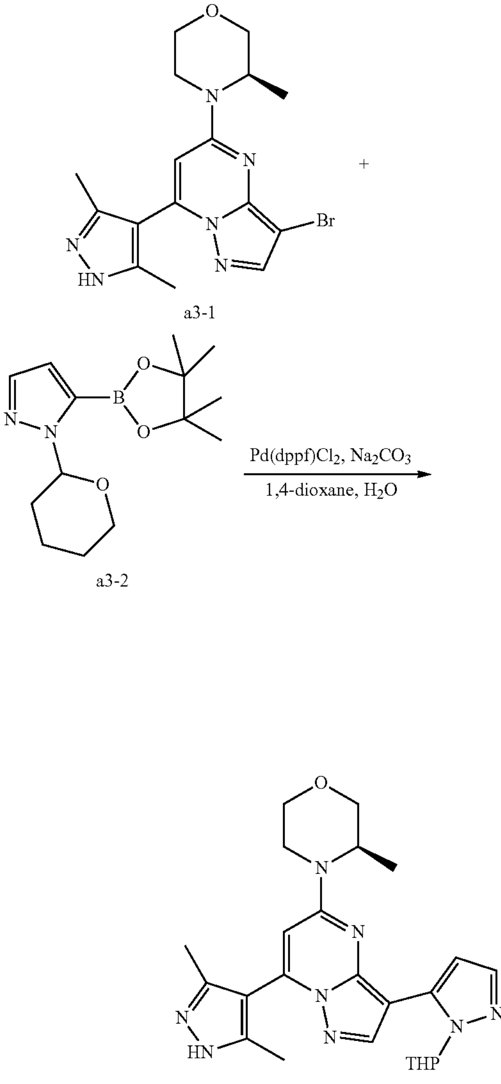

a3-1 a3-2 a3

Intermediate a2 (10.25 mmol, 3.2 g) was dissolved in 15 mL of anhydrous dichloromethane in an ice bath, and N-bromosuccinimide NBS (10.3 mmol, 1.8 g) was slowly added in batches. The mixture was stirred for another 2 hours. The reaction was stopped, and 50 mL of saturated aqueous ammonium chloride solution was added. The mixture was extracted with dichloromethane, dried over anhydrous sodium sulfate and separated by flash column chromatography to give the intermediate a3-1 (3.9 g, yield: 98%). LC-MS: $[M+H]^+$: 392.

Intermediate a3-1 (3.32 mmol, 1.3 g) and the raw material a3-2 (4.98 mmol, 1.38 g) were dissolved in 20 mL of a mixture of 1,4-dioxane and water (v/v: 9/1) under nitrogen, and sodium carbonate (6.64 mmol, 704 mg) and Pd(dppf)$Cl_2$ (0.33 mmol, 241 mg) were added. The mixture was heated to 100° C. by microwave and reacted for 1 hour. The reaction was stopped. The mixture was filtered, and 40 mL of water was added to the system. The mixture was extracted with ethyl acetate, dried over anhydrous sodium sulfate, and separated by flash column chromatography to give intermediate a3 (400 mg, yield: 26%). LC-MS: $[M+H]^+$: 463.

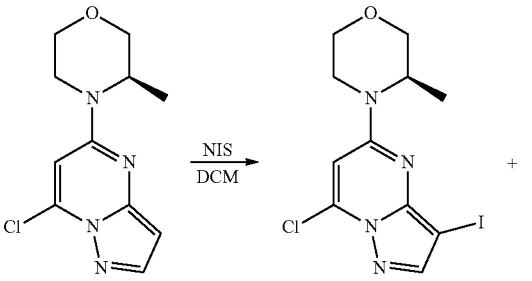

a1 a4-1

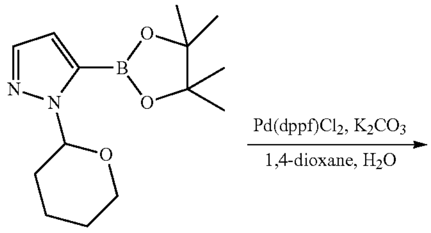

a3-2

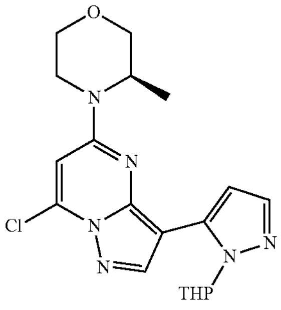

a4

Intermediate at (1.63 mmol, 410 mg) was dissolved in 15 mL of anhydrous dichloromethane in an ice bath, and N-iodosuccinimide NIS (1.79 mmol, 403 mg) was slowly added in batches. The mixture was stirred for another 2 hours. The reaction was stopped, and 50 mL of saturated aqueous ammonium chloride solution was added. The mixture was extracted with dichloromethane, and dried over anhydrous sodium sulfate to give intermediate a4-1 (700 mg, crude). LC-MS: $[M+H]^+$: 379.

Intermediate a4-1 (700 mg) and the raw material a3-2 (2.44 mmol, 678 mg) were dissolved in 20 mL of a mixture of 1,4-dioxane and water (v/v: 9/1) under nitrogen, and potassium carbonate (3.26 mmol, 451 mg) and $Pd(dppf)Cl_2$ (0.16 mmol, 117 mg) were added. The mixture was heated to 100° C. by microwave and reacted for 1 hour. The reaction was stopped. The mixture was filtered, and 40 mL of water was added to the system. The mixture was extracted with ethyl acetate, dried over anhydrous sodium sulfate, and separated by flash column chromatography to give intermediate a4 (220 mg, total yield for two steps: 34%). LC-MS: $[M+H]^+$: 403.

Preparation of key intermediates b1-b7:

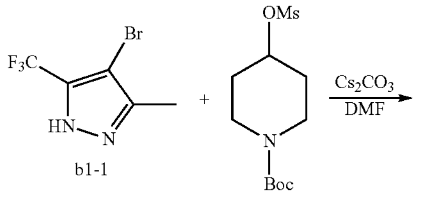

b1-1 b1-2

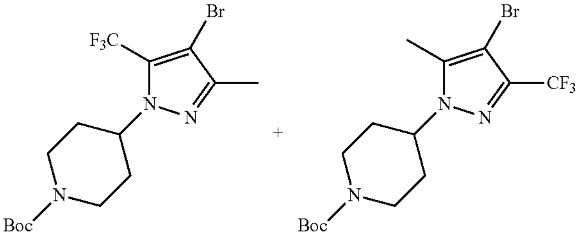

b1-3 b1-4

To a reaction flask were added raw material b1-1 (36.7 mmol, 7 g) and cesium carbonate (92.1 mmol, 30.03 g), and the mixture was dissolved with 100 mL of DMF. The raw material b1-2 (36.8 mmol, 8.43 g) was slowly added. The mixture was heated to 80° C. and reacted for 4 h. The reaction was then stopped. 300 mL of water was slowly added. The mixture was extracted with ethyl acetate, dried over anhydrous $Na_2SO_4$, and separated by flash column chromatography to give intermediate b1-3 (3.4 g, yield: 23%) and intermediate b1-4 (7.0 g, yield: 47%), LC-MS: $[M+H]^+$: 413.

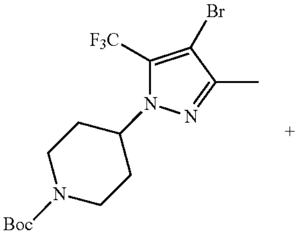

b1-3

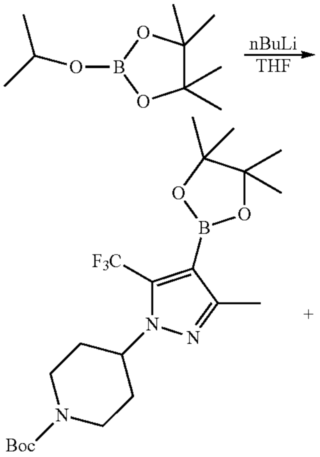

b1

-continued

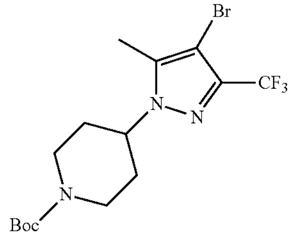

b1-4

+

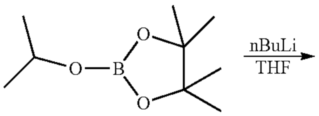

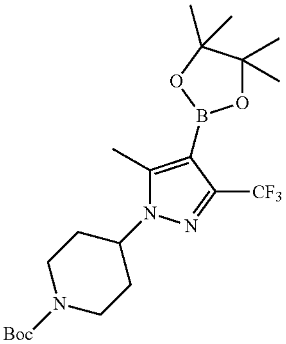

b2

Intermediate b1-3 (6.3 mmol, 2.6 g) was dissolved in 60 mL of anhydrous THF at −78° C. Butyllithium (3.0 mL, 2.5 M) was added dropwise. After 30 min isopropoxyboronic acid pinacol ester (9.5 mmol, 1.88 mL) was added. The mixture was reacted at −78° C. for another 3 h. The reaction mixture was quenched by adding 150 mL of saturated aqueous ammonium chloride solution, extracted with dichloromethane, and dried over anhydrous sodium sulfate to give the crude intermediate b1, which was directly used in the next reaction step. LC-MS: $[M+H]^+$: 460.

Referring to the synthetic route of intermediate b1, b1-4 was used as raw material to give the crude intermediate b2, LC-MS: $[M+H]^+$: 460.

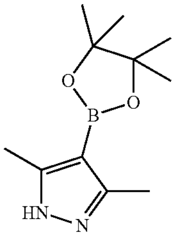

a2-1

+

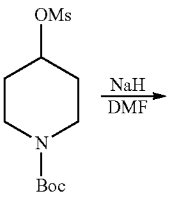

-continued

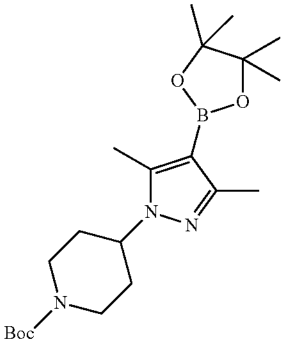

b3

In an ice bath and under nitrogen, the raw material a2-1 (2.25 mmol, 500 mg) was dissolved in 15 mL of DMF, and NaH (4.5 mmol, 180 mg) was added in batches. The mixture was stired for 30 min, and then tert-butyl 4-((methylsulfonyl)oxy)piperidine-1-carboxylate (3.37 mmol, 943 mg) was slowly added. The mixture was heated to 90° C. and reacted for another 2 hours. The reaction was stopped. The system was quenched by slowly adding 50 mL of ice water, extracted with ethyl acetate and dried over anhydrous sodium sulfate to give the crude intermediate b3, which was directly used in the next reaction step. LC-MS: [M+H]*: 406.

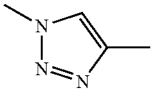

b4-1

+ $Me_3SnCl$

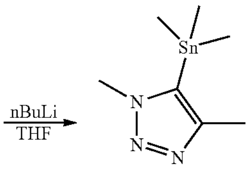

b4

Raw material b4-1 (1.54 mmol, 150 mg) was dissolved in 10 mL of anhydrous THF at −78° C. under nitrogen, and n-Butyllithium (1.0 mL, 2.5 M) was added dropwise. After 30 min, trimethyltin chloride (2.31 mmol, 462 mg) was added. The mixture was reacted at −78° C. for another 3 h. The reaction was stopped. The reaction mixture was quenched by adding 40 mL of saturated aqueous ammonium chloride solution, extracted with dichloromethane and dried over anhydrous sodium sulfate to give the crude intermediate b4, which was directly used in the next reaction step. LC-MS: $[M+H]^+$: 260.

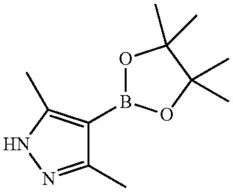

a2-1

+

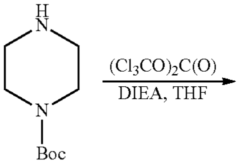

-continued

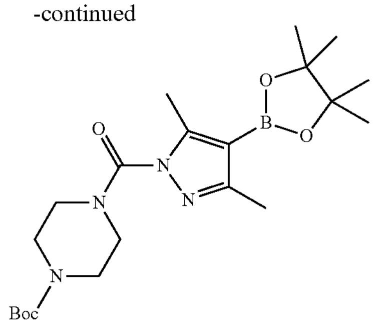

b5

The raw material a2-1 (2.0 mmol, 444 mg), tert-butyl piperazine-1-carboxylate (3.0 mmol, 559 mg), and DIEA (5.0 mmol, 645 mg) were dissolved in 15 mL of tetrahydrofuran in an ice bath. The mixture was stirred for 5 min, and then triphosgene (4.0 mmol, 1.08 g) was slowly added to the system. The mixture was stirred in an ice bath for 2 hours and then the reaction was stopped. To the reaction solution was added 40 mL of water. The mixture was extracted with dichloromethane, and separated by flash column chromatography to give intermediate b5 (180 mg, yield: 21%). LC-MS: $[M+H]^+$: 435.

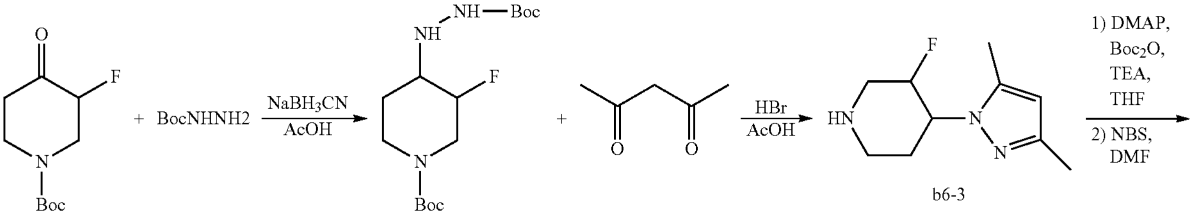

b6-1 b6-2 b6-3

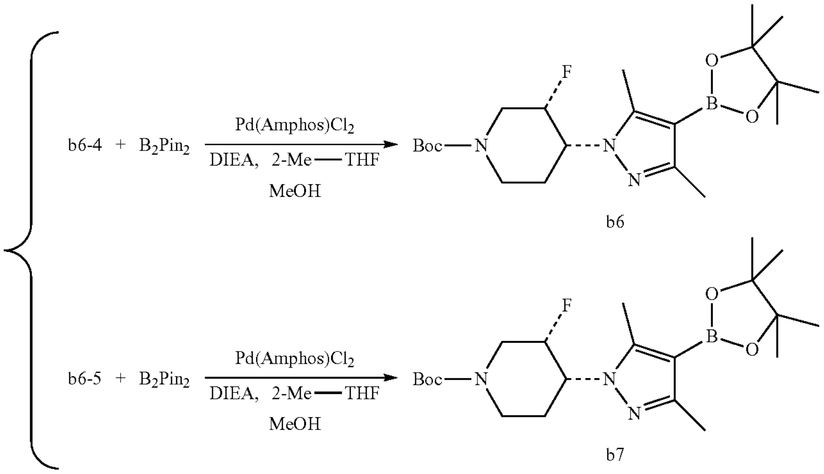

b6 b7 b6-4 =

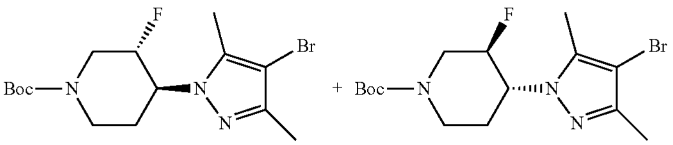

b6-5 =

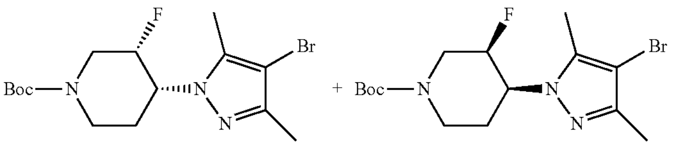

The raw material b6-1 (9.2 mmol, 2.0 g) and N-Boc-hydrazine (10.1 mmol, 1.33 g) were dissolved in 30 mL of acetic acid. The mixture was stirred for 5 min, and then $NaBH_3CN$ (27.6 mmol, 1.7 g) was slowly added. The mixture was reacted at room temperature for 10 h. The reaction was stopped. To the system was added 80 mL of ice water to quench the reaction mixture, and the solvent was evaporated under reduced pressure. The system was adjusted to pH of about 9 with saturated aqueous $NaHCO_3$ solution, extracted with dichloromethane, and dried over anhydrous sodium sulfate to give the crude intermediate b6-2 (a pair of diastereoisomers).

Intermediate b6-2 (crude) and acetylacetone (10.6 mmol, 1.1 mL) were added to a reaction flask and dissolved with 30 mL of acetic acid. 3 mL of hydrobromic acid (45%) was slowly added to the mixture and the mixture was reacted at room temperature for 2 h. The reaction was stopped and the solvent was evaporated under reduced pressure to give the crude intermediate b6-3 (3.0 g, crude). LC-MS: $[M+H]^+$: 198.

The crude intermediate b6-3 (3.0 g), Boc anhydride (11.7 mmol, 2.5 g), triethylamine (23.4 mmol, 3.4 mL) and DMAP (0.78 mmol, 95 mg) were dissolved in 20 mL of tetrahydrofuran and the mixture was reacted at room temperature for 12 h. The reaction was stopped, and 100 mL of water was added. The mixture was extracted with ethyl acetate, washed with saturated aqueous sodium chloride solution, and dried over anhydrous sodium sulfate to give the product (2.4 g) as a yellow oil. The yellow oil was dissolved in 10 mL of DMF, and the mixture was placed in an ice bath. NBS (8.88 mmol, 1.58 g) was added slowly in batches, and the mixture was reacted at room temperature for 8 h. Then 50 mL of ice water was added. The mixture was extracted with ethyl acetate, dried over anhydrous sodium sulfate, and separated by flash column chromatography to give intermediate b6-4 (1.2 g, total yield for three steps: 35%) and intermediate b6-5 (600 mg, total yield for three steps: 17%). LC-MS: $[M+H]^+$: 377.

Intermediate b6-4 (1.25 mmol, 470 mg), bis(pinacolato) diboron (2.34 mmol, 595 mg), DIEA (2.5 mmol, 323 mg) and $Pd(Amphos)Cl_2$ (0.13 mmol, 90 mg) were added in a microwave reaction flask under nitrogen, and dissolved with 16 mL of a mixture of 2-methyl-tetrahydrofuran and methanol (v/v, 1/1). The mixture was heated to 100° C. by microwave and reacted for 1 h, and then the reaction was stopped. The mixture was filtered, and 30 mL of water was add. The mixture was extracted with ethyl acetate, and separated by flash column chromatography to give intermediate b6 (120 mg, yield: 23%). LC-MS: $[M+H]^+$: 424.

Referring to the synthesis of intermediate b6, intermediate b7 was synthesized by using b6-5 as raw material. LC-MS: $[M+H]^+$: 424.

Example 1

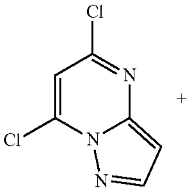

a1-1

-continued

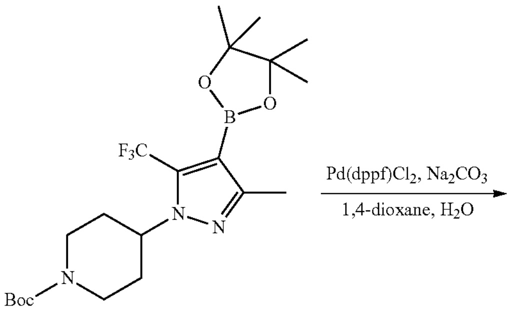

b1

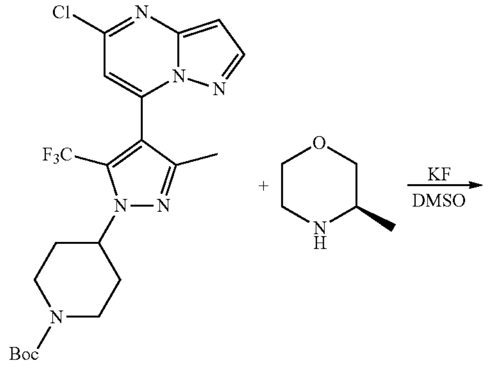

A1-1

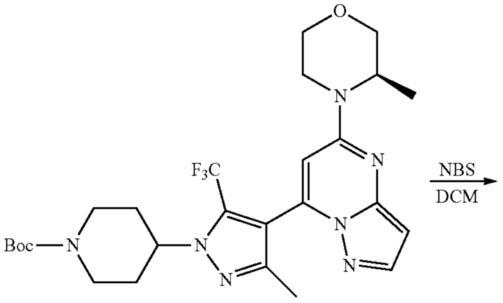

A1-2

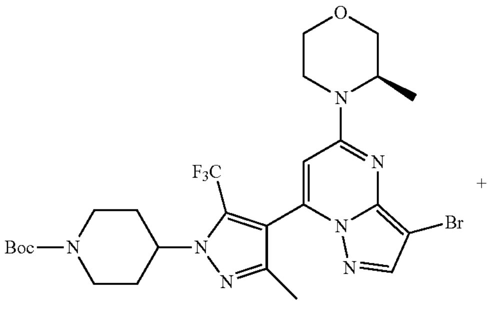

A1-3

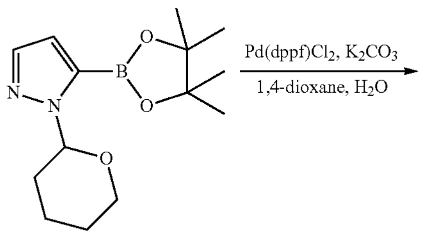

a3-2

-continued

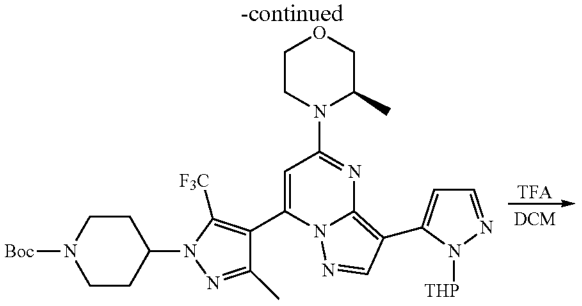

A1-4

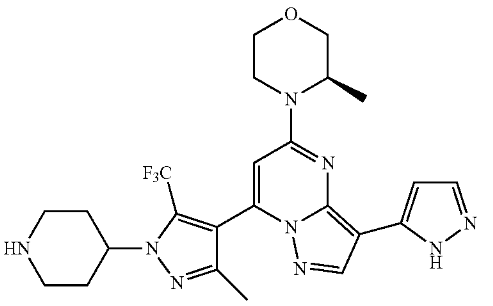

A1

The raw material a1-1 (1.06 mmol, 200 mg) and intermediate b1 (1.59 mmol, 730 mg) were dissolved in 10 mL of a mixture of 1,4-dioxane and water (v/v: 9/1) under nitrogen, and sodium carbonate (2.12 mmol, 225 mg) and Pd(dppf)$Cl_2$ (0.1 mmol, 73 mg) were added. The mixture was heated to 95° C. and reacted for 3 hours. The reaction was stopped. The mixture was filtered, and 40 mL of water was added to the system. The mixture was extracted with ethyl acetate, dried over anhydrous sodium sulfate, and separated by flash column chromatography to give compound A1-1 (330 mg, yield: 64%). LC-MS: $[M+H]^+$: 485.

Intermediate A1-1 (0.68 mmol, 330 mg) and (R)-2-methylmorpholine (1.36 mmol, 138 mg) were dissolved in 5 mL of DMSO, and KF (2.04 mmol, 118 mg) was added. The mixture was heated to 150° C. by microwave and reacted for 2 h. The reaction was stopped, and 30 mL of water was added. The mixture was extracted with dichloromethane, dried over anhydrous sodium sulfate, and separated by flash column chromatography to give compound A1-2 (220 mg, yield: 59%). LC-MS: $[M+H]^+$: 550.

Intermediate A1-2 (0.40 mmol, 220 mg) was dissolved in 5 mL of anhydrous dichloromethane in an ice bath and N-bromosuccinimide NBS (0.40 mmol, 72 mg) was slowly added in batches. The mixture was stirred for another 2 hours. The reaction was stopped, and 20 mL of saturated aqueous ammonium chloride solution was added. The mixture was extracted with dichloromethane, dried over anhydrous sodium sulfate, and separated by flash column chromatography to give compound A1-3 (140 mg, yield: 56%). LC-MS: $[M+H]^+$: 629.

Intermediate A1-3 (0.22 mmol, 140 mg) and the raw material a3-2 (0.33 mmol, 92 mg) were dissolved in 5 mL of a mixture of 1,4-dioxane and water (v/v: 9/1) under nitrogen, and potassium carbonate (0.44 mmol, 61 mg) and Pd(dppf)$Cl_2$ (0.02 mmol, 15 mg) were added. The mixture was heated to 95° C. and reacted for 2 hours. The reaction was stopped. The mixture was filtered, and 20 mL of water was added to the system. The mixture was extracted with ethyl acetate, dried over anhydrous sodium sulfate, and separated by flash column chromatography to give intermediate A1-4 (45 mg, yield: 29%). LC-MS: $[M+H]^+$: 700.

Intermediate A1-4 (45 mg) was dissolved in 5 mL of dichloromethane, and 3 mL of trifluoroacetic acid was added. The mixture was reacted at room temperature for 2 hours. The reaction was stopped, and the solvent was evaporated under reduced pressure. Saturated aqueous sodium bicarbonate solution was added to adjust the pH to 10. The mixture was extracted with dichloromethane, and separated by preparative chromatography to give the target compound A1 (8 mg, yield: 24%), LC-MS: $[M+H]^+$: 516.

The following compounds were synthesized with reference to the route of Example 1.

| Structure | Structure of intermediate replacing b1 | LC-MS/ $[M + H]^+$ | $^1$H NMR |
|---|---|---|---|
| 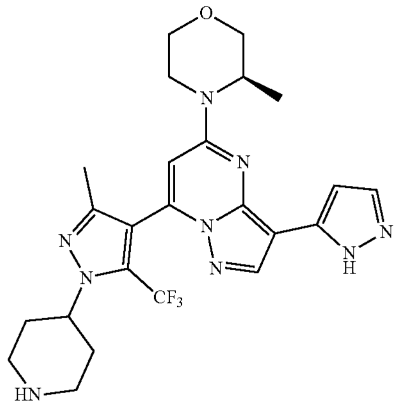 A1 | — | 516 | (TFA salt); $^1$H NMR (400 MHz, DMSO-$d_6$) δ 12.70 (d, J = 79.1 Hz, 1H), 8.21 (s, 1H), 7.61 (d, J = 83.1 Hz, 1H), 6.91 (s, 1H), 6.72 (d, J = 53.9 Hz, 1H), 4.53 (s, 1H), 4.28 (d, J = 9.5 Hz, 2H), 3.99 (d, J = 11.2 Hz, 1H), 3.76 (d, J = 11.4 Hz, 1H), 3.67 (d, J = 10.6 Hz, 1H), 3.52 (t, J = 11.9 Hz, 1H), 3.27-3.19 (m, 1H), 3.08 (s, 2H), 2.61 (dt, J = 10.1, 6.3 Hz, 2H), 2.16 (d, J = 4.1 Hz, 3H), 2.06-1.98 (m, 2H), 1.86 (dd, J = 26.0, 11.9 Hz, 2H), 1.26 (d, J = 6.1 Hz, 3H). |

-continued
| Structure | Structure of intermediate replacing b1 | LC-MS/ $[M + H]^+$ | $^1H$ NMR |
|---|---|---|---|
| 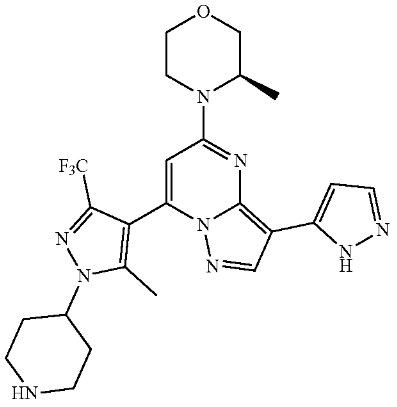 A2 | 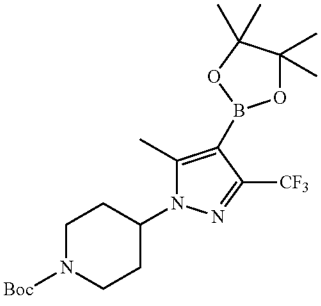 b2 | 516 | (TFA salt); $^1H$ NMR (400 MHz, DMSO-$d_6$) δ 8.72 (d, J = 10.7 Hz, 1H), 8.39 (s, 1H), 8.22 (s, 1H), 7.62 (s, 1H), 6.79-6.73 (m, 2H), 4.79 (s, 1H), 4.49 (s, 1H), 4.23 (d, J = 13.6 Hz, 1H), 4.03-3.98 (m, 1H), 3.77 (d, J = 11.5 Hz, 1H), 3.67 (dd, J = 11.6, 3.1 Hz, 1H), 3.56-3.46 (m, 3H), 3.30-3.22 (m, 1H), 3.17-3.08 (m, 2H), 2.32-2.30 (s, 3H), 2.17 (d, J = 33.6 Hz, 3H), 2.00 (q, J = 7.2, 6.8 Hz, 1H), 1.26 (s, 3H). |
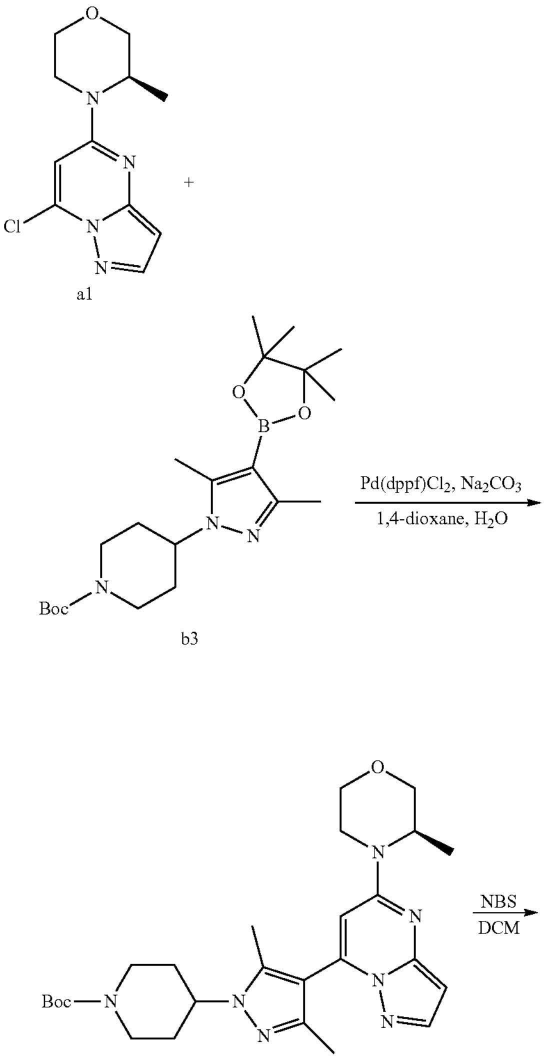
a1
b3
A3-1
-continued
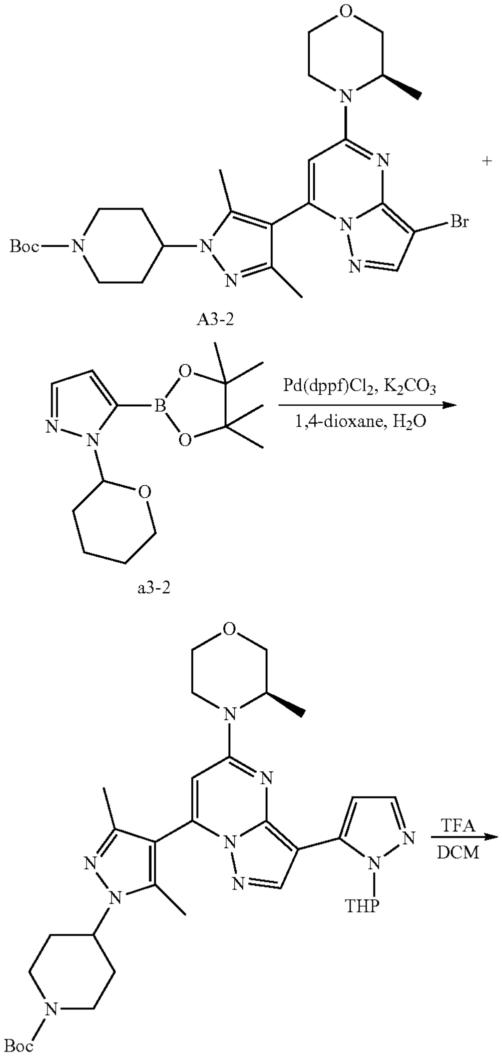
A3-2
a3-2
A3-3

-continued

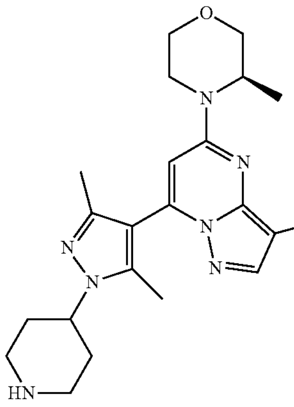

A3

Intermediate at (0.79 mmol, 200 mg) and intermediate b3 (1.19 mmol, crude) were dissolved in 10 mL of a mixture of 1,4-dioxane and water (v/v: 9/1) under nitrogen, and sodium carbonate (1.60 mmol, 170 mg) and $Pd(dppf)Cl_2$ (0.08 mmol, 59 mg) were added. The mixture was heated to 95° C. and reacted for 10 hours. The reaction was stopped. The mixture was filtered, and 40 mL of water was added to the system. The mixture was extracted with ethyl acetate, dried over anhydrous sodium sulfate, and separated by flash column chromatography to give compound A3-1 (230 mg, yield: 59%). LC-MS: $[M+H]^+$: 496.

Intermediate A3-1 (0.46 mmol, 230 mg) was dissolved in 15 mL of anhydrous dichloromethane in an ice bath and N-bromosuccinimide NBS (0.51 mmol, 90 mg) was slowly added in batches. The mixture was stirred for another 2 hours. The reaction was stopped, and 30 mL of saturated aqueous ammonium chloride solution was added. The mixture was extracted with dichloromethane, dried over anhydrous sodium sulfate, and separated by flash column chromatography to give compound A3-2 (220 mg, yield: 83%). LC-MS: $[M+H]^+$: 575.

Intermediate A3-2 (0.38 mmol, 220 mg) and the raw material a3-2 (0.76 mmol, 211 mg) were dissolved in 10 mL of a mixture of 1,4-dioxane and water (v/v: 9/1) under nitrogen, and potassium carbonate (0.76 mmol, 105 mg) and $Pd(dppf)Cl_2$ (0.038 mmol, 28 mg) were added. The mixture was heated to 100° C. by microwave and reacted for 2 hours. The reaction was stopped. The mixture was filtered, and 30 mL of water was added to the system. The mixture was extracted with ethyl acetate, dried over anhydrous sodium sulfate, and separated by flash column chromatography to give compound A3-3 (100 mg, yield: 41%). LC-MS: $[M+H]^+$: 646.

Intermediate A3-3 (100 mg) was dissolved in 6 mL of dichloromethane, and 3 mL of trifluoroacetic acid was added. The mixture was reacted at room temperature for 2 hours. The reaction was stopped, and the solvent was evaporated under reduced pressure. Saturated aqueous sodium bicarbonate solution was added to adjust the pH to 10. The mixture was extracted with dichloromethane, and separated by preparative chromatography to give the target compound A3 (25 mg, yield: 35%), LC-MS: $[M+H]^+$: 462.

The following compounds were synthesized with reference to the route of Example 2:

| Structure | Structure of intermediate replacing b3 | LC-MS/ $[M + H]^+$ | $^1H$ NMR |
|---|---|---|---|
| 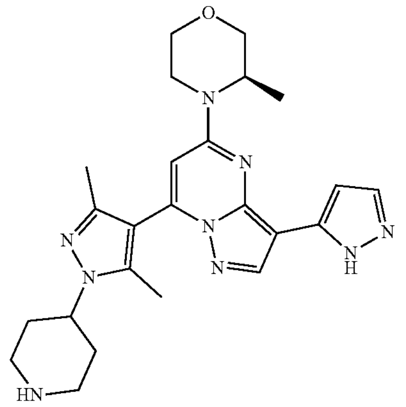 A3 | — | 462 | (TFA salt); $^1H$ NMR (600 MHz, DMSO-$d_6$) δ 8.71 (d, J = 11.0 Hz, 1H), 8.40 (d, J = 11.2 Hz, 1H), 8.24 (s, 1H), 7.62 (s, 1H), 6.76 (d, J = 1.9 Hz, 1H), 6.63 (s, 1H), 4.56 (m, 1H), 4.25 (d, J = 13.4 Hz, 1H), 4.00 (dd, J = 11.5, 3.8 Hz, 1H), 3.77 (d, J = 11.4 Hz, 1H), 3.66 (dd, J = 11.6, 3.1 Hz, 1H), 3.58-3.48 (m, 1H), 3.46 (d, J = 12.4 Hz, 1H), 3.24 (m, 2H), 3.17-3.07 (m, 3H), 2.27 (s, 3H), 2.26-2.21 (m, 2H), 2.15 (s, 3H), 2.04 (d, J = 13.0 Hz, 2H), 1.26 (d, J = 6.7 Hz, 3H). |
| 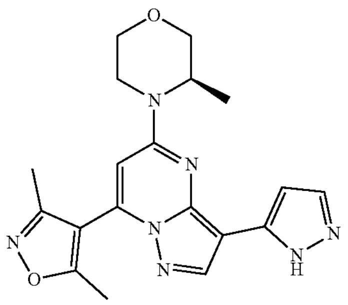 A4 | 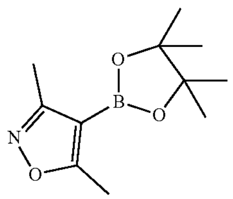 [SMILES: Cc1noc(C)c1B1OC(C)(C)C(C)(C)O1] | 380 | (Free base); $^1H$ NMR (400 MHz, DMSO-$d_6$) δ 8.29 (s, 1H), 7.62 (s, 1H), 6.87 (s, 1H), 6.77 (s, 1H), 4.58 (s, 1H), 4.32-4.23 (m, 1H), 4.03 (dd, J = 11.4, 3.6 Hz, 1H), 3.80 (d, J = 11.5 Hz, 1H), 3.69 (dd, J = 11.5, 3.0 Hz, 1H), 3.54 (td, J = 11.9, 2.9 Hz, 1H), 3.27 (dd, J = 12.7, 3.8 Hz, 1H), 2.48 (s, 3H), 2.26 (s, 3H), 1.30 (d, J = 6.7 Hz, 3H). |

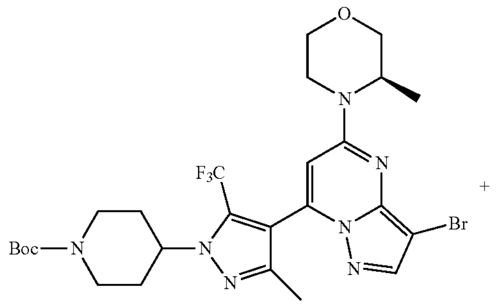

A1-3

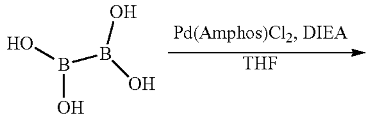

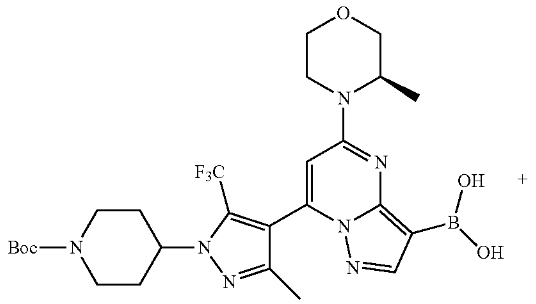

A5-1

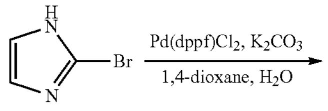

A5-2

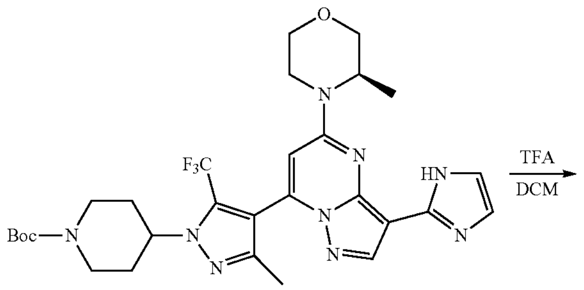

A5-3

-continued

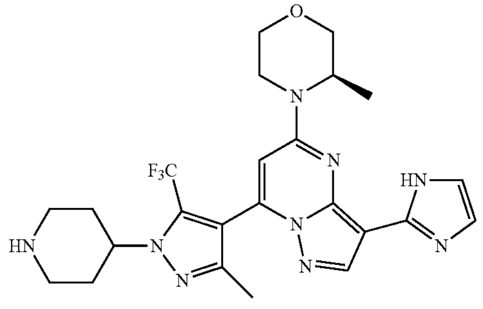

A5

Intermediate A1-3 (0.32 mmol, 200 mg) and the raw material tetrahydroxydiboron (0.64 mmol, 58 mg) were dissolved in 10 mL of anhydrous tetrahydrofuran under nitrogen, and DIEA (0.64 mmol, 83 mg) and Pd(Amphos) $Cl_2$ (0.03 mmol, 21 mg) were added. The mixture was heated to 95° C. by microwave and reacted for 2 hours. The reaction was stopped. The mixture was filtered, and 30 mL of water was added to the system. The mixture was extracted with ethyl acetate, and dried over anhydrous sodium sulfate to give the crude compound A5-1, which was used directly in the next reaction step. LC-MS: $[M+H]^+$: 594.

The crude intermediate A5-1 (150 mg, crude) from the previous step and 2-bromoimidazole A5-2 (0.25 mmol, 37 mg) were dissolved in 10 mL of a mixture of 1,4-dioxane and water (v/v: 9/1) under nitrogen, and potassium carbonate (0.5 mmol, 69 mg) and Pd(dppf)$Cl_2$ (0.025 mmol, 19 mg) were added. The mixture was heated to 110° C. by microwave and reacted for 2 hours. The reaction was stopped. The mixture was filtered, and 30 mL of water was added to the system. The mixture was extracted with ethyl acetate, dried over anhydrous sodium sulfate, and separated by flash column chromatography to give compound A5-3 (70 mg, total yield for two steps: 36%). LC-MS: $[M+H]^+$: 616.

Intermediate A5-3 (70 mg) was dissolved in 4 mL of dichloromethane, and 2 mL of trifluoroacetic acid was added. The mixture was reacted at room temperature for 2 hours. The reaction was stopped, and the solvent was evaporated under reduced pressure. Saturated aqueous sodium bicarbonate solution was added to adjust the pH to 10. The mixture was extracted with dichloromethane, and separated by preparative chromatography to give the target compound A5 (30 mg, yield: 53%), LC-MS: $[M+H]^+$: 516.

The following compounds were synthesized with reference to the route of Example 3:

| Structure | Structure of intermediate replacing A5-2 | LC-MS/ $[M + H]^+$ | $^1$H NMR |
|---|---|---|---|
| 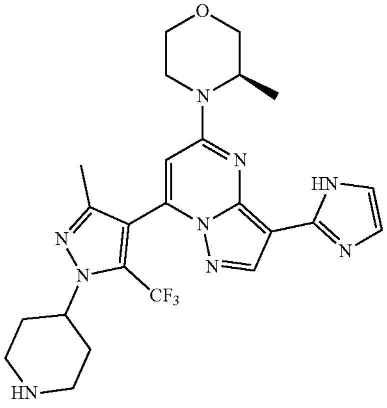 A5 | — | 516 | (TFA salt); $^1$H NMR (400 MHz, DMSO-$d_6$) δ 13.60 (s, 2H), 8.98 (s, 1H), 8.60 (s, 1H), 8.50 (s, 1H), 7.67 (s, 2H), 7.16 (d, J = 6.5 Hz, 1H), 4.80-4.68 (m, 2H), 4.02 (d, J = 12.4 Hz, 1H), 3.79 (d, J = 11.7 Hz, 1H), 3.68 (d, J = 15.7 Hz, 1H), 3.59-3.39 (m, 4H), 3.32-3.17 (m, 3H), 2.45-2.32 (m, 2H), 2.20 (d, J = 2.5 Hz, 3H), 2.12 (m, 2H), 1.27 (d, J = 6.7 Hz, 3H). |
| 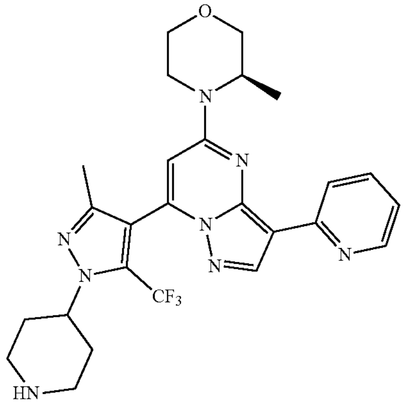 A6 | 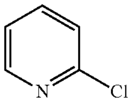 | 527 | (Free base); $^1$H NMR (400 MHz, DMSO-$d_6$) δ 8.87 (d, J = 11.6 Hz, 1H), 8.66-8.56 (m, 2H), 8.18 (s, 1H), 7.41 (s, 1H), 7.10 (d, J = 5.3 Hz, 1H), 4.81-4.68 (m, 2H), 4.58 (s, 1H), 4.34 (d, J = 15.3 Hz, 1H), 4.03 (d, J = 12.2 Hz, 1H), 3.80 (d, J = 11.4 Hz, 1H), 3.74-3.66 (m, 1H), 3.60-3.43 (m, 3H), 3.32 (s, 1H), 3.22 (d, J = 12.9 Hz, 1H), 2.41-2.30 (m, 2H), 2.20 (d, J = 2.8 Hz, 3H), 2.09 (d, J = 12.6 Hz, 1H), 2.02-1.94 (m, 1H), 1.35-1.25 (m, 3H). |
Example 4
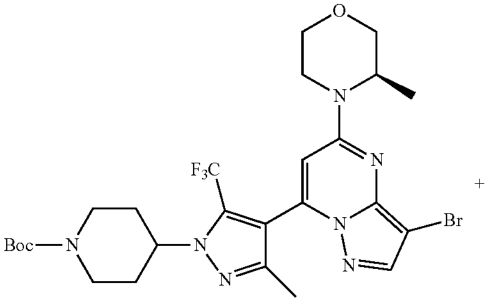
A1-3
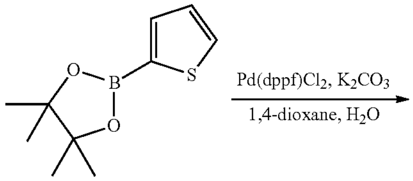
A7-1
-continued
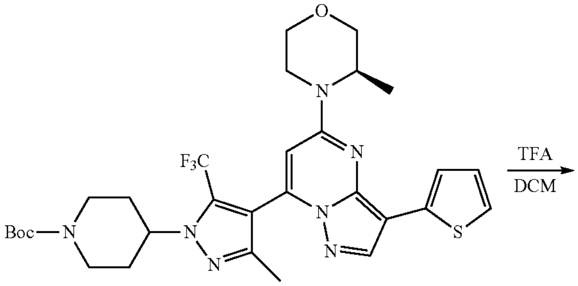
A7-2
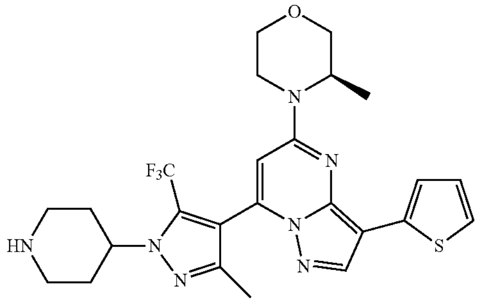
A7

Intermediate A1-3 (0.29 mmol, 180 mg) and thiophene-2-boronic acid pinacol ester A7-1 (0.58 mmol, 121 mg) were dissolved in 10 mL of a mixture of 1,4-dioxane and water (v/v: 9/1) under nitrogen, and potassium carbonate (0.87 mmol, 120 mg) and $Pd(dppf)Cl_2$ (0.03 mmol, 22 mg) were added. The mixture was heated to 95° C. and reacted for 2 hours. The reaction was stopped. The mixture was filtered, and the solvent was evaporated under reduced pressure. 30 mL of water was added. The mixture was extracted with ethyl acetate, and separated by flash column chromatography to give compound A7-2 (100 mg, yield: 55%), LC-MS: $[M+H]^+$: 632.

Intermediate A7-2 (100 mg) was dissolved in 5 mL of dichloromethane, and 2 mL of trifluoroacetic acid was added. The mixture was reacted at room temperature for 2 hours. The reaction was stopped, and the solvent was evaporated under reduced pressure. Saturated aqueous sodium bicarbonate solution was added to adjust the pH to 10. The mixture was extracted with dichloromethane, and separated by preparative chromatography to give the target compound A7 (20 mg, yield: 25%), LC-MS: $[M+H]^+$: 532.

(TFA salt); H NMR (600 MHz, DMSO-d) δ 8.83 (s, 1H), 8.44 (s, 1H), 8.27 (d, J=11.8 Hz, 1H), 7.44 (t, J=7.4 Hz, 1H), 7.35 (m, 1H), 7.08 (m, 1H), 6.94 (m, 1H), 4.73 (s, 1H), 4.54 (s, 1H), 4.25 (d, J=13.8 Hz, 1H), 4.01 (m, 1H), 3.78 (m, 1H), 3.68 (s, 1H), 3.59-3.53 (m, 1H), 3.45 (d, J=12.5 Hz, 2H), 3.26 (M, 3H), 2.42-2.30 (m, 2H), 2.23-1.97 (i, 5H), 1.28 (d, J=6.9 Hz, 3H).

Example 5

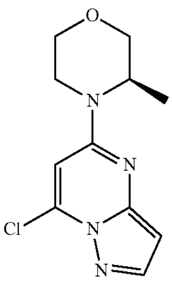

a1

+

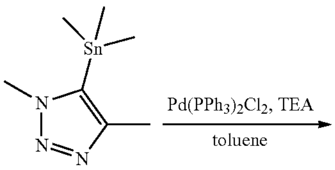

b4

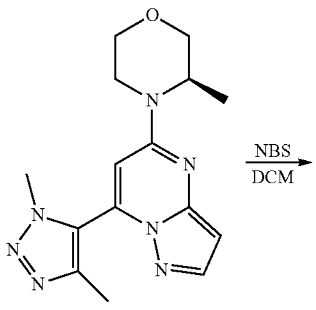

A8-1

-continued

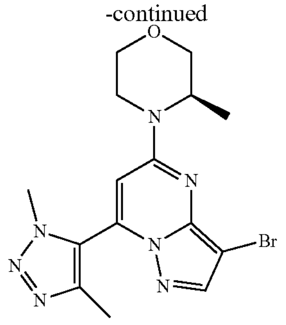

+

A8-2

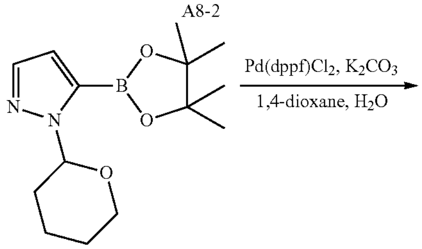

a3-2

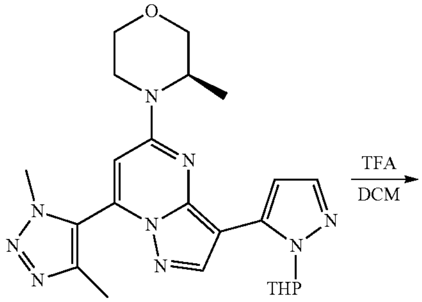

A8-3

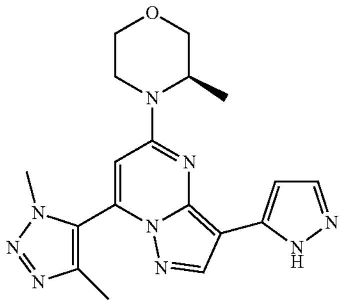

A8

Intermediate at (0.59 mmol, 150 mg) and intermediate b4 (1.54 mmol, crude) were dissolved in 10 mL of toluene under nitrogen, and triethylamine (1.19 mmol, 120 mg) and $Pd(PPh_3)_2Cl_2$ (0.12 mmol, 84 mg) were added. The mixture was heated to 100° C. and reacted for 3 hours. The reaction was stopped. The mixture was filtered, and 30 mL of water was added to the system. The mixture was extracted with ethyl acetate, dried over anhydrous sodium sulfate, and separated by TLC chromatography to give compound A8-1 (120 mg, yield: 65%). LC-MS: $[M+H]^+$: 314.

Intermediate A8-1 (0.38 mmol, 120 mg) was dissolved in 8 mL of anhydrous dichloromethane in an ice bath and N-bromosuccinimide NBS (0.42 mmol, 75 mg) was slowly added in batches. The mixture was stirred at room temperature for 2 hours. The reaction was stopped, and 20 mL of saturated aqueous ammonium chloride solution was added. The mixture was extracted with dichloromethane, and dried over anhydrous sodium sulfate to give compound A8-2 (200 mg, crude). LC-MS: $[M+H]^+$: 393.

The crude intermediate A8-2 (200 mg) from the previous step and the raw material a3-2 (0.57 mmol, 158 mg) were dissolved in 10 mL of a mixture of 1,4-dioxane and water (v/v: 9/1) under nitrogen, and potassium carbonate (0.76 mmol, 105 mg) and $Pd(dppf)Cl_2$ (0.04 mmol, 29 mg) were added. The mixture was heated to 100° C. by microwave and reacted for 2 hours. The reaction was stopped. The mixture was filtered, and 40 mL of water was added to the system. The mixture was extracted with ethyl acetate, dried over anhydrous sodium sulfate, and separated by TLC chromatography to give compound A8-3 (80 mg, total yield for two steps: 46%). LC-MS: $[M+H]^+$: 464.

Intermediate A8-3 (80 mg) was dissolved in 5 mL of dichloromethane, and 2 mL of trifluoroacetic acid was added. The mixture was reacted at room temperature for 2 hours. The reaction was stopped, and the solvent was evaporated under reduced pressure. Saturated aqueous sodium bicarbonate solution was added to adjust the pH to 10. The mixture was extracted with dichloromethane, and separated by preparative chromatography to give the target compound A8 (27 mg, yield: 42%), LC-MS: $[M+H]^+$: 380.

(TFA salt); $^1H$ NMR (400 MHz, DMSO-$d_6$) δ 8.30 (s, 1H), 7.67 (d, J=1.8 Hz, 1H), 7.05 (s, 1H), 6.79 (d, J=2.0 Hz, 1H), 4.57 (d, J=6.6 Hz, 1H), 4.28 (d, J=13.2 Hz, 1H), 4.02 (d, J=3.4 Hz, 1H), 3.99 (s, 3H), 3.79 (d, J=11.4 Hz, 1H), 3.67 (dd, J=11.8, 2.9 Hz, 1H), 3.52 (td, J=11.8, 2.9 Hz, 1H), 3.33-3.23 (m, 1H), 2.27 (s, 3H), 1.29 (d, J=6.7 Hz, 3H).

Example 6

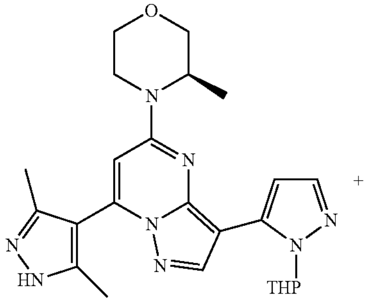

a3

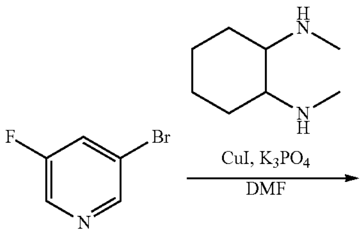

A9-1

-continued

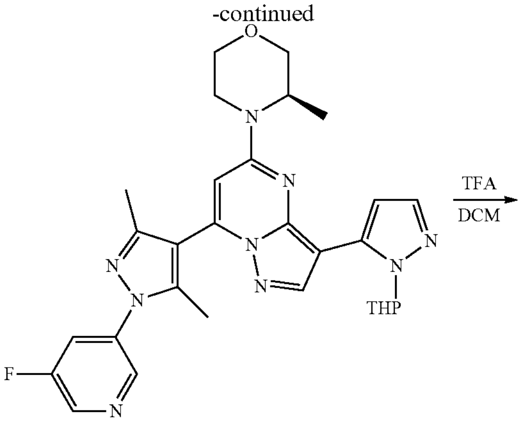

A9-2

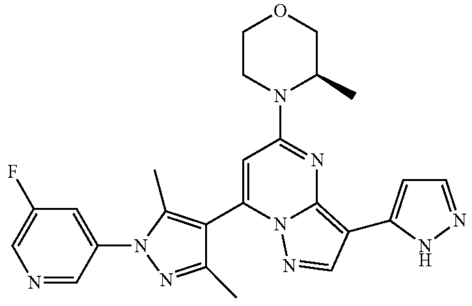

A9

Intermediate a3 (0.17 mmol, 80 mg), 3-bromo-5-fluoropyridine A9-1 (0.34 mmol, 60 mg), potassium phosphate (0.34 mmol, 72 mg) and CuI (0.034 mmol, 7 mg) were added to a microwave reaction flask under nitrogen, and dissolved with 5 mL of DMF. The mixture was stirred for 5 min, and then N,N-dimethyl-1,2-cyclohexanediamine (0.07 mmol, 10 mg) was slowly added. The mixture was heated to 110° C. by microwave and reacted for 1.5 h. The reaction was stopped. 40 mL of water was added. The mixture was extracted with ethyl acetate, dried over anhydrous $Na_2SO_4$, and separated by flash column chromatography to give compound A9-2 (50 mg, yield: 53%), LC-MS: $[M+H]^+$: 558.

Intermediate A9-2 (50 mg) was dissolved in 4 mL of dichloromethane, and 2 mL of trifluoroacetic acid was added. The mixture was reacted at room temperature for 2 hours. The reaction was stopped, and the solvent was evaporated under reduced pressure. Saturated aqueous sodium bicarbonate solution was added to adjust the pH to 10. The mixture was extracted with dichloromethane, and separated by preparative chromatography to give the target compound A9 (28 mg, yield: 67%), LC-MS: $[M+H]^+$: 474.

The Following Compounds were Synthesized with Reference to the Route of Example 6

| Structure | Structure of intermediate replacing A9-1 | LC-MS/ [M + H]+ | $^1$H NMR |
|---|---|---|---|
| 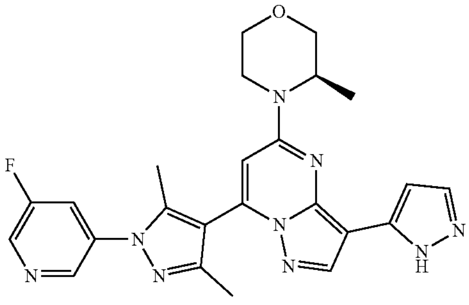 A9 | — | 474 | (Free base); $^1$H NMR (400 MHz, DMSO-$d_6$) δ 8.77-8.75 (m, 1H), 8.72 (dd, J = 2.6, 0.3 Hz, 1H), 8.30 (s, 1H), 8.12 (m, 1H), 7.63 (d, J = 94.4 Hz, 1H), 6.76 (br, 2H), 4.55 (s, 1H), 4.26 (s, 1H), 4.01 (dd, J = 11.5, 4.2 Hz, 1H), 3.79 (d, J = 11.6 Hz, 1H), 3.70 (d, J = 2.8 Hz, 1H), 3.53 (td, J = 11.6, 2.9 Hz, 1H), 3.30-3.22 (m, 1H), 2.38 (s, 3H), 2.24 (s, 3H), 1.29 (d, J = 6.7 Hz, 3H). |
| 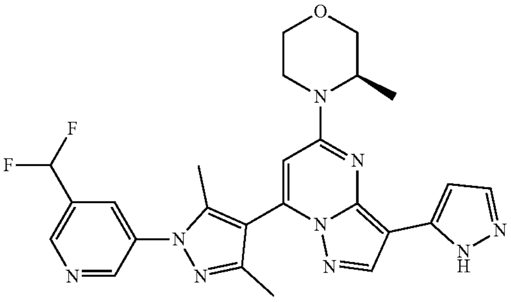 A10 | 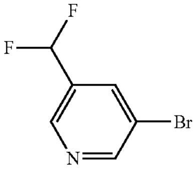 | 506 | (Free base); $^1$H NMR (400 MHz, DMSO-$d_6$) δ 9.05 (d, J = 2.4 Hz, 1H), 8.90 (q, J = 1.6 Hz, 1H), 8.28 (d, J = 5.7 Hz, 2H), 7.63 (s, 1H), 7.29 (t, $J_{C-F}$ = 108 Hz, 1H), 6.78 (s, 2H), 4.55 (s, 1H), 4.28 (d, J = 13.5 Hz, 1H), 4.02 (d, J = 9.9 Hz, 1H), 3.79 (d, J = 11.5 Hz, 1H), 3.69 (dd, J = 11.5, 3.1 Hz, 1H), 3.57-3.50 (m, 1H), 3.27 (m, 1H), 2.40 (s, 3H), 2.26 (s, 3H), 1.29 (d, J = 6.6 Hz, 3H). |
| 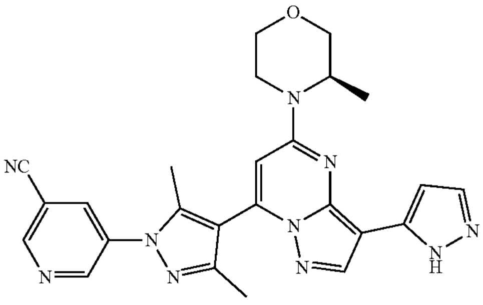 A11 | 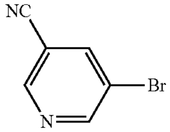 | 481 | (Free base); $^1$H NMR (400 MHz, DMSO-$d_6$) δ 9.14 (dd, J = 12.2, 2.2 Hz, 2H), 8.66 (t, J = 2.1 Hz, 1H), 8.28 (s, 1H), 7.63 (s, 1H), 6.78 (d, J = 1.9 Hz, 1H), 6.76 (s, 1H), 4.56 (s, 1H), 4.28 (d, J = 13.7 Hz, 1H), 4.04-3.98 (m, 1H), 3.79 (d, J = 11.4 Hz, 1H), 3.70-3.66 (m, 1H), 3.54 (dd, J = 13.1, 10.0 Hz, 1H), 3.32-3.22 (m, 1H), 2.40 (s, 3H), 2.25 (s, 3H), 1.29 (d, J = 6.7 Hz, 3H). |
| 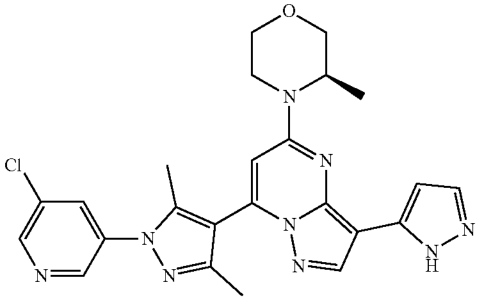 A12 | 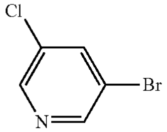 | 490 | (Free base); $^1$H NMR (400 MHz, DMSO-$d_6$) δ 8.84 (d, J = 2.1 Hz, 1H), 8.75 (d, J = 2.2 Hz, 1H), 8.28 (t, J = 2.2 Hz, 1H), 7.75 (s, 1H), 7.52 (s, 1H), 6.73 (m, 2H), 4.55 (s, 1H), 4.27 (s, 1H), 4.01 (dd, J = 11.4, 3.6 Hz, 1H), 3.79 (d, J = 11.4 Hz, 1H), 3.69 (dd, J = 11.4, 3.0 Hz, 1H), 3.54 (dd, J = 12.6, 9.6 Hz, 1H), 3.25 (dd, J = 12.7, 3.9 Hz, 1H), 2.39 (s, 3H), 2.24 (s, 3H), 1.29 (d, J = 6.7 Hz, 3H). |

-continued

| Structure | Structure of intermediate replacing A9-1 | LC-MS/ [M + H]+ | 1H NMR |
|---|---|---|---|
| 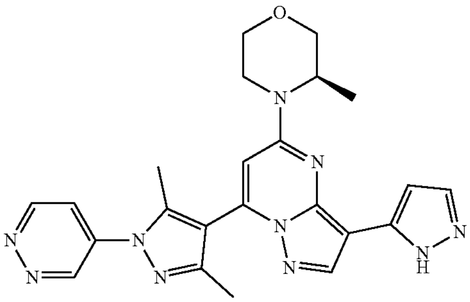 A13 | 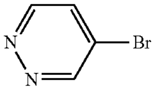 | 457 | (Free base); 1H NMR (400 MHz, DMSO-$d_6$) δ 9.67 (d, J = 2.7 Hz, 1H), 9.38 (d, J = 5.7 Hz, 1H), 8.28 (s, 1H), 8.01 (dd, J = 5.8, 2.8 Hz, 1H), 7.61 (s, 1H), 6.80 (s, 1H), 6.77 (s, 1H), 4.55 (s, 1H), 4.27 (d, J = 13.4 Hz, 1H), 4.01 (d, J = 9.4 Hz, 1H), 3.79 (d, J = 11.4 Hz, 1H), 3.69 (dd, J = 12.0, 3.0 Hz, 1H), 3.54 (t, J = 11.5 Hz, 1H), 3.29 (d, J = 10.9 Hz, 1H), 2.5 (s, 3H. in DMSO), 2.26 (s, 3H), 1.29 (d, J = 6.7 Hz, 3H). |
| 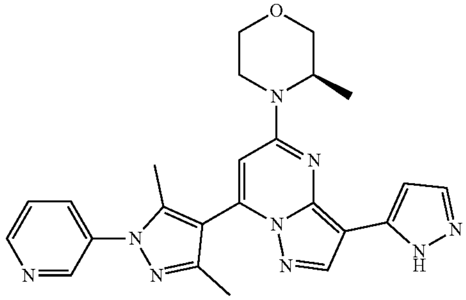 A22 | 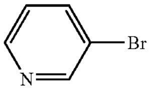 | 456 | (Free base); 1H NMR (400 MHz, DMSO-$d_6$) δ 12.70 (s, 1H), 8.84 (d, J = 2.7 Hz, 1H), 8.68 (d, J = 4.8 Hz, 1H), 8.28 (s, 1H), 8.06 (m, 1H), 7.63 (dd, J = 8.3, 4.8 Hz, 2H), 6.77 (s, 2H), 4.56 (d, J = 8.3 Hz, 1H), 4.32-4.24 (m, 1H), 4.01 (dd, J = 11.4, 3.6 Hz, 1H), 3.79 (d, J = 11.4 Hz, 1H), 3.69 (dd, J = 11.4, 3.1 Hz, 1H), 3.54 (td, J = 11.9, 3.1 Hz, 1H), 3.25 (m, 1H), 2.34 (s, 3H), 2.24 (s, 3H), 1.29 (d, J = 6.7 Hz, 3H). |
| 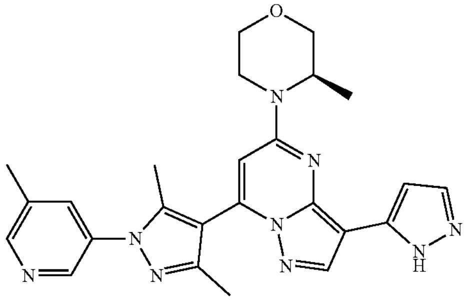 A23 | 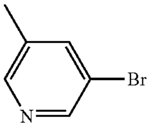 | 470 | (Free base); 1H NMR (400 MHz, DMSO-$d_6$) δ 8.63 (d, J = 2.5 Hz, 1H), 8.52 (s, 1H), 8.28 (s, 1H), 7.89 (d, J = 2.3 Hz, 1H), 7.61 (s, 1H), 6.77 (d, J = 2.9 Hz, 2H), 4.56 (d, J = 7.8 Hz, 1H), 4.28 (d, J = 13.3 Hz, 1H), 4.01 (dd, J = 11.4, 3.6 Hz, 1H), 3.79 (d, J = 11.4 Hz, 1H), 3.69 (dd, J = 11.5, 3.1 Hz, 1H), 3.54 (m, 1H), 3.27 (m, 1H), 2.43 (s, 3H), 2.33 (s, 3H), 2.24 (s, 3H), 1.29 (d, J = 6.7 Hz, 3H). |
| 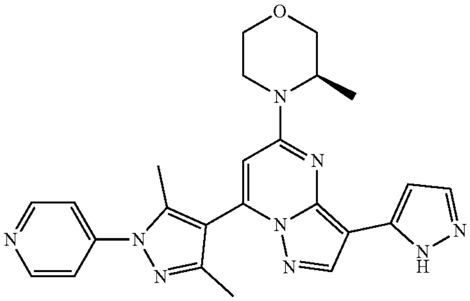 A24 | 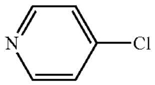 | 456 | (Free base); 1H NMR (400 MHz, DMSO-$d_6$) δ 12.69 (s, 1H), 8.77-8.71 (m, 2H), 8.27 (s, 1H), 7.72-7.69 (m, 2H), 7.61 (s, 1H), 6.79 (s, 1H), 6.78-6.73 (m, 1H), 4.56 (d, J = 7.7 Hz, 1H), 4.27 (d, J = 13.5 Hz, 1H), 4.01 (dd, J = 11.6, 3.6 Hz, 1H), 3.79 (d, J = 11.4 Hz, 1H), 3.69 (dd, J = 11.4, 3.1 Hz, 1H), 3.54 (m, 1H), 3.25 (m, 1H), 2.44 (s, 3H), 2.24 (s, 3H), 1.29 (d, J = 6.7 Hz, 3H). |

Example 7

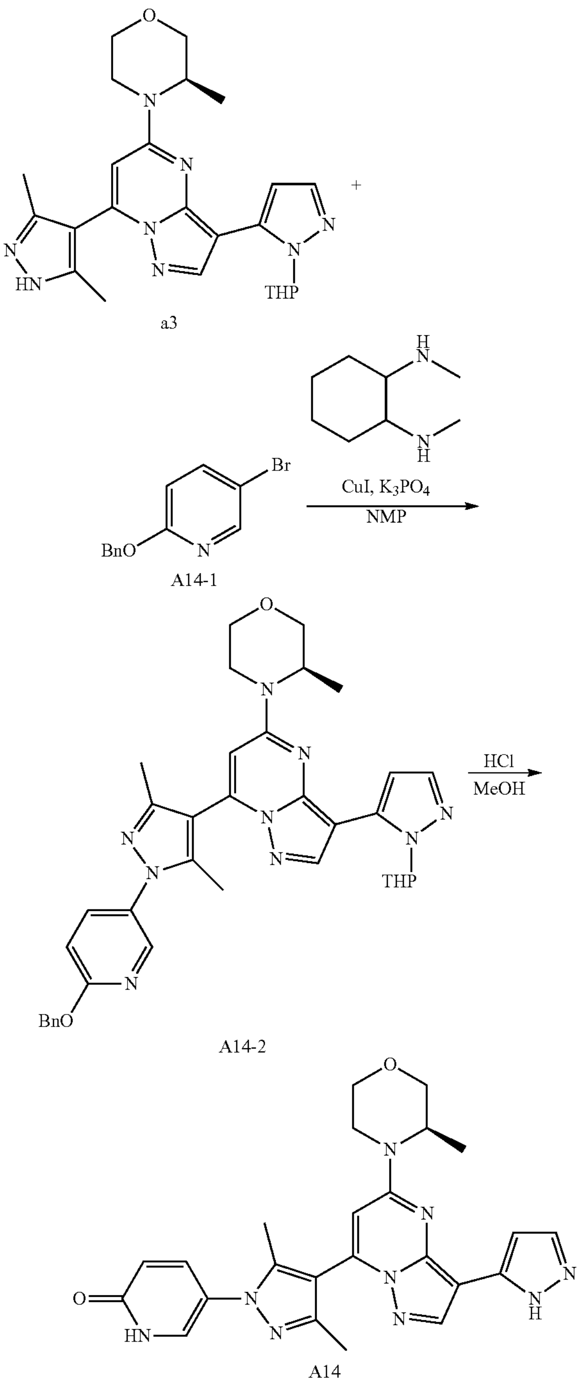

a3, A14-1, A14-2, A14

Intermediate a3 (0.15 mmol, 70 mg), 3-bromo-6-benzyloxy-pyridine A14-1 (0.30 mmol, 79 mg), potassium phosphate (0.45 mmol, 95 mg) and CuI (0.02 mmol, 4 mg) were added to a microwave reaction flask under nitrogen, and dissolved with 5 mL of N-methyl-pyrrolidone. The mixture was stirred for 5 min, and then N,N-dimethyl-1,2-cyclohexanediamine (0.03 mmol, 4.3 mg) was slowly added. The mixture was heated to 110° C. by microwave and reacted for 10 h. The reaction was then stopped. 20 mL of water was added. The mixture was extracted with ethyl acetate, dried over anhydrous sodium sulfate, and separated by TLC chromatography to give compound A14-2 (70 mg, yield: 73%), LC-MS: $[M+H]^+$: 646.

Intermediate A14-2 (70 mg) was dissolved in 5 mL of methanol, and 3 mL of concentrated hydrochloric acid was added. The mixture was heated to 65° C. and reacted for 2 hours. The reaction was stopped. The reaction solution was placed in an ice bath and saturated aqueous $NaHCO_3$ solution was slowly added to the system. The mixture was extracted with ethyl acetate, dried over anhydrous sodium sulfate, and separated by preparative chromatography to give the target compound A14 (20 mg, yield: 39%), LC-MS: $[M+H]^+$: 472.

(Free base); $^1H$ NMR (400 MHz, DMSO-$d_6$) δ 8.27 (s, 1H), 7.74 (d, J=2.9 Hz, 1H), 7.62 (dd, J=9.5, 3.0 Hz, 2H), 6.77 (d, J=1.9 Hz, 1H), 6.69 (s, 1H), 6.49 (d, J=9.6 Hz, 1H), 4.54 (s, 1H), 4.26 (d, J=13.5 Hz, 1H), 4.03-3.98 (m, 1H), 3.78 (d, J=11.4 Hz, 1H), 3.68 (dd, J=11.6, 3.1 Hz, 1H), 3.57-3.49 (m, 1H), 3.30-3.22 (m, 1H), 2.24 (s, 3H), 2.20 (s, 3H), 1.28 (d, J=6.6 Hz, 3H).

Example 8

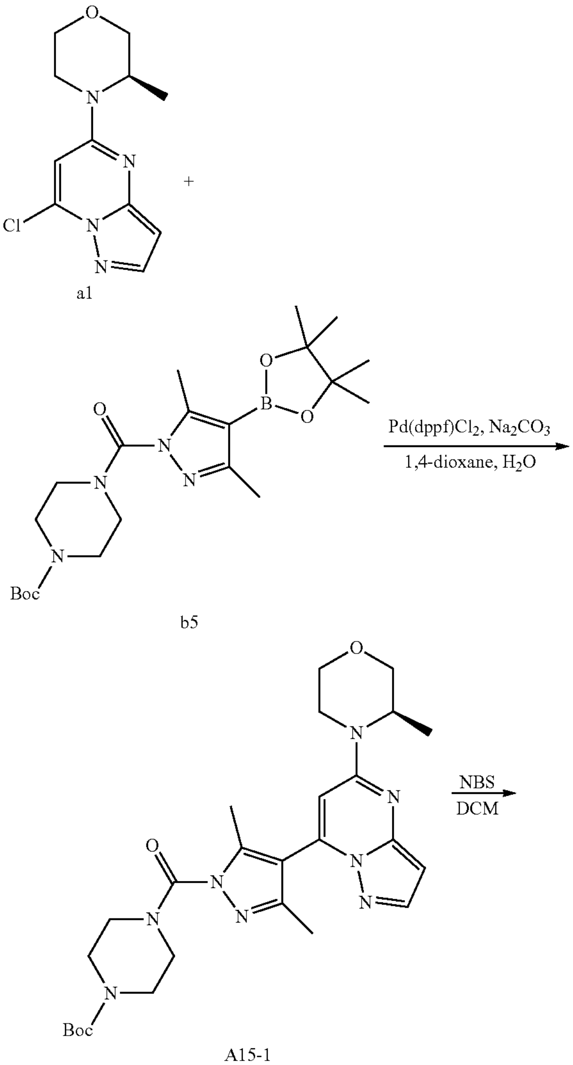

a1, b5, A15-1

-continued

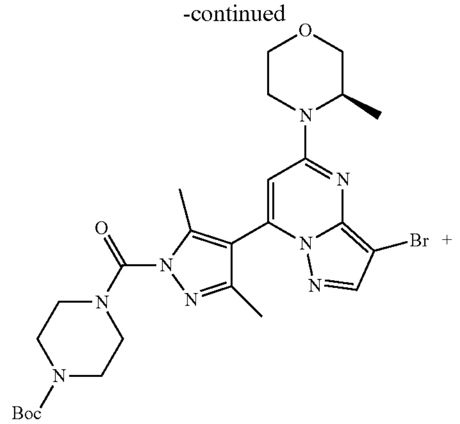

A15-2

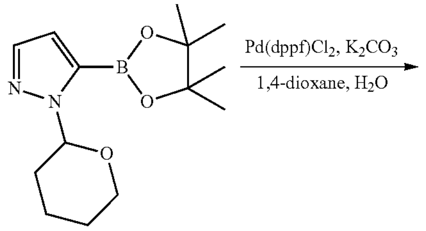

a3-2

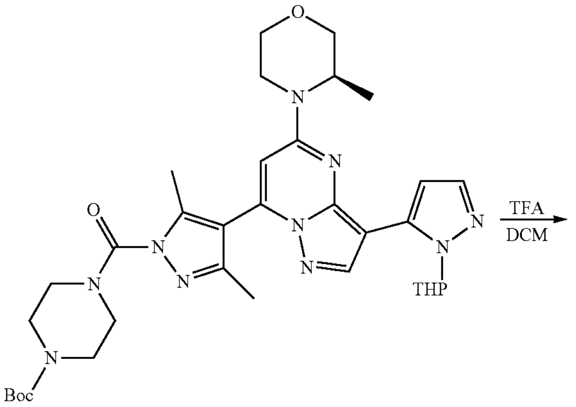

A15-3

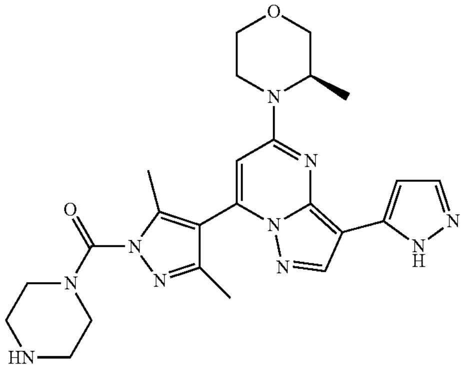

A15

Intermediate a1 (0.79 mmol, 200 mg) and intermediate b5 (1.19 mmol, 516 mg) were dissolved in 15 mL of a mixture of 1,4-dioxane and water (v/v: 9/1) under nitrogen, and potassium carbonate (1.60 mmol, 221 mg) and Pd(dpp)$Cl_2$ (0.08 mmol, 59 mg) were added. The mixture was heated to 95° C. and reacted for 10 hours. The reaction was stopped. The mixture was filtered, and 40 mL of water was added to the system. The mixture was extracted with ethyl acetate, dried over anhydrous sodium sulfate, and separated by flash column chromatography to give compound A15-1 (170 mg, yield: 41%). LC-MS: $[M+H]^+$: 525.

Intermediate A15-1 (0.32 mmol, 170 mg) was dissolved in 10 mL of anhydrous dichloromethane in an ice bath and N-bromosuccinimide NBS (0.35 mmol, 63 mg) was slowly added in batches. The mixture was stirred at room temperature for 2 hours. The reaction was stopped, and 20 mL of saturated aqueous ammonium chloride solution was added. The mixture was extracted with dichloromethane, and dried over anhydrous sodium sulfate to give compound A15-2 (200 mg, crude). LC-MS: $[M+H]^+$: 604.

The crude intermediate A15-2 (200 mg) from the previous step and the raw material a3-2 (0.64 mmol, 178 mg) were dissolved in 10 mL of a mixture of 1,4-dioxane and water (v/v: 9/1) under nitrogen, and potassium carbonate (0.64 mmol, 89 mg) and Pd(dppf)$Cl_2$ (0.03 mmol, 22 mg) were added. The mixture was heated to 100° C. by microwave and reacted for 2 hours. The reaction was stopped. The mixture was filtered, and 20 mL of water was added to the system. The mixture was extracted with ethyl acetate, dried over anhydrous sodium sulfate, and separated by TLC chromatography to give compound A15-3 (45 mg, total yield for two steps: 21%). LC-MS: $[M+H]^+$: 675.

Intermediate A15-3 (45 mg) was dissolved in 4 mL of dichloromethane, and 1.5 mL of trifluoroacetic acid was added. The mixture was reacted at room temperature for 2 h. The reaction was stopped, and the solvent was evaporated under reduced pressure. Saturated aqueous sodium bicarbonate solution was added to adjust the pH to 10. The mixture was extracted with dichloromethane, and separated by preparative chromatography to give the target compound A15 (9 mg, yield: 30%), LC-MS: $[M+H]^+$: 491.

(Free base); $^1$H NMR (400 MHz, DMSO-$d_6$) δ 8.26 (s, 2H), 7.71 (s, 1H), 7.51 (s, 1H), 6.78 (s, 1H), 6.69 (s, 1H), 4.57 (s, 1H), 4.27 (s, 1H), 4.00 (dd, J=11.5, 3.6 Hz, 1H), 3.77 (d, J=11.4 Hz, 1H), 3.67 (dd, J=11.3, 3.1 Hz, 1H), 3.56-3.37 (m, 5H), 3.23 (dd, J=12.7, 3.9 Hz, 1H), 2.76 (m, 4H), 2.32 (s, 3H), 2.17 (s, 3H), 1.27 (d, J=6.7 Hz, 3H).

Example 9

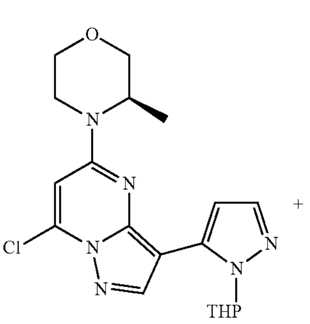

a4

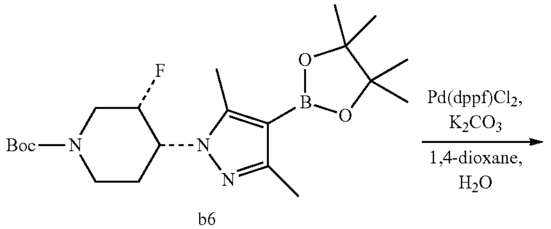

b6

-continued

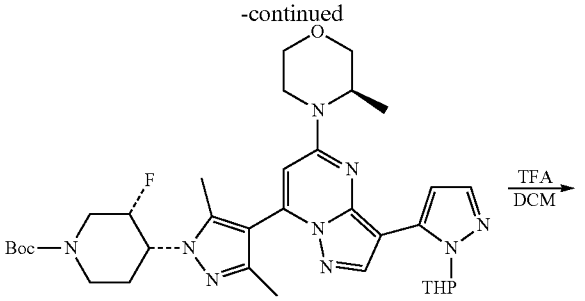

A16-1

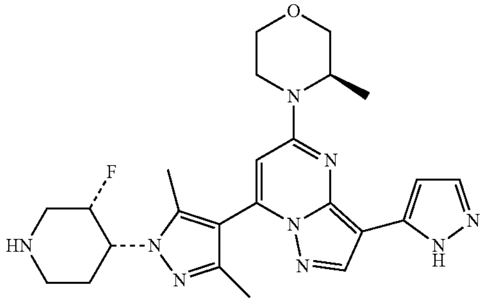

A16-I

Intermediate a4 (0.25 mmol, 100 mg) and intermediate b6 (0.50 mmol, 211 mg) were dissolved in 10 mL of a mixture of 1,4-dioxane and water (v/v: 9/1) under nitrogen, and potassium carbonate (0.50 mmol, 69 mg) and Pd(dppf)$Cl_2$ (0.03 mmol, 22 mg) were added. The mixture was heated to 100° C. by microwave and reacted for 2 hours. The reaction was stopped. The mixture was filtered, and 20 mL of water was added to the system. The mixture was extracted with ethyl acetate, dried over anhydrous sodium sulfate, and separated by TLC chromatography to give compound A16-1 (60 mg, yield: 36%). LC-MS: $[M+H]^+$: 664.

Intermediate A16-1 (60 mg) was dissolved in 4 mL of dichloromethane, and 2 mL of trifluoroacetic acid was added. The mixture was reacted at room temperature for 2 h. The reaction was stopped, and the solvent was evaporated under reduced pressure. Saturated aqueous sodium bicarbonate solution was added to adjust the pH to 10. The mixture was extracted with dichloromethane, and separated by preparative chromatography to give the target compound A16-1 (10 mg, yield: 23%), LC-MS: $[M+H]^+$: 480.

(Free base);

Referring to the synthetic route of compound A16-1, intermediate b6 was replaced with its diastereoisomer b7 to give the target compound A16-II.

(Free base); $^1$H NMR (400 MHz, DMSO-$d_6$) δ 8.24 (s, 1H), 7.59 (s, 1H), 6.74 (s, 1H), 6.64 (s, 1H), 4.92-4.73 (m, 1H), 4.56 (s, 1H), 4.43 (m, 1H), 4.27 (d, J=13.6 Hz, 1H), 4.02-3.96 (m, 1H), 3.76 (d, J=11.4 Hz, 1H), 3.66 (dd, J=11.4, 3.1 Hz, 1H), 3.55-3.49 (m, 1H), 3.44 (dd, J=7.0, 5.0 Hz, 1H), 3.25-3.18 (m, 1H), 2.97 (d, J=12.5 Hz, 1H), 2.68-2.61 (m, 2H), 2.25 (s, 3H), 2.16 (s, 3H), 2.08 (m, 1H), 1.92 (m, 1H), 1.27 (d, J=6.7 Hz, 3H).

The following compounds were synthesized with reference to Example 9

| Structure | Structure of intermediate replacing b6 | LC-MS/ $[M + H]^+$ | $^1$H NMR |
|---|---|---|---|
| 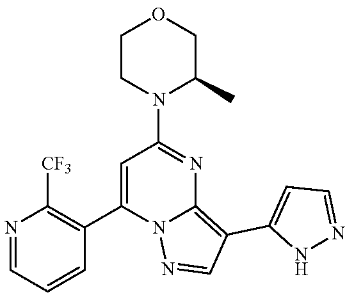 A21 | 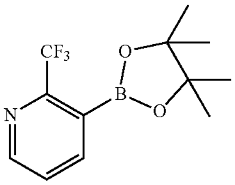 [SMILES: CC1(C)OB(c2cccnc2C(F)(F)F)OC1(C)C] | 430 | (Free base); $^1$H NMR (400 MHz, DMSO-$d_6$) δ 12.69 (br, 1H), 8.98 (dd, J = 4.7, 1.6 Hz, 1H), 8.27 (d, J = 7.8 Hz, 1H), 8.20 (s, 1H), 7.96 (dd, J = 7.9, 4.8 Hz, 1H), 7.61 (s, 1H), 6.96 (s, 1H), 6.75 (s, 1H), 4.53 (s, 1H), 4.25 (d, J = 13.5 Hz, 1H), 4.00 (dd, J = 11.4, 3.6 Hz, 1H), 3.77 (d, J = 11.5 Hz, 1H), 3.67 (dd, J = 11.5, 3.1 Hz, 1H), 3.52 (td, J = 11.8, 2.9 Hz, 1H), 3.25 (dd, J = 12.7, 3.9 Hz, 1H), 1.27 (d, J = 6.7 Hz, 3H). |

Example 10

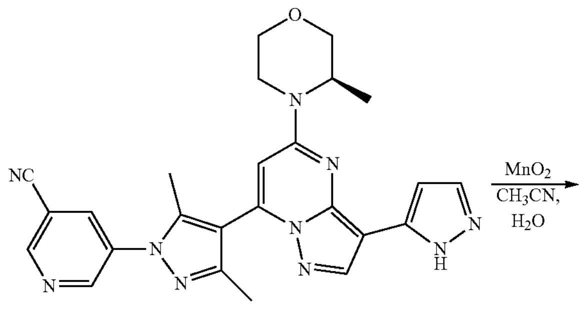

A11

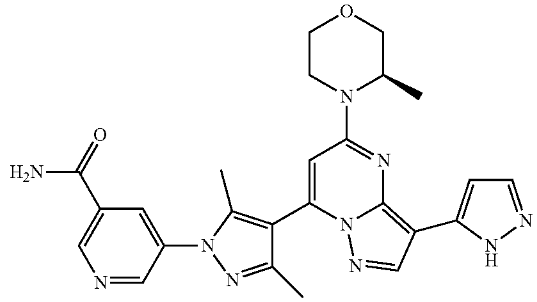

A17

Compound A11 (0.063 mmol, 30 mg) was dissolved in 6 mL of a mixture of water and acetonitrile (v/v, 5/1), and manganese dioxide (0.115 mmol, 10 mg) was added. The mixture was heated to 90° C. and reacted for 10 h. The reaction was stopped. The mixture was filtered, and separated by flash column chromatography to give compound A17 (4 mg, yield: 13%). LC-MS: $[M+H]^+$: 499.

(Free base); $^1H$ NMR (400 MHz, DMSO-$d_6$) δ 9.11 (d, J=1.9 Hz, 1H), 8.98 (d, J=2.4 Hz, 1H), 8.42 (t, J=2.2 Hz, 1H), 8.35 (s, 1H), 8.28 (s, 1H), 7.78 (s, 1H), 7.60 (s, 1H), 6.77 (s, 2H), 4.56 (d, J=7.4 Hz, 1H), 4.28 (d, J=13.4 Hz, 1H), 4.05-3.97 (m, 1H), 3.79 (d, J=11.5 Hz, 1H), 3.69 (m, 1H), 3.54 (m, 1H), 3.28-3.22 (m, 1H), 2.38 (s, 3H), 2.26 (s, 3H), 1.29 (d, J=6.7 Hz, 3H).

Example 11

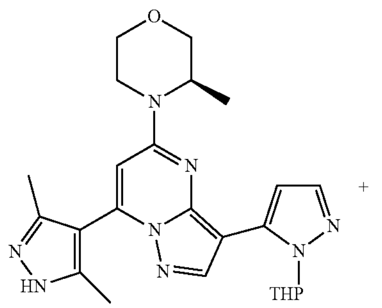

a3

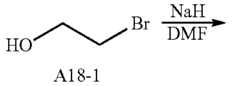

A18-1

-continued

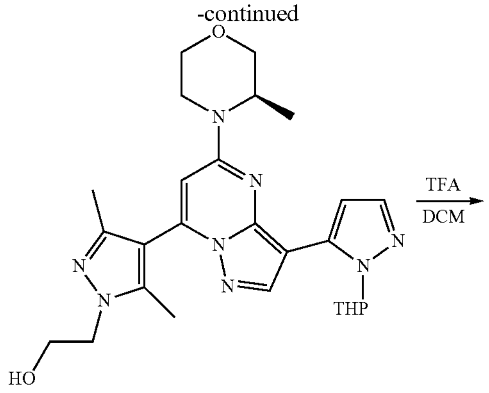

A18-2

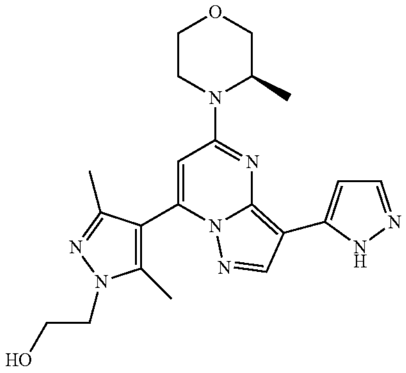

A18

Intermediate a3 (0.17 mmol, 80 mg) and 2-bromoethanol A18-1 (0.34 mmol, 43 mg), were added to a reaction flask under nitrogen, and dissolved with 5 mL of DMF. The mixture was stirred for 5 min, and then NaH (0.34 mmol, 14 mg) was slowly added. The mixture was heated to 50° C. and reacted for 2 h. The reaction was stopped. 40 mL of water was added. The mixture was extracted with ethyl acetate, dried over anhydrous $Na_2SO_4$, and separated by TLC chromatography to give compound A18-2 (40 mg, yield: 47%), LC-MS: $[M+H]^+$: 507.

Intermediate A18-2 (60 mg) was dissolved in 5 mL of dichloromethane, and 2 mL of trifluoroacetic acid was added. The mixture was reacted at room temperature for 2 hours. The reaction was stopped, and the solvent was evaporated under reduced pressure. Saturated aqueous sodium bicarbonate solution was added to adjust the pH to about 10. The mixture was extracted with dichloromethane, and separated by preparative chromatography to give the target compound A18 (20 mg, yield: 40%), LC-MS: $[M+H]^+$: 423.

(Free base); $^1H$ NMR (400 MHz, DMSO-$d_6$) δ 12.66 (br, 1H), 8.23 (s, 1H), 7.58 (s, 1H), 6.74 (s, 1H), 6.58 (s, 1H), 4.92 (t, J=5.3 Hz, 1H), 4.54 (d, J=7.5 Hz, 1H), 4.25 (d, J=13.6 Hz, 1H), 4.10 (t, J=5.7 Hz, 2H), 3.99 (dd, J=11.5, 3.6 Hz, 1H), 3.77 (m, 3H), 3.67 (dd, J=11.5, 3.1 Hz, 1H), 3.52 (td, J=11.8, 3.0 Hz, 1H), 3.28-3.20 (m, 1H), 2.25 (s, 3H), 2.13 (s, 3H), 1.27 (d, J=6.7 Hz, 3H).

Example 12

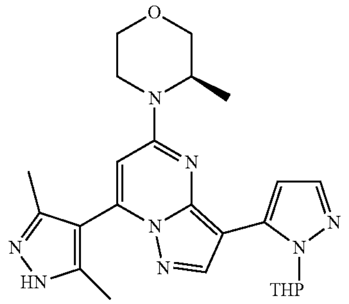

a3

+

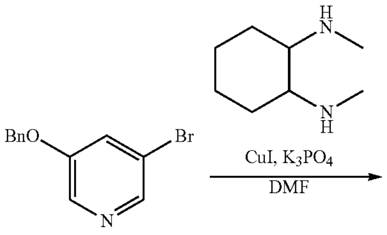

A19-1

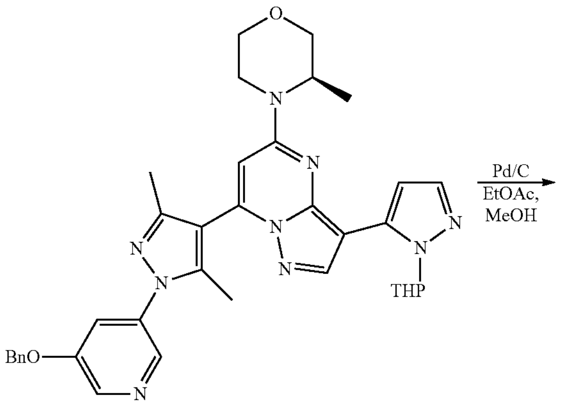

A19-2

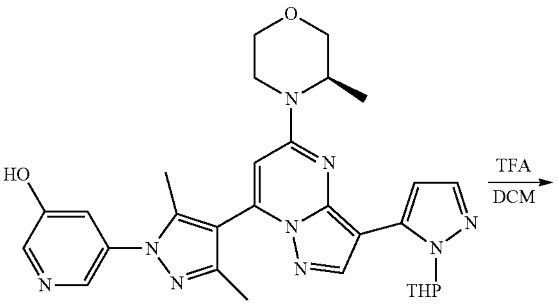

A19-3

-continued

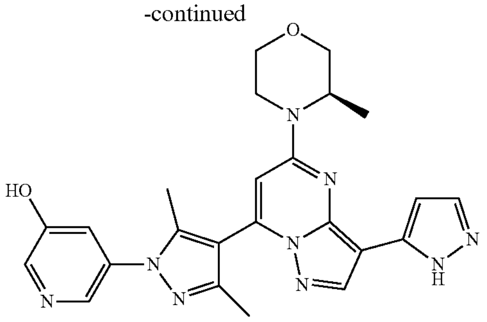

A19

Intermediate a3 (0.19 mmol, 90 mg), 3-bromo-5-benzyloxy-pyridine A19-1 (0.38 mmol, 100 mg), potassium phosphate (0.57 mmol, 120 mg) and CuI (0.04 mmol, 8 mg) were added to a microwave reaction flask under nitrogen, and dissolved with 5 mL of DMF. The mixture was stirred for 5 min, and then N,N-dimethyl-1,2-cyclohexanediamine (0.04 mmol, 5 mg) was slowly added. The mixture was heated to 110° C. and reacted for 10 h. The reaction was then stopped, and the mixture was filtered. 30 mL of water was added. The mixture was extracted with ethyl acetate, dried over anhydrous sodium sulfate, and separated by TLC chromatography to give compound A19-2 (85 mg, yield: 70%), LC-MS: $[M+H]^+$: 646.

Intermediate A19-2 (0.13 mmol, 85 mg) and Pd/C (9 mg) were mixed in 4 mL of a mixture of methanol and ethyl acetate (v/v, 3/1), and the air was replaced with hydrogen (4 atm). The mixture was heated to 50° C. and reacted for 2 h. The reaction was stopped. The mixture was filtered, and the solvent was evaporated under reduced pressure to give the crude intermediate A19-3. LC-MS: $[M+H]^+$: 556.

The crude intermediate A19-3 was dissolved in 5 mL of dichloromethane, and 2 mL of trifluoroacetic acid was added. The mixture was reacted at room temperature for 2 h. The reaction was stopped. The solvent was evaporated under reduced pressure, and 10 mL of saturated aqueous $NaHCO_3$ solution was slowly added to the system. The mixture was extracted with dichloromethane, dried over anhydrous sodium sulfate, and separated by preparative chromatography to give the target compound A19 (38 mg, total yield for two steps: 63%), LC-MS: $[M+H]^+$: 472.

(Free base); $^1$H NMR (400 MHz, DMSO-$d_6$) δ 8.32-8.24 (m, 2H), 8.22 (d, J=2.5 Hz, 1H), 7.60 (s, 1H), 7.36 (t, J=2.3 Hz, 1H), 6.76 (s, 2H), 4.56 (d, J=8.0 Hz, 1H), 4.27 (d, J=13.5 Hz, 1H), 4.01 (dd, J=11.4, 3.6 Hz, 1H), 3.79 (d, J=11.4 Hz, 1H), 3.69 (dd, J=11.5, 3.1 Hz, 1H), 3.54 (m, 1H), 3.27 (m, 1H), 2.33 (s, 3H), 2.23 (s, 3H), 1.29 (d, J=6.7 Hz, 3H).

Example 13

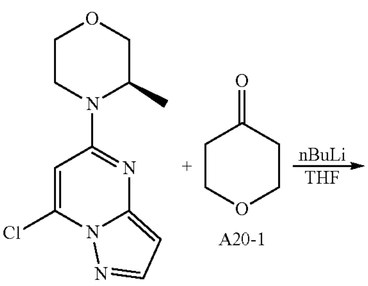

a1

A20-1

-continued

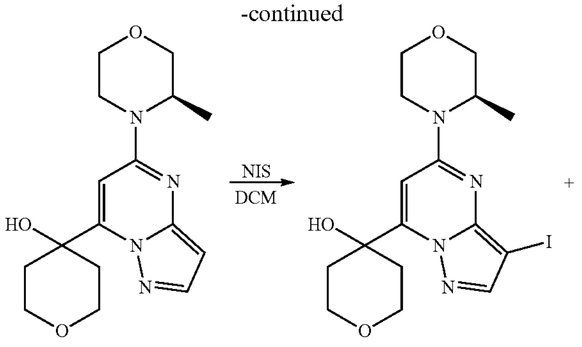

A20-2 A20-3

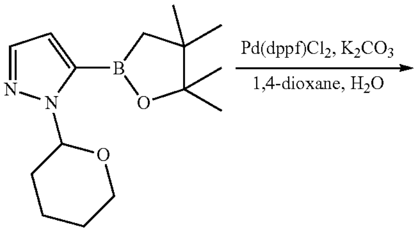

a3-2

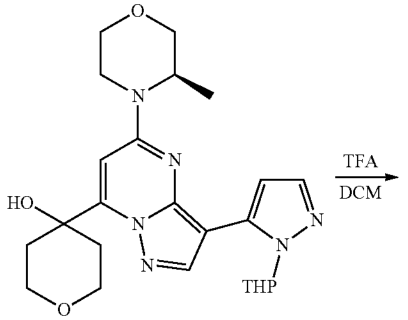

A20-4

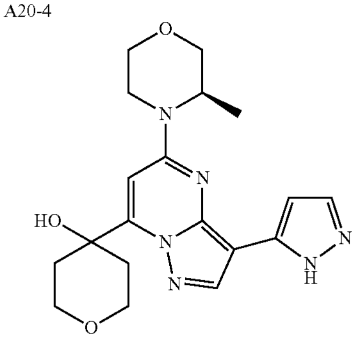

A20

Intermediate at (1.59 mmol, 400 mg) was dissolved in 15 mL of anhydrous tetrahydrofuran at −78° C. under nitrogen, and n-butyllithium (0.76 mL, 2.5 M) was added dropwise. The mixture was reacted for 30 min. Tetrahydropyran-4-one A20-1 (1.75 mmol, 175 mg) was then slowly added, and the mixture was stirred for another 2 h. The reaction was then stopped. 30 mL of saturated aqueous ammonium chloride solution was slowly added to the system. The mixture was extracted with dichloromethane, dried over anhydrous sodium sulfate, and separated by TLC chromatography to give compound A20-2 (100 mg, yield: 20%). LC-MS: $[M+H]^+$: 319.

Intermediate A20-2 (0.31 mmol, 100 mg) was dissolved in 10 mL of anhydrous dichloromethane in an ice bath and N-iodosuccinimide NIS (0.35 mmol, 79 mg) was slowly added in batches. The mixture was stirred at room temperature for 2 hours. The reaction was stopped, and 20 mL of saturated aqueous ammonium chloride solution was added. The mixture was extracted with dichloromethane, and dried over anhydrous sodium sulfate to give compound A20-3 (170 mg, crude). LC-MS: $[M+H]^+$: 445.

The crude intermediate A20-3 (170 mg) from the previous step and the raw material a3-2 (0.62 mmol, 172 mg) were dissolved in 10 mL of a mixture of 1,4-dioxane and water (v/v: 9/1) under nitrogen, and potassium carbonate (0.64 mmol, 89 mg) and $Pd(dppf)Cl_2$ (0.03 mmol, 22 mg) were added. The mixture was heated to 100° C. by microwave and reacted for 2 hours. The reaction was stopped. The mixture was filtered, and 20 mL of water was added to the system. The mixture was extracted with ethyl acetate, dried over anhydrous sodium sulfate, and separated by TLC chromatography to give compound A20-4 (120 mg, total yield for two steps: 83%). LC-MS: $[M+H]^+$: 467.

Intermediate A20-4 (120 mg) was dissolved in 6 mL of dichloromethane, and 3 mL of trifluoroacetic acid was added. The mixture was reacted at room temperature for 2 hours. The reaction was stopped, and the solvent was evaporated under reduced pressure. Saturated aqueous sodium bicarbonate solution was added to adjust the pH to 10. The mixture was extracted with dichloromethane, and separated by preparative chromatography to give the target compound A20 (61 mg, yield: 61%), LC-MS: $[M+H]^+$: 383. (Free base); $^1H$ NMR (400 MHz, DMSO-$d_6$) δ 12.68 (br, 1H), 8.33 (s, 1H), 7.70-7.52 (m, 1H), 6.81 (s, 1H), 6.73 (s, 1H), 5.87 (s, 1H), 4.58-4.45 (m, 1H), 4.18 (d, J=13.3 Hz, 1H), 4.01 (dd, J=11.4, 3.6 Hz, 1H), 3.81 (t, J=9.7 Hz, 5H), 3.66 (dd, J=11.5, 3.1 Hz, 1H), 3.51 (td, J=11.8, 2.9 Hz, 1H), 3.25 (dd, J=12.8, 3.8 Hz, 1H), 3.01 (td, J=12.7, 5.8 Hz, 2H), 1.50 (d, J=11.8 Hz, 2H), 1.28 (d, J=6.6 Hz, 3H).

Example 14: Assay of ATR Kinase Activity

Biotinylated protein derived from p53 (Eurofins, art. No.: 14-952) was phosphorylated with ATR kinase. The amount of phosphorylated protein was determined by time-resolved fluorescence in this assay. The amount of phosphorylated protein was detected by anti-p53-phospho-(serine 15)-K-specific antibody (Cisbio, art. No.: 61GSTDLA) and d2 labeled anti-GST antibody (Cisbio, art. No. 61P08KAE). Before the assay, the following working solutions were formulated as required: 1×reaction buffer (20 mM HEPES PH8.0, 1% glycerol, 0.01% Brij-35), dilution buffer (20 mM HEPES PH8.0, 1% glycerol, 0.01% Brij-35, 5 mM DTT and 1% BSA), stop solution (20 mM HEPES PH8.0, 1% glycerol, 0.01% Brij-35, 250 mM EDTA), detection buffer (50 mM HEPES pH7.0, 150 mM NaCl, 267 mM KF, 0.1% sodium cholate, 0.01% Tween-20, 0.0125% sodium azide). The reagents used above were purchased from Sigma or Invitrogen, except for those whose manufacturers were mentioned.

Operations were as Follows

4× serially diluted compound solutions were prepared with 1×reaction buffer to give 9 compound solutions with different concentrations, and 2.5 μL of the 4×serially diluted compound solutions were added to a 384-well analysis plate (784075, Greiner). 4×p53 substrate working solution (40 nM) was prepared with 1×reaction buffer, and 2.5 μL of the 4×p53 substrate working solution was added to a 384-well analysis plate. 4×ATR/ATRIP working solution (12.8 ng/μL) was prepared with dilution buffer, and 2.5 μL of the 4×pATR/ATRIP working solution was added to a 384-well analysis plate. 4×ATP working solution (2 mM) was prepared with deionized water, and 2.5 μL of the 4×ATP working solution was added to a 384-well analysis plate. The plates were incubated at room temperature in dark for 30 minutes. 5 μL of stop solution was added to the 384 analysis plates. Finally, 5 μL of assay mixture (0.084 ng/μL Anti-phospho-p53 (ser15)-K and 5 ng/μL Anti-GST-d2) was added to the 384 well analysis plates, and incubated at room temperature overnight. The fluorescence signal was detected with ENVISION (Perkinelmer) instrument (excitation wavelength: 320 nm, emission wavelength: 665 nm and 615 nm). The inhibition rate in each well was calculated by the fluorescence intensity value in each well: ER (Emission Ratio)=(Fluorescence intensity at 665 nm/Fluorescence intensity at 615 nm); inhibition rate=(ER of positive−ER of assay compound)/(ER of positive−ER of negative)×100%. $IC_{50}$ values of compounds were calculated by standard software for parameter fitting (GraphPad Prism 6.0).

Results of kinase data of example compounds:

| No. | ATR/IC50/nM |
|---|---|
| A1 | 70 |
| A2 | 33 |
| A3 | 184 |
| A4 | 74 |
| A6 | 17 |
| A7 | 12 |
| A8 | 84 |
| A9 | 2 |
| A10 | 3 |
| A11 | 9 |
| A12 | 2 |
| A13 | 2 |
| A14 | 3 |
| A15 | 13 |
| A16-I | 33 |
| A16-II | 31 |
| A17 | 3 |
| A18 | 8 |
| A19 | 4 |
| A20 | 188 |
| A21 | 52 |
| A22 | 2 |
| A23 | 4 |
| A24 | 2 |

Example 15: Assay of Cell Proliferation Inhibition In Vitro

By detecting the effect of compounds on cell activity in vitro in tumor cell lines TOV21G (ovarian cancer) and MV4-11 (leukemia), the inhibitory effect of compounds on cell proliferation was studied in this assay.

TOV21G cells and MV4-11 cells were purchased from American Type Culture Collection (ATCC).

TOV21G cells were cultured in MCDB105/M199 medium (containing 15% of FBS), and used for assaying when the cell confluence reached 85% or more. About 1000 cells were inoculated in each well of a 96-well culture plate, and cultured for 24 hours. Different concentrations (0-10 μM) of compounds to be assayed were added to treat the cells. Each group was assayed in triplicate. Blank wells (containing medium only) and control wells (inoculated cells without being treated with drug) were set. Cells were cultured for 120 hours. 40 μL of Cell Titer-Glo solutions (Promega, #G7573) were added to each well, and the cells were incubated with shaking for 20 min in the dark. 100 μL of solution was transferred from each well to a 96-well blank plate (Corning, #3917), and the luminescence value was read by Biotek Synergy H1 multifunctional microplate reader.

MV-4-11 cells were cultured in IMDM medium (containing 20% of FBS). About 10,000 cells were inoculated in each well of a 96-well culture plate, and treated by adding different concentrations (0-10 μM) of compounds to be assayed. Each group was assayed in triplicate. Blank wells (containing medium only) and control wells (inoculated cells without being treated with drug) were set. Cells were cultured for 120 hours. 40 μL of Cell Titer-Glo solutions were added to each well, and the cells were incubated with shaking for 20 min in the dark. 100 μL of solution was transferred from each well to a 96-well blank plate, and the luminescence value was read by Biotek Synergy H1 multifunctional microplate reader.

Inhibition rate (%)=100%×(control well−assay well)/(control well−blank well)

The results of the proliferation assay show that the assay compounds are effective in the studied human tumor cells, which is reflected by the $IC_{50}$ value ($IC_{50}$ is an inhibitory concentration at 50% of the maximum effect).

Results of cell activity assay by CellTiter-Glo luminescence method:

| No. | TOV21G/$IC_{50}$/μM | MV4-11/$IC_{50}$/μM |
|---|---|---|
| A1 | 0.66 | 0.66 |
| A2 | 0.83 | 0.78 |
| A3 | NT | NT |
| A4 | 1.05 | 0.75 |
| A5 | NT | NT |
| A8 | 0.78 | 0.68 |
| A9 | 0.28 | 0.25 |
| A10 | 0.30 | 0.27 |
| A11 | 0.38 | 0.50 |
| A12 | 0.33 | 0.26 |
| A13 | 0.21 | 0.28 |
| A15 | 0.27 | 0.45 |
| A16-I | 1.40 | 0.89 |
| A16-II | 0.52 | 0.57 |
| A17 | 1.29 | 0.85 |
| A18 | 0.56 | 0.74 |
| A19 | 0.66 | 0.60 |
| A20 | 0.73 | 0.92 |
| A21 | 0.63 | 0.74 |
| A22 | 0.19 | 0.23 |
| A23 | 0.26 | 0.30 |
| A24 | 0.15 | 0.23 |

NT = Not tested

Example 16: In Vitro Stability Assay of Compounds in Liver Microsome

The compounds of the present disclosure were subjected to stability assay in liver microsome. The compound to be assayed (with a final concentration of 2.0 nM) was co-incubated with human/mouse liver microsomes with or without the addition of NADPH. The concentration of the compound in the supernatant was determined within 60 minutes of incubation. The results for representative compounds were as follows:

| Compound | Human liver microsome $t_{1/2}$ (min) | Mouse liver microsome $t_{1/2}$ (min) |
|---|---|---|
| A9 | 86 | 218 |
| A10 | 36 | 162 |

Example 17: Assay of In Vivo Pharmacokinetics of Compounds

In vivo pharmacokinetic studies were performed on the compounds of the present disclosure.

Assay Method:

Male ICR mice (3 mice/group) were administered orally by gavage at a dose of 10 mg/kg. The plasma samples were collected before administration (0 h) and after administration (0.25, 0.5, 1, 2, 4, 6, 8, 24 h). The collected samples were subjected to LC/MS/analysis, and the data were collected. The relevant pharmacokinetic parameters were calculated by Analyst v1.6.2 (AB Applied Biosystems Company, USA) software using the collected analytical data.

The results for representative compounds were as follows:

| Compound | $t_{1/2}$ (h) | $T_{max}$ (h) | $C_{max}$ (ng/mL) | AUC (h*ng/mL) |
|---|---|---|---|---|
| A9 | 3.3 | 0.25 | 1809 | 6951 |
| A10 | 1.76 | 0.25 | 4891 | 14275 |
| A12 | 1.98 | 0.33 | 2268 | 8333 |

Example 18: Study on the Selectivity of Compounds for ATR Kinase

The compounds of the present disclosure were assayed for inhibition of the same family (ATM, DNA-PK, PI3K, mTOR):

According to the assay method reported in the literature, the compound to be assayed was serially diluted 3-fold to 0.51 nM starting from 10 μM (a total of 10 concentrations), and assayed for the inhibitory activities against kinases ATM[1], DNA-PK[2], PI3Kα[3], PI3Kδ[3] and mTOR[4], respectively. The results were shown below:

| Compound | $IC_{50}$/ATM (nM) | $IC_{50}$/DNAPK (nM) | $IC_{50}$/PI3Kα (nM) | $IC_{50}$/PI3Kδ (nM) | $IC_{50}$/mTOR (nM) |
|---|---|---|---|---|---|
| A9 | 6372 | 303 | 4064 | 1131 | 1833 |
| A10 | 4119 | 1259 | NT | NT | NT |

The above results indicate that the compounds of the present disclosure are highly selective for ATR and have lower inhibitory activity to other kinases in the family.

REFERENCES

[1] Discovery of Novel 3-Quinoline Carboxamides as Potent, Selective and Orally Bioavailable Inhibitors of Ataxia Telangiectasia Mutated (ATM) Kinase, *J Med. Chem.* 2016, 56, 6281-6292;

[2] The Discovery of 7-Methyl-2-[(7-methyl[1,2,4]triazolo[1,5-a]pyridin-6-yl)amino]-9-(tetrahydro-2H-pyran-4-yl)-7,9-dihydro-8H-purin-8-one (AZD7648), a Potent and Selective DNA-Dependent Protein Kinase (DNA-PK) Inhibitor, *J. Med. Chem.* 2020, 63, 3461-3471;

[3] WO2012044641;

[4] Discovery and SAR exploration of a novel series of imidazo[4,5-b]pyrazin-2-ones as potent and selective mTOR kinase inhibitors. *Bioorg. Med. Chem. Lett.* 2011; 21: 6793-6799.

The above is a further detailed description of the present disclosure in connection with the specific alternative embodiments, and the specific embodiments of the present disclosure are not limited to the description. Those of ordinary skill in the technical field of the present invention can also make some simple deductions or replacements without departing from the spirit of the present invention, all of which should be regarded as falling within the scope of protection of the present invention.

What is claimed is:

1. A compound of general formula (I), or a pharmaceutically acceptable salt, enantiomer, diastereomer, racemate, solvate, hydrate, polymorph, prodrug, or isotopic variant thereof, or a mixture thereof:

(I)

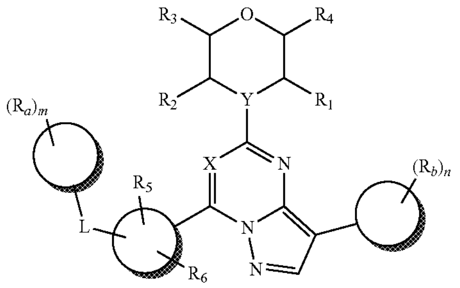

wherein

X is $CR_X$ or N;

Y is $CR_Y$ or N;

$R_1$, $R_2$, $R_3$, $R_4$ and $R_Y$ are independently selected from H, D, halogen, $C_{1-6}$ alkyl, $C_{2-6}$ alkenyl and $C_{2-6}$ alkynyl, or $R_1$ and $R_2$, $R_3$ and $R_4$ are connected to form bond, $C_{1-6}$ alkylene, $C_{2-6}$ alkenylene or $C_{2-6}$ alkynylene; wherein the groups may be substituted by one or more D or halogens up to fully substituted;

wherein $R_X$ is H, D, halogen, —CN, —NRR', —OR, —SR or $C_{1-6}$ alkyl, wherein the groups may be substituted by one or more D or halogens up to fully substituted;

when Y is $CR_Y$, $R_Y$ and $R_1$ are taken together with the atoms to which they are attached to form $C_{3-5}$ cycloalkyl or 3- to 5-membered heterocyclyl, wherein the groups may be substituted by one or more D or halogens up to fully substituted;

ring A is $C_{3-7}$ cycloalkyl, 4- to 7-membered heterocyclyl, $C_{6-10}$ aryl or 5- to 10-membered heteroaryl;

$R_a$ is independently selected from H, D, halogen, —CN, —NRR', —OR, —SR, —C(O)R, —C(O)OR, —C(O)NRR', —OC(O)R', —NRC(O)R', —OC(O)NRR', —NRC(O)NRR', —$S(O)_pR$, $C_{1-6}$ alkyl, $C_{2-6}$ alkenyl, $C_{2-6}$ alkynyl, $C_{3-7}$ cycloalkyl and 3- to 8-membered heterocyclyl, each of which is optionally substituted with R*, wherein the groups may be substituted by one or more D or halogens up to fully substituted;

m is 0, 1, 2, 3, 4 or 5;

ring B is 5- to 6-membered heteroaryl;

$R_b$ is independently selected from H, D, halogen, —CN, —NRR', —OR, —SR, —C(O)R, —C(O)OR, —C(O)

NRR', —OC(O)R', —NRC(O)R', —OC(O)NRR', —NRC(O)NRR', —$S(O)_pR$, $C_{1-6}$ alkyl, $C_{2-6}$ alkenyl, $C_{2-6}$ alkynyl, $C_{3-7}$ cycloalkyl and 3- to 8-membered heterocyclyl, each of which is optionally substituted with R*, wherein the groups may be substituted by one or more D or halogens up to fully substituted;

n is 0, 1, 2, 3, 4 or 5;

ring C is $C_{3-7}$ cycloalkyl, 4- to 7-membered heterocyclyl, $C_{6-10}$ aryl or 5- to 10-membered heteroaryl;

L is a bond, —O—, —S—, —N(R)—, —C(O)—, $C_{1-6}$ alkylene, $C_{2-6}$ alkenylene or $C_{2-6}$ alkynylene;

$R_5$ is H, D, halogen, —CN, —NRR', —OR, —SR, $C_{1-6}$ alkyl, $C_{2-6}$ alkenyl or $C_{2-6}$ alkynyl, wherein the groups may be substituted by one or more D or halogens up to fully substituted;

$R_6$ is H, D, halogen, —CN, —NRR', —OR, —SR, $C_{1-6}$ alkyl, $C_{2-6}$ alkenyl or $C_{2-6}$ alkynyl, wherein the groups may be substituted by one or more D or halogens up to fully substituted;

R* is H, halogen, —CN, —NRR', —OR, —SR, —C(O)R, —C(O) OR, —C(O)NRR', —OC(O)R', —NRC(O)R', —OC(O)NRR', —NRC(O)NRR', —$S(O)_pR$, $C_{3-7}$ cycloalkyl, 3- to 8-membered heterocyclyl, $C_{6-10}$ aryl or 5- to 10-membered heteroaryl, wherein the groups may be substituted by one or more D or halogens up to fully substituted;

R and R' are independently selected from H, $C_{1-6}$ alkyl, $C_{2-6}$ alkenyl and $C_{2-6}$ alkynyl, or R and R' are taken together with the nitrogen atom to which they are attached to form 4- to 8-membered heterocyclyl; wherein the groups may be substituted by one or more D or halogens up to fully substituted;

p is 1 or 2.

2. The compound of claim 1, or a pharmaceutically acceptable salt, enantiomer, diastereomer, racemate, solvate, hydrate, polymorph, or isotopic variant thereof, or a mixture thereof, wherein the compound has one or more of the following definitions:

i) wherein $R_1$ is $C_{1-6}$ alkyl, alternatively (R)—$C_{1-6}$ alkyl, yet alternatively (R)-methyl;

ii) wherein X is $CR_X$, and $R_2$, $R_3$, $R_4$ and $R_X$ are hydrogen or D;

iii) wherein Y is N;

iv) wherein ring A is selected from the following groups:

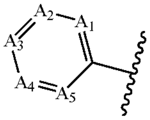
,
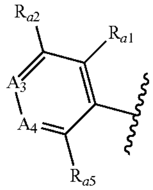
,
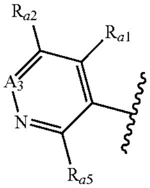
and
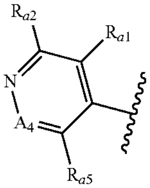
, wherein $A_1$ is $CR_{a1}$ or N; $A_2$ is $CR_{a2}$ or N; $A_3$ is $CR_{a3}$ or N; $A_4$ is $CR_{a4}$ or N; $A_5$ is $CR_{a5}$ or N;

$R_{a1}$, $R_{a2}$, $R_{a3}$, $R_{a4}$ and Ras have the same definition as $R_a$ in claim 1;

alternatively, $(R_a)_m$-ring A-L- is selected from the following groups:

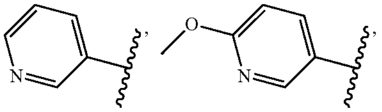
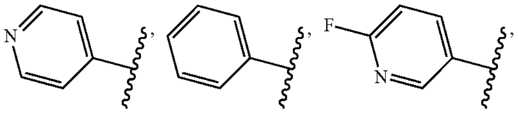
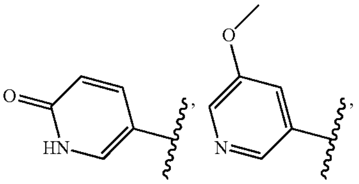
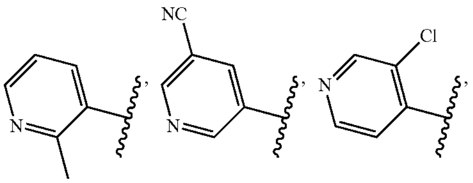
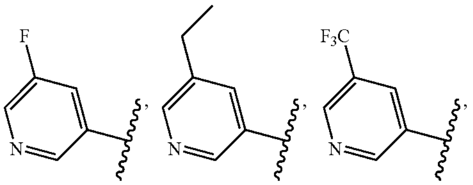
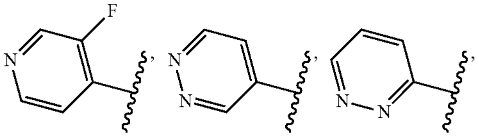
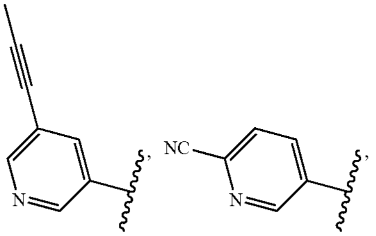
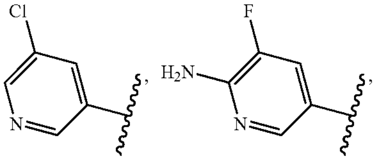
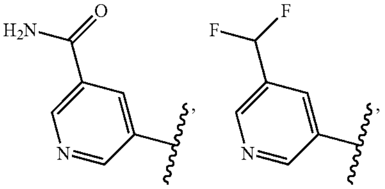

-continued

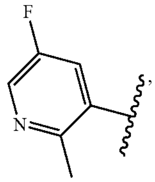

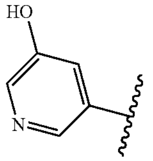

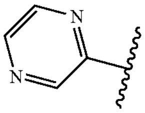

and

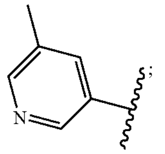

v) wherein ring A is selected from piperazinyl and piperidinyl;

vi) wherein $R_a$ is independently selected from H, D, halogen, —CN, —NRR', —OR, —SR, —C(O)R, —C(O)OR, —C(O)NRR', $C_{1-6}$ alkyl, $C_{1-6}$ haloalkyl, $C_{2-6}$ alkenyl and $C_{2-6}$ alkynyl, wherein the groups may be substituted by one or more D up to fully deuterated;

vii) wherein ring B is pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrrolyl, furanyl, thienyl, pyrazolyl or pyridyl; alternatively pyrazolyl;

viii) wherein $R_b$ is independently selected from H, D, halogen, —CN, —NRR', —OR, —SR, $C_{1-6}$ alkyl and $C_{1-6}$ haloalkyl, each of which is optionally substituted with R*; alternatively H or D;

ix) wherein ring C is 5- to 6-membered heteroaryl or phenyl; alternatively pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrazolyl, oxazolyl, isoxazolyl, thiazolyl, isothiazolyl or triazolyl; alternatively pyrazolyl;

x) wherein ring C is $C_{3-7}$ cycloalkyl or 4- to 7-membered heterocyclyl;

xi) wherein L is a bond, —C(O)— or $C_{1-6}$ alkylene;

xii) wherein $R_5$ and $R_6$ are independently H, D, $C_{1-6}$ alkyl, $C_{2-6}$ alkenyl or $C_{2-6}$ alkynyl, wherein the groups may be substituted by one or more D or halogens up to fully substituted.

3. The compound of claim 1, or a pharmaceutically acceptable salt, enantiomer, diastereomer, racemate, solvate, hydrate, polymorph, or isotopic variant thereof, or a mixture thereof, which has the following general structure:

(I-1)

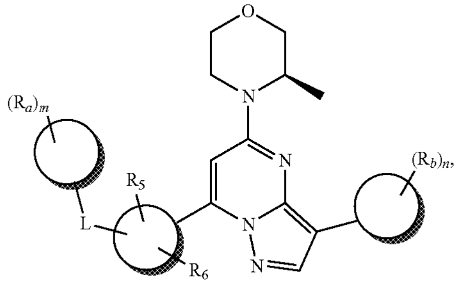

-continued (II)

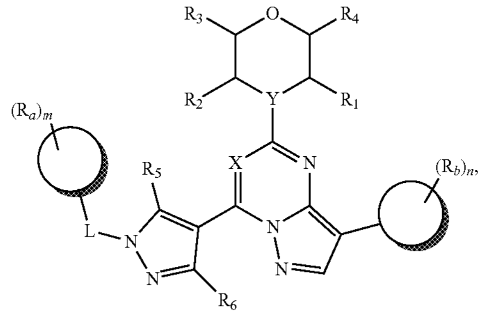

(II-1)

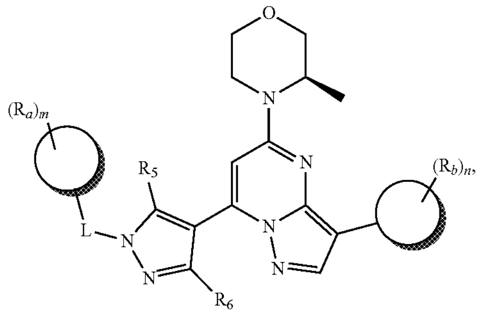

(III)

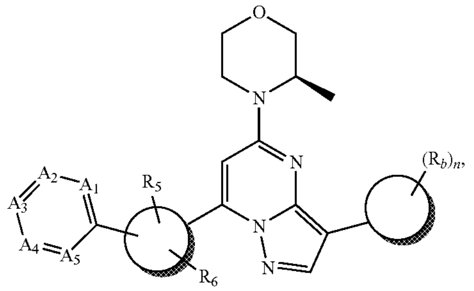

(III-1)

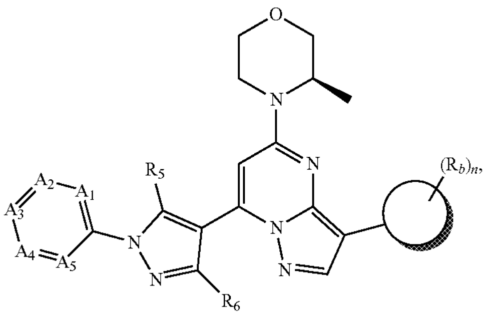

(III-2)

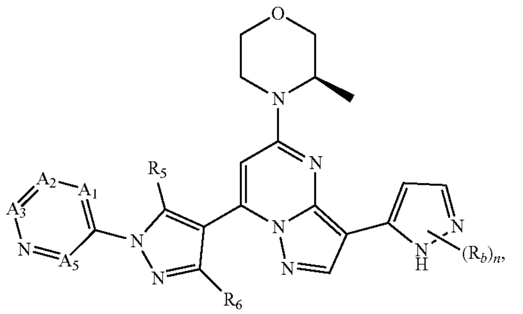

-continued (III-3)

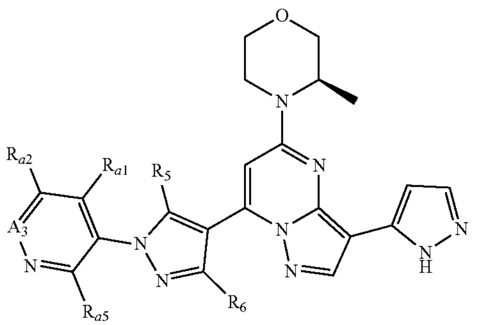

or (III-4)

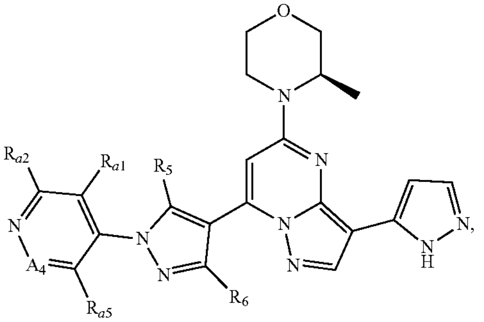

wherein each group has the same definition as in claim 1.

4. The compound of claim 3, or a pharmaceutically acceptable salt, enantiomer, diastereomer, racemate, solvate, hydrate, polymorph, or isotopic variant thereof, or a mixture thereof, which is a compound of general formula (I-1) or (I-2):

(I-1)

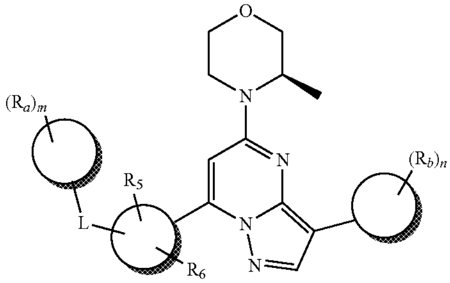

wherein ring C is $C_{3-7}$ cycloalkyl or 4- to 7-membered heterocyclyl; alternatively cyclopentyl or tetrahydropyranyl;

ring B is pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrrolyl, furanyl, thienyl, pyrazolyl or pyridyl;

$R_5$ is alternatively H, D, halogen, —CN, —NRR', —OR, or —SR, wherein the groups may be substituted by one or more D or halogens up to fully substituted; alternatively, $R_5$ is located on the C atom where the ring C is attached to the parent nucleus;

other groups have the same definition as in claim 3.

5. The compound of claim 3, or a pharmaceutically acceptable salt, enantiomer, diastereomer, racemate, solvate, hydrate, polymorph, or isotopic variant thereof, or a mixture thereof, which is a compound of general formula (I-1):

(I-1)

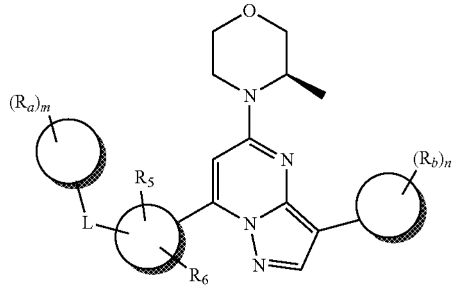

wherein ring C is 5- to 6-membered heteroaryl or phenyl; alternatively pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrazolyl, oxazolyl, isoxazolyl, thiazolyl, isothiazolyl or triazolyl; alternatively pyrazolyl;

other groups have the same definition as in claim 3.

6. The compound of general formula (I-1) of claim 5, or a pharmaceutically acceptable salt, enantiomer, diastereomer, racemate, solvate, hydrate, polymorph, or isotopic variant thereof, or a mixture thereof, wherein ring B is pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrrolyl, furanyl, thienyl, pyrazolyl or pyridyl;

other groups have the same definition as in claim 5.

7. The compound of claim 3, or a pharmaceutically acceptable salt, enantiomer, diastereomer, racemate, solvate, hydrate, polymorph, or isotopic variant thereof, or a mixture thereof, which is a compound of general formula (II) or (II-1):

(II)

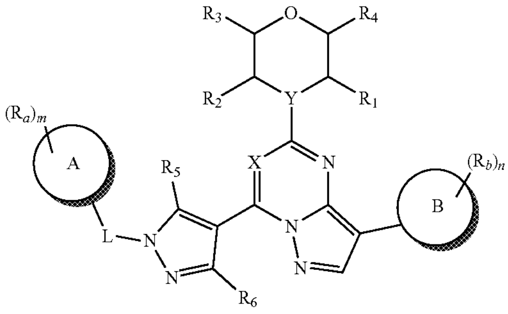

or (II-1)

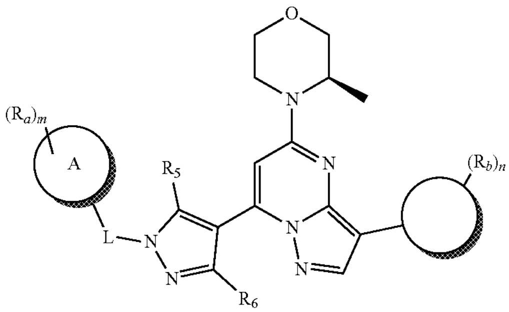

wherein ring A is $C_{3-7}$ cycloalkyl or 4- to 7-membered heterocyclyl;

other groups have the same definition as in claim 3;

alternatively, ring A is 4- to 7-membered heterocyclyl; alternatively piperidyl or piperazinyl;

ring B is pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrrolyl, furanyl, thienyl, pyrazolyl or pyridyl;

L is a bond, —O—, —S—, —N(R)—, —C(O)— or $C_{1-6}$ alkylene;

$R_5$ and $R_6$ are independently $C_{1-6}$ alkyl, $C_{1-6}$ haloalkyl, $C_{2-6}$ alkenyl or $C_{2-6}$ alkynyl, wherein the groups may be substituted by one or more D up to fully deuterated;

other groups have the same definition as in claim 3.

8. The compound of claim 3, or a pharmaceutically acceptable salt, enantiomer, diastereomer, racemate, solvate, hydrate, polymorph, or isotopic variant thereof, or a mixture thereof, which is a compound of general formula (III) or (III-1):

(III)

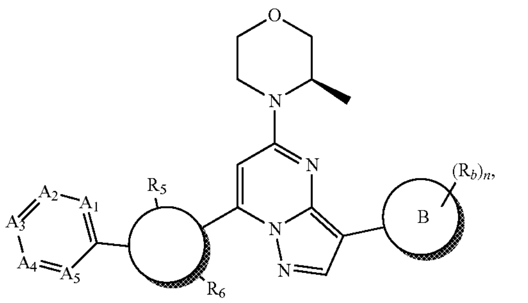

(III-1)

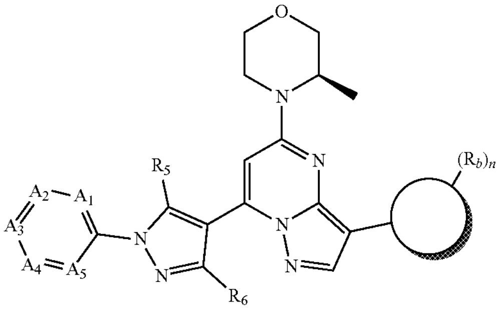

wherein ring C is 5- to 6-membered heteroaryl or phenyl; alternatively pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrazolyl, oxazolyl, isoxazolyl, thiazolyl, isothiazolyl or triazolyl; alternatively pyrazolyl;

other groups have the same definition as in claim 3.

9. The compound of general formula (III) or (III-1) of claim 8, or a pharmaceutically acceptable salt, enantiomer, diastereomer, racemate, solvate, hydrate, polymorph, or isotopic variant thereof, or a mixture thereof, wherein ring B is pyrrolyl, furanyl, thienyl, pyrazolyl, imidazolyl, oxazolyl, isoxazolyl, thiazolyl, isothiazolyl, triazolyl, pyridyl, pyrimidinyl or pyrazinyl; alternatively pyrrolyl, furanyl, thienyl, pyrazolyl or pyridyl;

other groups have the same definition as in claim 8.

10. The compound of claim 3, or a pharmaceutically acceptable salt, enantiomer, diastereomer, racemate, solvate, hydrate, polymorph, or isotopic variant thereof, or a mixture thereof, which is a compound of general formula (III-2) or (III-3):

(III-2)

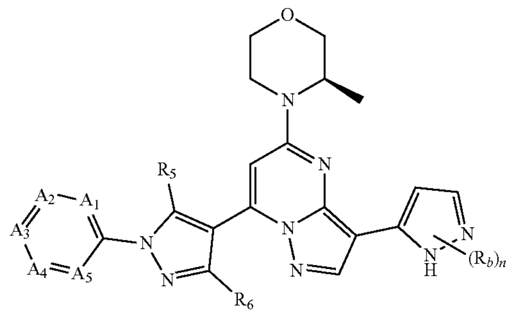

or (III-3)

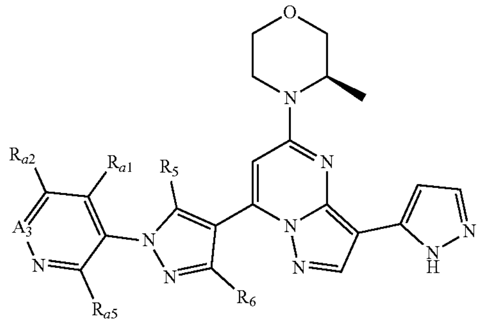

wherein $A_1$ is $CR_{a1}$ or N; $A_2$ is $CR_{a2}$ or N; $A_5$ is $CR_{a5}$ or N;

other groups have the same definition as in claim 3.

11. The compound of general formula (III-3) of claim 10, or a pharmaceutically acceptable salt, enantiomer, diastereomer, racemate, solvate, hydrate, polymorph, or isotopic variant thereof, or a mixture thereof, wherein $A_3$ is $CR_{a3}$ or N;

$R_{a1}$, $R_{a2}$, $R_{a3}$, $R_{a5}$, $R_5$ and $R_6$ are independently H, D, halogen, —CN, —OR, —SR, —NRR', —C(O)R, —C(O)OR, —C(O)NRR' or $C_{1-6}$ alkyl, wherein the groups may be substituted by one or more D or halogens up to fully substituted;

other groups have the same definition as in claim 10;

alternatively, $A_3$ is $CR_{a3}$ or N;

$R_{a1}$, $R_{a2}$, $R_{a3}$ and Ras are independently selected from H, D, halogen, —CN, —OH, —C(O)$NH_2$, $C_{1-6}$ alkyl and $C_{1-6}$ haloalkyl, wherein the groups may be substituted by one or more D up to fully deuterated;

$R_5$ and $R_6$ are independently $C_{1-6}$ alkyl or $C_{1-6}$ haloalkyl, wherein the groups may be substituted by one or more D up to fully deuterated;

alternatively, $A_3$ is $CR_{a3}$ or N;

$R_{a1}$ is H or D;

$R_{a2}$ is H, D, halogen, —CN, —OH, —C(O)$NH_2$, $C_{1-6}$ alkyl or $C_{1-6}$ haloalkyl;

$R_{a3}$ is H, D or —OH;

$R_{a5}$ is H or D;

$R_5$ is $C_{1-6}$ alkyl or $C_{1-6}$ haloalkyl; alternatively methyl;

$R_6$ is $C_{1-6}$ alkyl or $C_{1-6}$ haloalkyl; alternatively methyl.

12. The compound of claim 3, or a pharmaceutically acceptable salt, enantiomer, diastereomer, racemate, solvate, hydrate, polymorph, or isotopic variant thereof, or a mixture thereof, which is a compound of general formula (III-3):

(III-3)

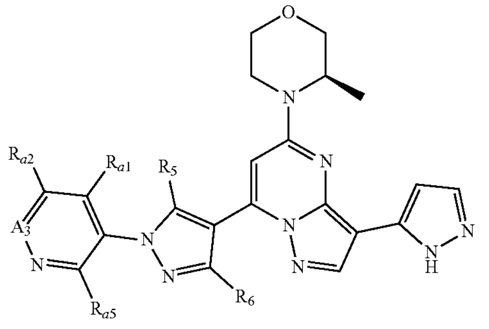

wherein $A_3$ is $CR_{a3}$ or N;

$R_{a1}$, $R_{a2}$, $R_{a3}$, $R_{a5}$, $R_5$ and $R_6$ are independently H, D, halogen, —OR, —SR, —NRR', $C_{1-6}$ alkyl or $C_{1-6}$ haloalkyl, wherein the groups may be substituted by one or more D up to fully deuterated;

R and R' are independently selected from H, $C_{1-6}$ alkyl, $C_{1-6}$ haloalkyl, $C_{2-6}$ alkenyl and $C_{2-6}$ alkynyl, or R and R' are taken together with the nitrogen atom to which they are attached to form 4- to 8-membered heterocyclyl; wherein the groups may be substituted by one or more D up to fully deuterated.

13. The compound of general formula (III-3) of claim 12, or a pharmaceutically acceptable salt, enantiomer, diastereomer, racemate, solvate, hydrate, polymorph, or isotopic variant thereof, or a mixture thereof, wherein $A_3$ is $CR_{a3}$ or N;

$R_{a1}$, $R_{a2}$, $R_{a3}$ and Ras are independently selected from H, D, halogen, —OH, $C_{1-6}$ alkyl and $C_{1-6}$ haloalkyl, wherein the groups may be substituted by one or more D up to fully deuterated;

$R_5$ and $R_6$ are independently $C_{1-6}$ alkyl or $C_{1-6}$ haloalkyl, wherein the groups may be substituted by one or more D up to fully deuterated;

alternatively, $A_3$ is $CR_{a3}$ or N;

$R_{a1}$ is H or D;

$R_{a2}$ is H, D, halogen, $C_{1-6}$ alkyl or $C_{1-6}$ haloalkyl;

$R_{a3}$ is H, D or —OH;

$R_{a5}$ is H or D;

$R_5$ is $C_{1-6}$ alkyl or $C_{1-6}$ haloalkyl; alternatively methyl;

$R_6$ is $C_{1-6}$ alkyl or $C_{1-6}$ haloalkyl; alternatively methyl.

14. The compound of claim 3, or a pharmaceutically acceptable salt, enantiomer, diastereomer, racemate, solvate, hydrate, polymorph, or isotopic variant thereof, or a mixture thereof, which is a compound of general formula (III-4):

(III-4)

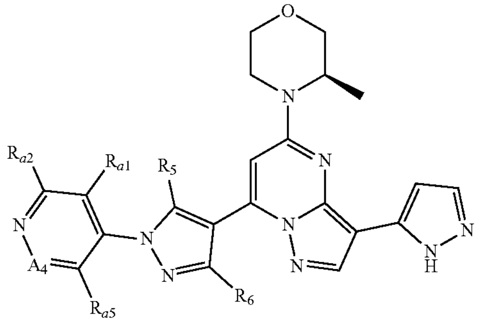

wherein $A_4$ is $CR_{a4}$ or N;

$R_{a1}$, $R_{a2}$, $R_{a4}$, $R_{a5}$, $R_5$ and $R_6$ are independently H, D, halogen, —CN, —OR, —SR, —NRR', —C(O)R, —C(O)OR, —C(O)NRR' or $C_{1-6}$ alkyl, wherein the groups may be substituted by one or more D or halogens up to fully substituted;

other groups have the same definition as in claim 3.

15. The compound of general formula (III-4) of claim 14, or a pharmaceutically acceptable salt, enantiomer, diastereomer, racemate, solvate, hydrate, polymorph, or isotopic variant thereof, or a mixture thereof, wherein $A_4$ is $CR_{a4}$ or N;

$R_{a1}$, $R_{a2}$, $R_{a4}$ and Ras are independently selected from H, D, halogen, —CN, —OH, —$C(O)NH_2$, $C_{1-6}$ alkyl and $C_{1-6}$ haloalkyl, wherein the groups may be substituted by one or more D up to fully deuterated;

$R_5$ and $R_6$ are independently $C_{1-6}$ alkyl or $C_{1-6}$ haloalkyl, wherein the groups may be substituted by one or more D up to fully deuterated;

alternatively, $A_4$ is $CR_{a4}$ or N;

$R_{a1}$ is H, D or halogen;

$R_{a2}$ is H, D, halogen, —CN, —OH, —$C(O)NH_2$, $C_{1-6}$ alkyl or $C_{1-6}$ haloalkyl;

$R_{a4}$ is H, D or —OH;

$R_{a5}$ is H or D;

$R_5$ is $C_{1-6}$ alkyl or $C_{1-6}$ haloalkyl; alternatively methyl;

$R_6$ is $C_{1-6}$ alkyl or $C_{1-6}$ haloalkyl; alternatively methyl.

16. The compound of claim 1, which is selected from:

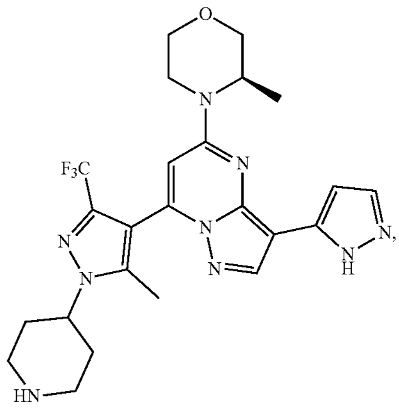
,

-continued
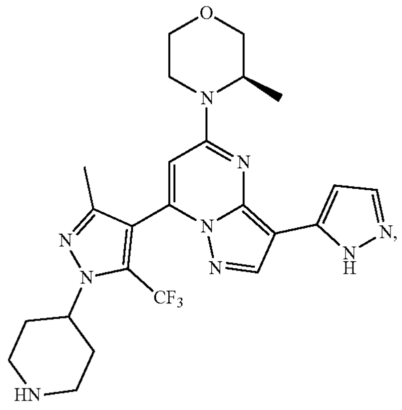
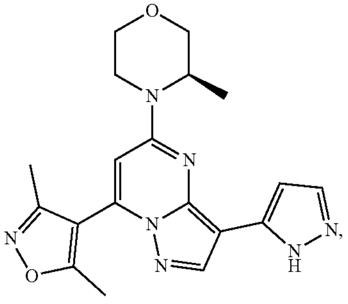
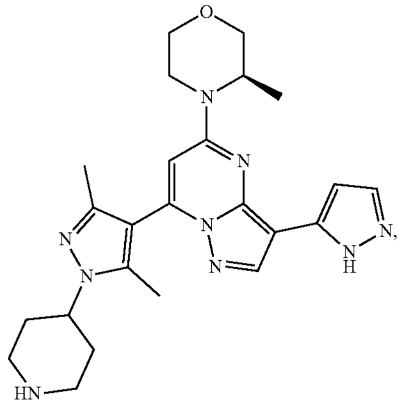
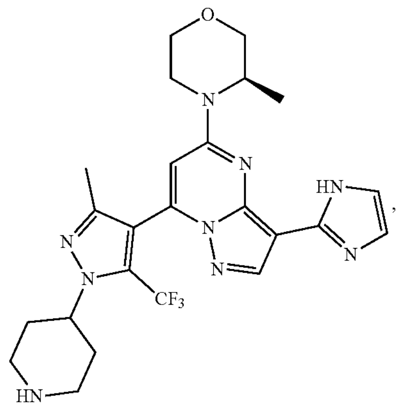
-continued
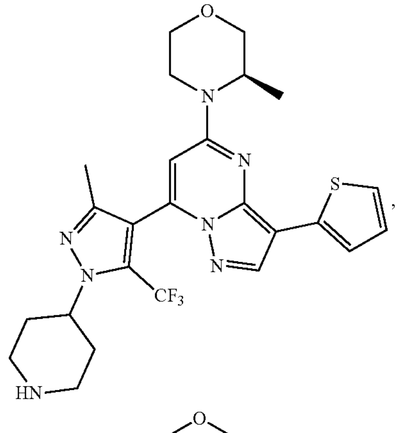
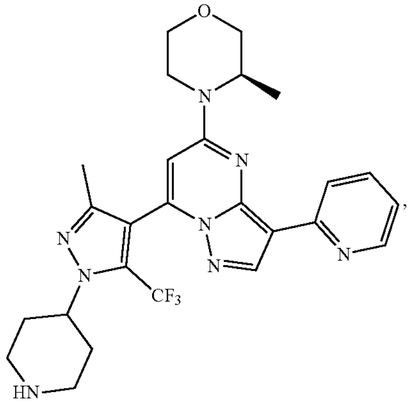
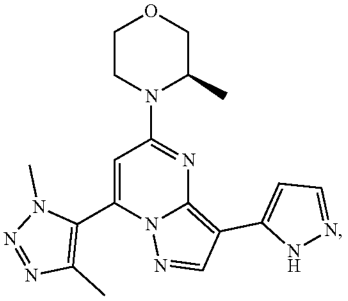
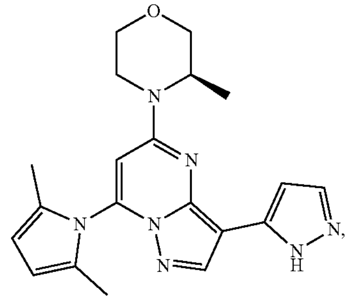
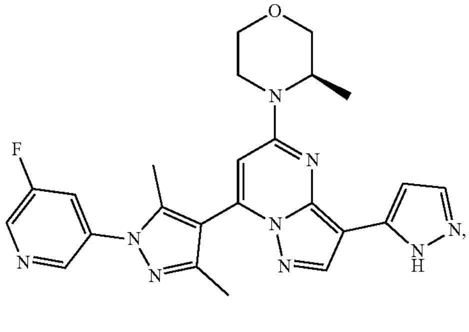

-continued
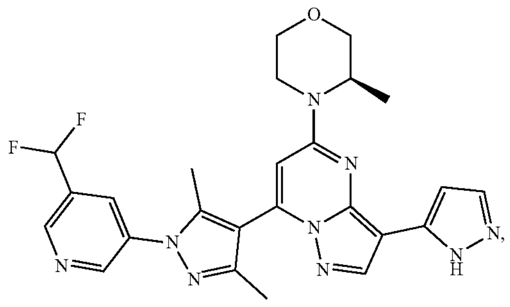
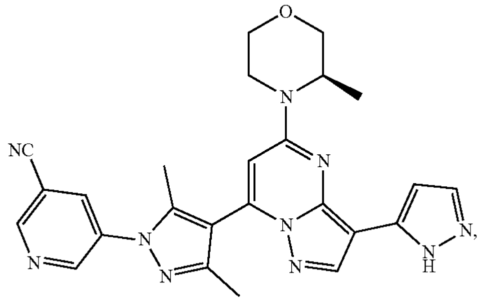
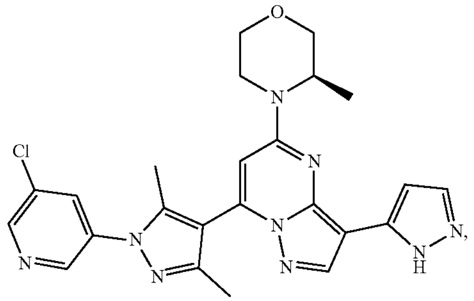
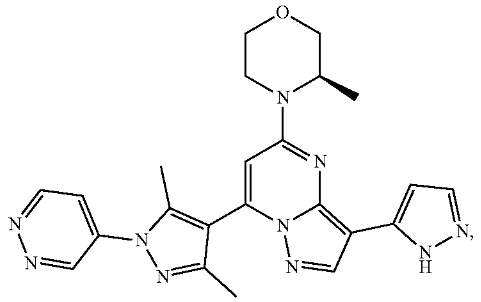
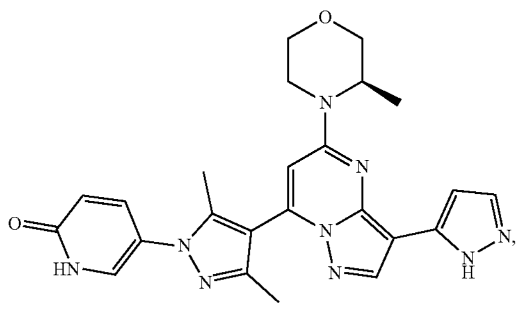
-continued
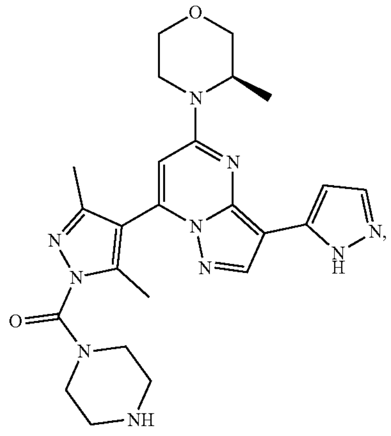
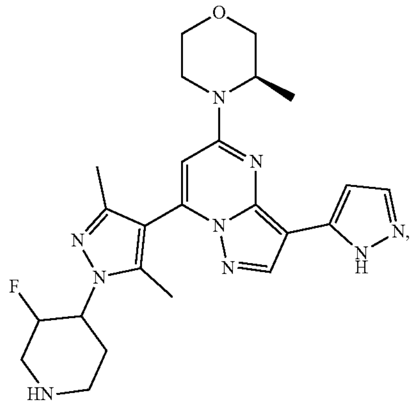
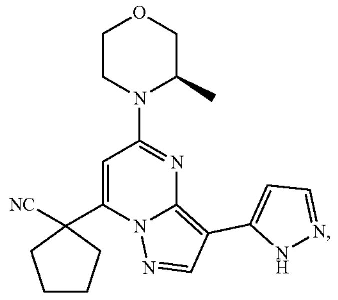
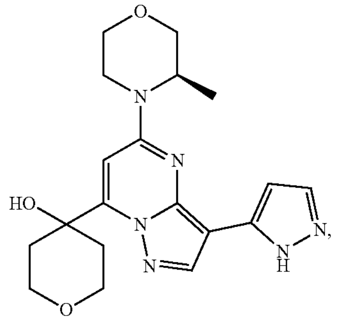

-continued

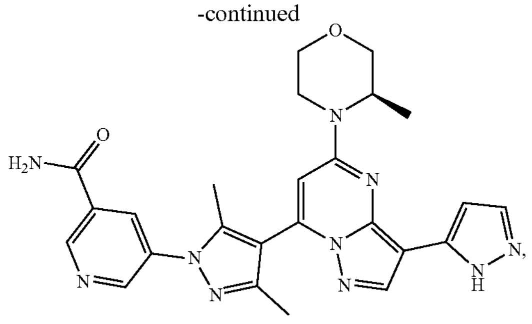

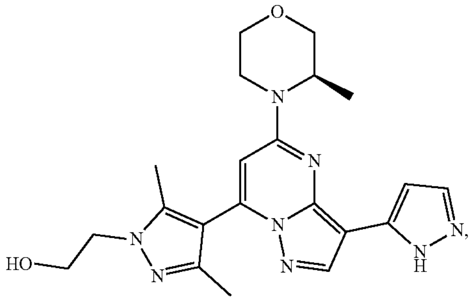

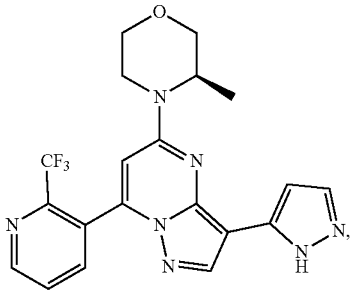

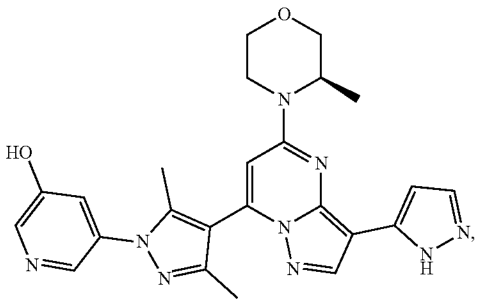

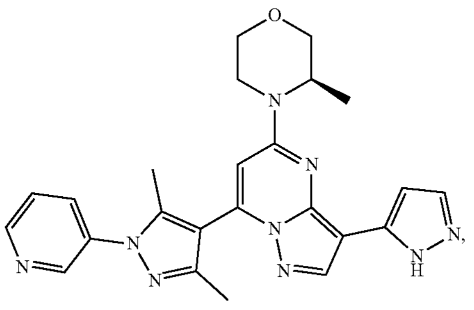

-continued

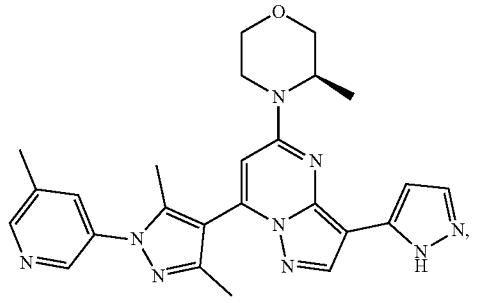

and

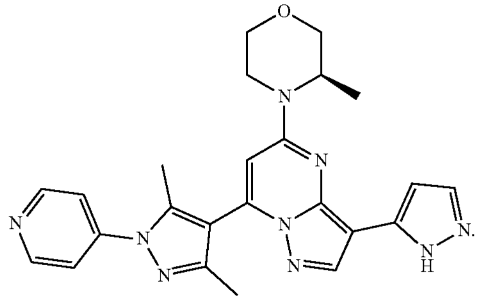

17. A pharmaceutical composition comprising the compound of claim 1, or a pharmaceutically acceptable salt, enantiomer, diastereomer, racemate, solvate, hydrate, polymorph, or isotopic variant thereof, and a pharmaceutically acceptable excipient; alternatively, further comprising other therapeutic agent(s).

18. A method of treating and/or preventing a disease mediated by ATR kinase in a subject, comprising administering to the subject the compound of claim 1 or a pharmaceutically acceptable salt, enantiomer, diastereomer, racemate, solvate, hydrate, polymorph, or isotopic variant thereof.

19. The method of claim 18, wherein the disease mediated by ATR kinase comprises a proliferative disease, leukemia or lymphoma.

20. The compound of claim 3, or a pharmaceutically acceptable salt, enantiomer, diastereomer, racemate, solvate, hydrate, polymorph, or isotopic variant thereof, or a mixture thereof, which is a compound of general formula (III-3) or (III-4):

(III-3)

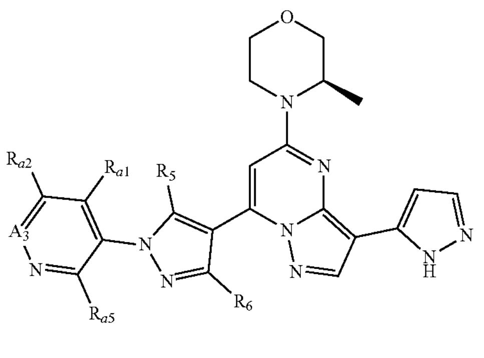

or

-continued (III-4)

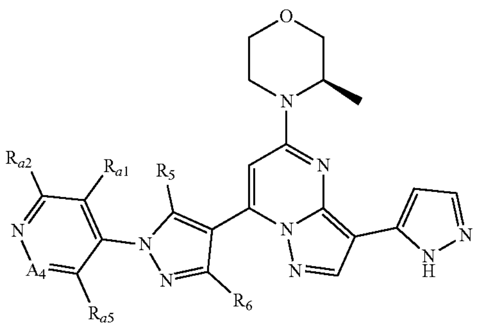

wherein $A_3$ is $CR_{a3}$ or N;

$A_4$ is $CR_{a3}$ or N;

$R_5$ and $R_6$ are independently $C_{1-6}$ alkyl, wherein the groups may be substituted by one or more D up to fully deuterated;

$R_{a1}$, $R_{a2}$, $R_{a3}$, $R_{a4}$ and Ras are independently selected from H, D, halogen, $C_{1-6}$ alkyl and $C_{1-6}$ haloalkyl, wherein the groups may be substituted by one or more D up to fully deuterated.

21. The compound of claim 20, or a pharmaceutically acceptable salt, enantiomer, diastereomer, racemate, solvate, hydrate, polymorph, or isotopic variant thereof, or a mixture thereof, which is a compound of general formula (III-3):

(III-3)

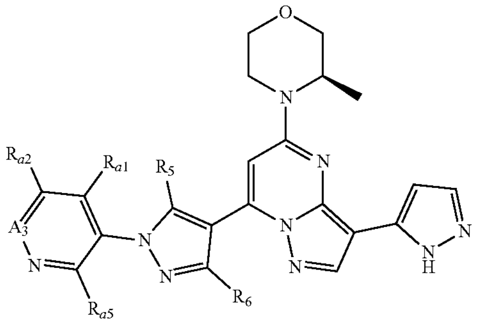

wherein $A_3$ is $CR_{a3}$;

$R_5$ and $R_6$ are independently $C_{1-6}$ alkyl; alternatively methyl;

$R_{a1}$ is H or D;

$R_{a2}$ is H, D, halogen, $C_{1-6}$ alkyl or $C_{1-6}$ haloalkyl;

$R_{a3}$ is H or D;

$R_{a5}$ is H or D.

22. A compound of claim 1 having the following structure:

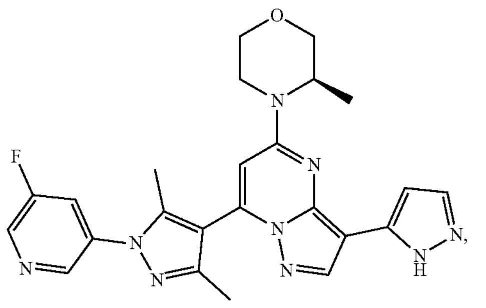

or a pharmaceutically acceptable salt thereof.

23. A compound of claim 1 having the following structure:

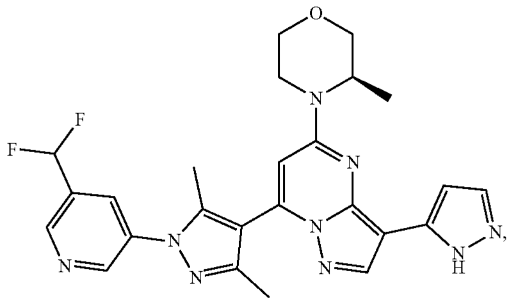 [SMILES: Cc1nn(-c2cncc(C(F)F)c2)c(C)c1-c1cc(N2CCOC[C@H]2C)nc2c(-c3ccn[nH]3)cnn12]

or a pharmaceutically acceptable salt thereof.

24. A compound of claim 1 having the following structure:

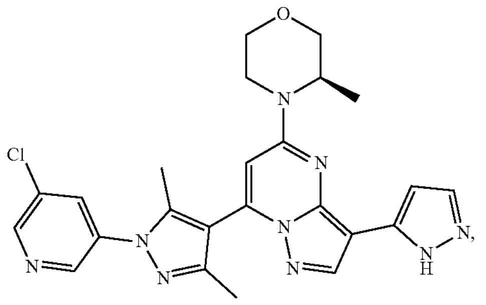 [SMILES: Cc1nn(-c2cncc(Cl)c2)c(C)c1-c1cc(N2CCOC[C@H]2C)nc2c(-c3ccn[nH]3)cnn12]

or a pharmaceutically acceptable salt thereof.

25. A compound of claim 1 having the following structure:

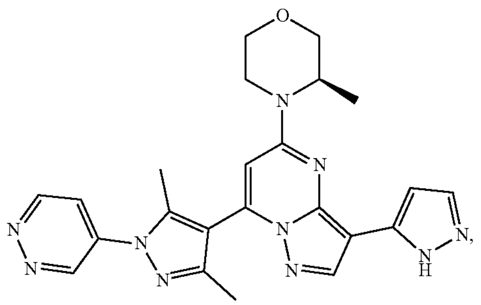 [SMILES: Cc1nn(-c2ccnnc2)c(C)c1-c1cc(N2CCOC[C@H]2C)nc2c(-c3ccn[nH]3)cnn12]

or a pharmaceutically acceptable salt thereof.

26. A compound of claim 1 having the following structure:

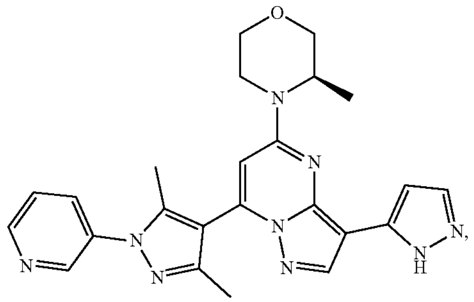 [SMILES: Cc1nn(-c2cccnc2)c(C)c1-c1cc(N2CCOC[C@H]2C)nc2c(-c3ccn[nH]3)cnn12]

or a pharmaceutically acceptable salt thereof.

27. A compound of claim 1 having the following structure:

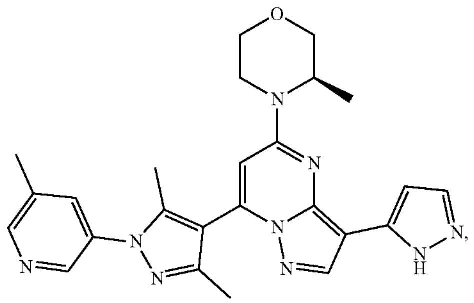 [SMILES: Cc1cncc(-n2nc(C)c(-c3cc(N4CCOC[C@H]4C)nc4c(-c5ccn[nH]5)cnn34)c2C)c1]

or a pharmaceutically acceptable salt thereof.

28. A compound of claim 1 having the following structure:

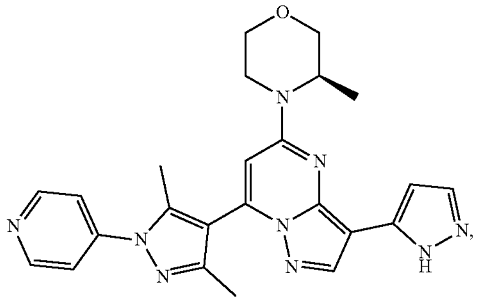 [SMILES: Cc1nn(-c2ccncc2)c(C)c1-c1cc(N2CCOC[C@H]2C)nc2c(-c3ccn[nH]3)cnn12]

or a pharmaceutically acceptable salt thereof.

29. The method of claim 18, wherein the disease mediated by ATR kinase comprises cancer, solid tumors, carcinoma, or sarcoma.

30. The method of claim 18, wherein the disease mediated by ATR kinase comprises breast cancer, colorectal cancer, lung cancer, prostate cancer and bile duct cancer, bone cancer, bladder cancer, head and neck cancer, kidney cancer, liver cancer, gastrointestinal cancer, esophageal cancer, ovarian cancer, pancreatic cancer, skin cancer, testicular cancer, thyroid cancer, uterine cancer, cervical cancer and vulvar cancer, and leukemia, multiple myeloma, or lymphoma.

31. The method of claim 18, wherein the disease mediated by ATR kinase comprises small cell lung cancer, non-small cell lung cancer and bronchioloalveolar carcinom, acute lymphoblastic leukemia (ALL), chronic myeloid leukemia (CML), or acute myeloid leukemia (AML).

* * * * *